US009550733B2

(12) United States Patent
Tam et al.

(10) Patent No.: US 9,550,733 B2
(45) Date of Patent: Jan. 24, 2017

(54) FLUORINATED DERIVATIVES OF 3-HYDROXYPYRIDIN-4-ONES

(71) Applicant: APOTEX TECHNOLOGIES INC., Toronto (CA)

(72) Inventors: Tim Fat Tam, Vaughan (CA); Regis Leung-Toung, Mississauga (CA); Yingsheng Wang, Richmond Hill (CA); Yanqing Zhao, Richmond Hill (CA); Tao Xin, Woodbridge (CA); Birenkumar Shah, Brampton (CA); Blaise N'Zemba, Brampton (CA); Jolanta Maria Wodzinska, Mississauga (CA); Maryna Premyslova, Vaughan (CA)

(73) Assignee: Apotex Technologies Inc., Toronto, Ontario (CA)

( * ) Notice: Subject to any disclaimer, the term of this patent is extended or adjusted under 35 U.S.C. 154(b) by 0 days.

(21) Appl. No.: 14/735,718

(22) Filed: Jun. 10, 2015

(65) Prior Publication Data
US 2015/0335626 A1 Nov. 26, 2015

Related U.S. Application Data

(62) Division of application No. 13/382,130, filed as application No. PCT/CA2010/001027 on Jul. 5, 2010, now Pat. No. 9,073,865.

(60) Provisional application No. 61/222,979, filed on Jul. 3, 2009.

(51) Int. Cl.
*A61K 31/4545* (2006.01)
*C07D 213/69* (2006.01)
*C07D 211/86* (2006.01)
*A61K 31/4412* (2006.01)
*A61K 31/496* (2006.01)
*C07D 213/74* (2006.01)
*C07D 401/06* (2006.01)

(52) U.S. Cl.
CPC ......... *C07D 213/69* (2013.01); *A61K 31/4412* (2013.01); *A61K 31/4545* (2013.01); *A61K 31/496* (2013.01); *C07D 211/86* (2013.01); *C07D 213/74* (2013.01); *C07D 401/06* (2013.01)

(58) Field of Classification Search
None
See application file for complete search history.

(56) References Cited

U.S. PATENT DOCUMENTS

| 2,918,402 A | 12/1959 | Frederick |
| RE25,831 E | 8/1965 | Moore |
| 4,585,780 A | 4/1986 | Hider et al. |
| 5,154,926 A | 10/1992 | Kawasaki et al. |
| RE34,313 E | 7/1993 | Hider et al. |
| 5,616,621 A | 4/1997 | Popli et al. |
| 5,658,919 A | 8/1997 | Ratnaraj et al. |
| 5,730,997 A | 3/1998 | Lienhop et al. |
| 5,763,449 A | 6/1998 | Anaebonam et al. |
| RE3,594 E | 11/1998 | Hider et al. |
| 5,928,885 A | 7/1999 | Nixon et al. |
| 5,962,461 A | 10/1999 | Anaebonam et al. |
| 6,133,322 A | 10/2000 | Rustin et al. |
| 6,472,378 B2 | 10/2002 | von Borstel |
| 6,506,911 B2 | 1/2003 | Hider et al. |
| 6,806,256 B2 | 10/2004 | Ulrich et al. |
| 6,855,711 B1 | 2/2005 | Warshawsky et al. |
| 6,906,052 B2 | 6/2005 | Shah |
| 6,956,028 B2 | 10/2005 | von Borstel |
| 6,989,397 B1 | 1/2006 | Richardson et al. |
| 8,026,261 B2 | 9/2011 | Tam et al. |
| 2002/0068758 A1 | 6/2002 | Hider et al. |
| 2003/0158234 A1 | 8/2003 | Spino et al. |
| 2003/0187019 A1 | 10/2003 | Ullah et al. |
| 2004/0101521 A1 | 5/2004 | Andersen |
| 2004/0116401 A1 | 6/2004 | Shah |
| 2005/0250738 A1 | 11/2005 | Mosher et al. |
| 2006/0030619 A1 | 2/2006 | Liu et al. |
| 2006/0093630 A1 | 5/2006 | Buehler |
| 2006/0100189 A1 | 5/2006 | Gurtner et al. |
| 2006/0234927 A1 | 10/2006 | Youdim et al. |
| 2006/0281748 A1 | 12/2006 | Gurtner et al. |
| 2007/0197469 A1 | 8/2007 | Murthy |
| 2007/0197649 A1 | 8/2007 | Munnich et al. |

(Continued)

FOREIGN PATENT DOCUMENTS

| CA | 1095921 A1 | 2/1981 |
| CA | 1290096 C | 10/1991 |

(Continued)

OTHER PUBLICATIONS

Simone, Oncology: Introduction, Cecil Textbook of Medicine, 20th Edition, 1996 vol. 1, pp. 1004-1010.*
Howington "Treatment of Stage I and II Non-small Cell Lung Cancer Diagnosis and Management of Lung Cancer, 3rd ed: American College of Chest Physicians Evidence-Based Clinical Practice Guidelines" Chest 2013; 143(5)(Suppl):e278S-e313S.*
Socinski "Treatment of Stage IV Non-small Cell Lung Cancer Diagnosis and Management of Lung Cancer, 3rd ed: American College of Chest Physicians Evidence-Based Clinical Practice Guideline" Chest 2013; 143(5)(Suppl):e341S-e368S.*

(Continued)

*Primary Examiner* — David K O'Dell
(74) *Attorney, Agent, or Firm* — The Webb Law Firm

(57) ABSTRACT

Provided are compounds of Formula I which are derivatives of 3-Hydroxypyridin-4-ones. The compounds may be used in treatment of a medical condition related to a toxic concentration of iron. The compounds may be used for preparation of a medicament for treatment of a medical condition related to a toxic concentration of iron. The medical condition related to a toxic concentration of iron may be selected from the group consisting of: cancer, pulmonary disease, progressive kidney disease and Friedreich's ataxia.

12 Claims, 14 Drawing Sheets

(56) References Cited

U.S. PATENT DOCUMENTS

| | | |
|---|---|---|
| 2008/0242706 A1 | 10/2008 | Tam et al. |
| 2009/0023784 A1 | 1/2009 | Munnich et al. |
| 2011/0039897 A1 | 2/2011 | Spino et al. |
| 2012/0095061 A1 | 4/2012 | Tam et al. |
| 2013/0190365 A1 | 7/2013 | Munnich et al. |

FOREIGN PATENT DOCUMENTS

| | | |
|---|---|---|
| CA | 2100158 A1 | 7/1992 |
| CA | 2226340 A1 | 1/1997 |
| CA | 2287907 A1 | 12/1998 |
| CA | 1340608 C | 6/1999 |
| DE | 10336497 A1 | 3/2005 |
| EP | 0120670 A1 | 10/1984 |
| EP | 0138420 A2 | 4/1985 |
| EP | 0336369 A1 | 10/1989 |
| EP | 1025858 A1 | 8/2000 |
| GB | 2136807 A | 9/1984 |
| WO | 9520584 A1 | 8/1995 |
| WO | 9527485 A1 | 10/1995 |
| WO | 0117530 A1 | 3/2001 |
| WO | 0202114 A1 | 1/2002 |
| WO | 03075910 A1 | 9/2003 |
| WO | 2007095728 A1 | 8/2007 |
| WO | 2008116301 A1 | 10/2008 |
| WO | 2009103950 A1 | 9/2009 |

OTHER PUBLICATIONS

Jett Treatment of Small Cell Lung Cancer Diagnosis and Management of Lung Cancer, 3rd ed: American College of Chest Physicians Evidence-Based Clinical Practice Guidelines Chest 2013; 143(5)(Suppl):e400S-e419S.*

Damia "Contemporary pre-clinical development of anticancer agents—What are the optimal preclinical models?" European Journal of Cancer 2009, 45, 2768-2781.*

Sharma "Cell line-based platforms to evaluate the therapeutic efficacy of candidate anticancer agents" Nature Reviews Cancer Apr. 2010, vol. 10, 241-253.*

Ocana, A. "Preclinical development of molecular targeted agents for cancer" Nat. Rev. Clin. Oncol. 2011, 8, 200-209.*

Ledford "US cancer institute overhauls cell lines" Nature Feb. 25, 2016 vol. 530 p. 391.*

Johnson, et. al. "Relationships between drug activity in NCI preclinical in vitro and in vivo models and early clinical trials." British Journal of Cancer 2001, 84, 1424-1431.*

Pandolfo "Deferiprone for the treatment of Friedreich's ataxia" Journal of Neurochemistry 2013, 126 (Suppl. 1), 142-146.*

Advances in Experimental Medicine and Biology vol. 652 Inherited Neuromuscular Diseases Translation From Pathomechanisms to Therapies Edited by Carmen Espin6s Vicente Felipo Francesc Palau Springer: 2009.*

Mancuso "Current and emerging treatment options in the management of Friedreich ataxia" Neuropsychiatric Disease and Treatment 2010:6 491-499.*

Ramos "Designing drugs that combat kidney damage" Expert Opinion on Drug Discovery (2015), 10(5), 541-556.*

Ribeiro "Iron therapy in chronic kidney disease: Recent changes, benefits and risks" Blood Reviews 30 (2016) 65-72.*

Merlot "Novel Chelators for Cancer Treatment: Where Are We Now?" Antioxidants & Redox Signaling vol. 18, No. 8, 2013, 973-1066.*

Hershko, Chaim et al. "Iron overload and chelation", Hematology, 2005, pp. 171-173, vol. 10, Supplement 1.

Hershko, Chaim et al. "Objectives and Mechanism of Iron Chelation Therapy", Annals of the New York Academy of Science, 2005, pp. 124-135, vol. 1054.

Hershko, Chaim et al. "ICL670A: a new synthetic oral chelator: evaluation in hypertransfused rats with selective radioiron probes of hepatocellular and reticuloendothelial iron stores and in iron-loaded rat hear cells in culture", Blood, 2001, pp. 1115-1122, vol. 97.

Kang, Sam Sik et al., "Neuroprotective effects of flavones on hydrogen peroxide-induced apoptosis in SH-SY5Y neuroblastoma cells", Bioorganic & Medicinal Chemistry Letters, 2004, pp. 2261-2264, vol. 14.

Kerns, E. et al., "Blood-Brain Barrier, Drug-Like Properties: Concepts, Structure Design and Methods", 2008, Elsevier.

Kontoghiorghes, G.J. et al. "The Design and Development of Deferiprone (L1) and Other Iron Chelators for Clinical Use: Targeting Methods and Application Prospects", Current Medicinal Chemistry, 2004, pp. 2161-2183, vol. 11.

Kurz, Tino et al., "Relocalized redox-active lysosomal iron is an important mediator of oxidative-stress-induced DNA damage", Biochemical Journal, 2004, pp. 1039-1045, vol. 378.

Lang, John C. et al. "Opthalmic Preparations", Remington: The Science and Practice of Pharmacy, Ed. David B. Troy, 2006, pp. 850-870, Lippincott Williams & Wilkins, Baltimore.

Lee, Thomas Wai-Yip et al., "Controlled-Release Drug-Delivery Systems", Remington: The Science and Practice of Pharmacy, Ed. Daniel Limmer, 2000, pp. 903-929, Lippincott Williams & Wilkins, Baltimore.

Lim, C.K. et al. "Protection against Hydrogen Peroxide-Mediated Cytotoxicity in Friedreich's Ataxia Fibroblasts using Novel Iron Chelators of the 2-Pyridylcarboxaldehyde Isonicotinoyl Hydrazone Class", Molecular Pharmacology, 2008, pp. 225-235, vol. 74.

Liu, Zu D. et al., "Design, Synthesis and Evaluation of N-Basic Substituted 3-Hydroxypyridin-4-ones: Orally Active Iron Chelators with Lysosomotrophic Potential", Journal of Pharmacy and Pharmacology, 2000, pp. 263-272, vol. 52.

Lodi, R. et al. "Antioxidant Treatment Improves in Vivo Cardiac and Skeletal Muscle Bioenergetics in Patients with Friedreich's Ataxia", Annals of Neurology, May 2001, pp. 590-596, vol. 49, No. 5.

Lodi, Raffaele et al. "Mitochondrial Dysfunction in Friedreich's ataxia", Biological Signals and Receptors, 2001, pp. 263-270, vol. 10.

Lovejoy, David B. et al. "PCTH: A Novel Orally Active Chelator for the Treatment of Iron Overload Disease", Hemoglobin, 2006, pp. 93-104, vol. 30, No. 1.

Lovell, M.A. et al. "Copper, iron and zinc in Alzheimer's disease senile plaques", Journal of the Neurological Sciences, 1998, pp. 47-52, vol. 158.

Mandel, Silvia A. et al., "Multifunctional Activities of Green Tea Catechins in Neuroprotection", Neurosignals, 2005, pp. 46-60, vol. 14.

Manitpisitkul, Prasarn et al. "Whatever happened to cassette-dosing pharmacokinetics?", Drug Discovery Today, 2004, pp. 652-658, vol. 9, No. 15.

Molina-Holgado, Francisco et al. "Neuroprotective Actions of an Iron Chelator Against Alzheimer's Disease—Relevant Insults", Alzheimer's and Dementia, 2006, p. S631, vol. 2, Issue 3.

Molina-Holgado, Francisco et al., "Metals ions and neurodegeneration", Biometals, 2007, pp. 639-654, vol. 20.

Mosmann, Tim, "Rapid Colorimetric Assay for Cellular Growth and Survival: Application to Proliferation and Cytotoxicity Assays", Journal of Immunological Methods, 1983, pp. 55-63, vol. 65.

Nairn, J.G., "Solutions, Emulsions, Suspensions, and Extracts", Remington: The Science and Practice of Pharmacy, Ed. Daniel Limmer, 2000, pp. 721-752, Lippincott Williams & Wilkins, Baltimore.

O'Connor, Robert E. et al. "Powders", Remington: The Science and Practice of Pharmacy. Ed. David B. Troy, 2006, pp. 702-719, Lippincott Williams & Wilkins, Baltimore.

Olivieri, Nancy F. et al. "tong-Term Safety and Effectiveness of Iron-Chelation Therapy with Deferiprone for Thalassemia Major", The New England Journal of Medicine, Aug. 13, 1998, pp. 417-423, vol. 339, No. 7, Massachusetts Medical Society.

Olivieri, Nancy F. et al. "Iron-Chelation Therapy with Oral Deferiprone in Patients with Thalassemia Major", The New England Journal of Medecine, 1995, pp. 918-922, vol. 332, No. 14.

(56) References Cited

OTHER PUBLICATIONS

Pardridge, William M., "CNC Drug Design Based on Principles of Blood-Brain Barrier Transport", Journal of Neurochemistry, 1998, pp. 1781-1792, vol. 70, No. 5.

Pearce, J.M. "Friedreich's ataxia", Journal of neurology neurosurgery and psychiatry, 2004, p. 688, vol. 75, No. 5.

Pennell, Dudley J. et al. "Randomized controlled trial of deferiprone or deferoxamine in beta-thalassemia major patients with asymptomatic myocardial siderosis", Blood, 2006, pp. 3738-3744, vol. 107, No. 9.

Persson, H. Lennart et al., "Iron-binding drugs targeted to lysosomes: a potential strategy to treat inflammatory lung disorders", Expert Opinion on Investigational Drugs, 2005, pp. 997-1008, vol. 14, No. 8.

Pierre, J.L. et al., "Iron and activated oxygen species in biology: The basic chemistry", BioMetals, 1999, pp. 195-199, vol. 12.

Pootrakul, Pensri et al. "Labile plasma iron (LPI) as an indicator of chelatable plasma redox activity in iron-overloaded β-thalassemia/HbE patients treated with an oral chelator", Blood, 2004, pp. 1504-1510, vol. 104, No. 5.

Porter, John B., "A Risk-Benefit Assessment of Iron-Chelation Therapy", Drug Safety,1997, pp. 407-421, vol. 17.

Porter, Stuart C. "Coating of Pharmaceutical Dosage Forms," Remington: The Science and Practice of Pharmacy, Ed. David B. Troy, 2006, pp. 929-938, Lippincott Williams & Wilkins, Baltimore.

Porter, Stuart C., "Coating of Pharmaceutical Dosage Forms," Remington: The Science and Practice of Pharmacy, Ed. Daniel Limmer, 2000, pp. 894-902, Lippincott Williams & Wilkins, Baltimore.

Richardson, Des R. "The therapeutic potential of iron chelators", Expert Opinion on Investigational Drugs, 1999, pp. 2141-2158, vol. 8. No. 12.

Richardson, D.R. et al. "Development of potential iron chelators for the treatment of Friedreich's ataxia: ligands that mobilize mitochondrial iron", Biochemica et Biophysica Acta, 2001, pp. 133-140, vol. 1536.

Richardson, D.R., "Friedrich's ataxia: iron chelators that target the mitochondrion as a therapeutic strategy?", Expert Opinion on Investigational Drugs, 2003, pp. 235-245, vol. 12, No. 2.

Richardson, Des R. "The controversial role of deferiprone in the treatment of thalassemia", Journal of Laboratory and Clinical Medicine, 2001, pp. 324-329, vol. 137, No. 5.

Richardson, Des R., "Novel chelators for Central Nervous System Disorders That Involve Alterations in the Metabolism of Iron and Other Metal Ions", Annals of the New York Academy of Sciences, 2004, pp. 326-341, vol. 1012.

Ritchie, Craig W. et al. "Metal-Protein Attenuation With Iodochlorhydroxyquin (Clioquinol) Targeting Aβ Amyloid Deposition and Toxicity in Alzheimer Disease—A Pilot Phase 2 Clinical Trial", Arch Neurol, 2003, pp. 1685-1691, vol. 60.

Rotig, Agnès et al., Aconitase and mitochondrial iron-sulphur protein deficiency in Friedreich ataxia, Nature Genetics, 1997, pp. 215-217, vol. 17.

Rudnic, Edward M. et al., "Oral Solid Dosage Forms",Remington: The Science and Practice of Pharmacy, Ed. Daniel Limmer, 2000, pp. 858-893, Lippincott Williams & Wilkins, Baltimore.

Rudnic, Edward M. et al., "Oral Solid Dosage Forms",Remington: The Science and Practice of Pharmacy, Ed. David B. Troy, 2006, pp. 889-928, Lippincott Williams & Wilkins, Baltimore.

Rund, Deborah et al., "β-Thalassemia", The New England Journal of Medicine, 2005, pp. 1135-1146, vol. 353.

Rustin, Pierre et al., "Effect of idebenone on cardiomyopathy in Friedreich's ataxia: a preliminary study", Lancet, 1999, pp. 477-479, vol. 354.

Sayre, Lawrence M. et al. "In Situ Oxidative Catalysis by Neurofibrillary Tangles and Senile Plaques in Alzheimer's Disease: A Central Role for Bound Transition Metals", Journal of Neurochemistry, 2000, pp. 270-279. vol. 74, No. 1.

Schlindwein, Walkiria et al. "New lipophilic 3-hydroxy-4-pyridinonate iron(III) complexes: synthesis and EXAFS structural characterisation", Dalton Transactions, 2006, pp. 1313-1321.

Sciarra, John J. et al., "Aerosols", Remington: The Science and Practice of Pharmacy, Ed. Daniel Limmer, 2000, pp. 963-979, Lippincott Williams & Wilkins, Baltimore.

Sciarra, John C. et al. "Aerosols", Remington: The Science and Practice of Pharmacy, Ed. David B. Troy, 2006, pp. 1000-1017, Lippincott Williams & Wilkins, Baltimore.

Shvartsman, Maya et al., "Non-transferrin-bound iron reaches mitochondria by a chelator-inaccessible mechanism: biological and clinical implications", American Journal of Physiology—Cell Physiology, 2007, pp. 1383-1394, vol. 293.

Simon, Delphine et al., "Friedreich Ataxia Mouse Models with Progressive Cerebellar and Sensory Ataxia Reveal Autophagic Neurodegeneration in Dorsal Root Ganglia", The Journal of Neuroscience, 2004, pp. 1987-1995, vol. 24. No. 8.

Akers, Michael J., et al.. "Parenteral Preparations", Remington: The Science and Practice of Pharmacy, Ed. David B. Troy, 2006, pp. 802-836, Lippincott Williams & Wilkins, Baltimore.

Annex I, "Summary of Product Characteristics", to European Commission Decision of Nov. 19, 2007 (labeled "Not for Publication") approving Apotex's Ferriprox® 100mg/ml oral solution, available at http://ec.europa.eu/health/documents/community-register/html/h108.htm (Jul. 17, 2013).

"Annex I—Summary of Product Characteristics" http://www.ferriprox.com/aboutferriprox/SPC_solution.pdf. On Nov. 12, 2008.

Apopharma, "Safety and Efficacy of Ferriprox™ (Deferiprone) Oral Solution in Iron Overloaded Pediatric Patients", NCT00529152, Sep. 12, 2007, ClinicalTrials.gov.

Avis, Kenneth E., et al., "Parenteral Preparations", Remington: The Science and Practice of Pharmacy, Ed. Daniel Limmer, 2000, pp. 780-806, Lippincott Williams & Wilkins, Baltimore.

Avramovich-Tirosh, Yael et al. "Therapeutic targets and potential of the novel brain-permeable multifunctional iron chelator-monoamine oxidase inhibitor drug, M-30, for the treatment of Alzheimer's disease", Journal of Neurochemistry, 2007, pp. 490-502, vol. 100.

Barnham, Kevin J. et al., "Metal-Protein Attenuating Compounds (MPACs) for the Treatment of Alzheimer's Disease", Drug Design Reviews-Online, 2004, pp. 75-82, vol. 1.

Becker, Erika et al. "Frataxin: its role in iron metabolism and the pathogenesis of Friedreich's ataxia", The International Journal of Biochemistry & Cell Biology, 2001, pp. 1-10, vol. 33.

Berkovitch et al. "The Efficacy of Oral Deferiprone in Acute Iron Poisoning". American Journal of Emergency Medicine. Jan. 2000. pp. 36-40. vol. 18. No. 1.

Block, Lawrence H., "Medicated Topicals", Remington: The Science and Practice of Pharmacy, Ed. Daniel . Limmer, 2000, pp. 836-857, Lippincott Williams & Wilkins, Baltimore.

Block, Lawrence H. "Medicated Topicals", Remington: The Science and Practice of Pharmacy, Ed. David B. Troy, 2006, pp. 871-888, Lippincott Williams & Wilkins, Baltimore.

Boddaert, Nathalie et al. "Selective Iron Chelation in Friedreich Ataxia. Biological and Clinical Implications", Blood, 2007, pp. 401-408, vol. 110.

Breuer, William et al. "Desferrioxamine-chelatable iron, a component of serum non-transferrin-bound iron, used for assessing chelation therapy", Blood, 2001, pp. 792-798, vol. 97, No. 3.

Bush, Ashley I. et al. "Rapid Induction of Alzheimer A# Amyloid Formation by Zinc", Science, 1994, pp. 1464-1467, vol. 265, No. 5177.

Buss, Joan L. et al., "The Role of Iron Chelation in Cancer Therapy", Current Medical Chemistry, 2003, pp. 1021-1034, vol. 10.

Campuzano, Victoria et al. "Friedreich's Ataxia: Autosomal Recessive Disease Caused by an Intronic Gaa Triplet Repeat Expansion", Science, 1996, vol. 271.

Cano, Stefan J. et al., "International Cooperative Ataxia Rating Scale (ICARS): Appropriate for Studies of Friedreich's Ataxia?", Movement Disorders, 2005, pp. 1585-1591, vol. 20, No. 12.

(56) References Cited

OTHER PUBLICATIONS

Carmichael, James et al., "Evaluation of a Tetrazolium-based Semiautomated Colorimetric Assay: Assessment of Chemosensitivity Testing", Cancer Research, Feb. 15, 1987, pp. 936-942, vol. 47.
Chamberlain, Susan et al., "Mapping of mutation causing Friedreich's ataxia to human chromosome 9", Nature, 1988, pp. 248-250, vol. 334.
Chantrel-Groussard, Karine et al., "Disabled early recruitment of antioxidant defenses in Friedreich's ataxia", Human Molecular Genetics, 2001, pp. 2061-2067, vol. 10, No. 19.
Cherny, Robert A. et al., "Aqueous Dissolution of Alzheimer's Disease Aβ Amyloid Deposits by Biometal Depletion", The Journal of Biological Chemistry, 1999, pp. 23223-23228. vol. 275, No. 33.
Cooper, Mindy A. et al., "Urinary Iron Speciation in Nephrotic Syndrome", American Journal of Kidney Diseases, Feb. 1995, pp. 314-319, vol. 25, No. 2.
Crowley, Michael M. "Solutions, Emulsions, Suspensions, and Extracts", Remington: The Science and Practice of Pharmacy, Ed. David B. Troy, 2006, pp. 745-775, Lippincott Williams & Wilkins, Baltimore.
Crivori, P. et al., "Predicting Blood-Brain Barrier Permeation from Three-Dimensional Molecular Structure", Journal of Medicinal Chemistry, 2000, pp. 2204-2216, vol. 43.
Crumbliss, Alvin L., "Iron Chelation in Biology", Virtual Free Radical School, http://www.medicine.uiowa.edu/FRRB/VirtualSchool/Crumbliss-Fe.pdf.
Crumbliss, Alvin L., "Iron Chelation in Biology", Virtual Free Radical School of the OxygenSoc, Buettner GR, Schafer FQ, eds, http://www.medicine.uiowa.edu/FRRB/VirtualSchool/Virtual.html (2002), Duke University, Durham, North Carolina, US. (invited).
Dean, Roger T. et al., "The Action of Nine Chelators on Iron-Dependent Radical Damage", Free Radical Res., 1994, pp. 83-101, vol. 20, No. 2.
Dehkordi, Lotfollah S., "Basic 3-hydroxypyridin-4-ones: Potential antimalarial agents", European Journal of Medical Chemistry, 2008, pp. 1035-1047, vol. 43.
Delatycki, Martin B. et al. "Direct Evidence that Mitochondrial Iron Accumulation Occurs in Friedreich Ataxia", Annals of Neurology, 1999, pp. 673-675, vol. 45, No. 5.
Delatycki, Martin B. et al. "Friedreich ataxia: from genes to therapies?", Medical Journal of Australia, 2005, p. 439, vol. 182. No. 9.
Delatycki, Martin B. et al. "Friedreich ataxia: an overview", Journal of Medical Genetics, 2000, pp. 1-8, vol. 37.
Dhungana, Suraj et al., "Coordination Properties of a New Saccharide-Based Exocyclic Trihydroxamate Analogue of Ferrichrome", Inorganic Chemistry, 2003, pp. 42-50, vol. 42.
Ding, Xuan et al. "Extended-Release and Targeted Drug Delivery Systems", Remington: The Science and Practice of Pharmacy, Ed. David B. Troy, 2006, pp. 939-964, Lippincott Williams & Wilkins, Baltimore.
Escudar-Gilabert, L. et al., "Potential of biopartitioning micellar chromatography as an in vitro technique for predicting drug penetration across the blood-brain barrier", Journal of Chromatography B, 2004, pp. 193-201, vol. 807.
European Commission Decision of Aug. 25, 1999 (labeled "Not for Publication") approving Apotex's Ferriprox® tablets, available at http://ec.europa.eu/health/documents/community-register/html/h108.htm (Jul. 17, 2013).
European Commission Decision of Nov. 19, 2007 (labeled "Not for Publication") approving Apotex's Ferriprox® 100mg/ml oral solution, available at http://ec.europa.eu/health/documents/community-register/html/h108.htm (Jul. 17, 2013).
"Ferriprox—Procedural steps taken and scientific information after the authorisation changes made after, Jan. 6, 2004", available at http://www.emea.europa.eu/humandocs/PDFs/EPAR/Ferriprox/038799en8b.pdf, document printed Nov. 12, 2008.
Forni, Gian Luca et al., "Regression of symptoms after selective iron chelation therapy in a case of neurodegeneration with brain iron accumulation.", Mov Discord, 2008, pp. 904-907, vol. 23, No. 6.

Franchini, Massimo et al. "Iron-chelation therapy: an update", The Hematology Journal, 2005, pp. 287-292, vol. 5.
Friedreich, N., Virchow's Arch Path Anat, 1863, pp. 391-419, vol. 26.
Gabbita, S. Prasad et al., "Increased Nuclear DNA Oxidation in the Brain in Alzheimer's Disease", Journal of Neurochemistry, 1998, pp. 2034-2040, vol. 71, No. 5.
Gaeta, Alessandra et al. "The crucial role of metal ions in neurodegeneration: the basis for a promising therapeutic strategy", British Journal of Pharmacology, 2005, pp. 1041-1059, vol. 146.
Gakh, Oleksandr et al. "Mitochondrial iron detoxification is a primary function of frataxin that limits oxidative damage and preserves cell longevity", Human Molecular Genetics, 2006, pp. 467-479, vol. 15, No. 3.
Giardina et al. "Chelation Therapy in β-Thalassemia: An Optimistic Update". Seminars in Hematology. Oct. 2001. pp. 360-366. vol. 38, No. 4.
Glickstein, Hava et al. "Intracellular labile iron pools as direct targets of iron chelators: a fluorescence study of chelator action in living cells", Blood, 2005, pp. 3242-3250, vol. 106, No. 9.
Goncalves, Sergio et al. "Deferiprone targets aconitase: Implication for Friedreich's ataxia treatment", BMC Neurology, 2008, vol. 8, No. 20.
Gutteridge, John M.C., "Superoxide-Dependent Formation of Hydroxyl Radicals from Ferric-Complexes and Hydrogen Peroxide: An Evaluation of Fourteen Iron Chelators", Free Radical Res., 1990, pp. 119-125, vol. 9, No. 2.
Haacke, E. Mark et al. "Imaging iron stores in the brain using magnetic resonance imaging", Magnetic Resonance Imaging, 2005, pp. 1-25, vol. 23.
Hausse, A. O. et al. "Idebenone and reduced cardiac hypertrophy in Friedreich's ataxia", Heart, 2002, pp. 346-349, vol. 87.
Hecht, Gerald, "Opthalmic Preparations", Remington: The Science and Practice of Pharmacy, Ed. Daniel Limmer, 2000, pp. 821-835, Lippincott Williams & Wilkins, Baltimore.
Sohn, Yang-Sung et al., "Redistribution of accumulated cell iron, A modality of chelation with therapeutic implications", Blood First Edition Paper, prepublished online Nov. 1, 2007.
Sopher, Bryce L. et al., "Cytotoxicity mediated by conditional expression of a carboxyl-terminal derivative of the β-amyloid precursor protein", Molecular Brain Research, 1994, pp. 207-217, vol. 26.
Sturm, Brigitte et al., "Friedreich's Ataxia, No Changes in Mitochondrial Labile Iron in Human Lymphoblasts and Fibroblasts—A Decrease in Antioxidative Capacity?", The Journal of Biological Chemistry, 2009, pp. 6701-6706, vol. 280, No. 8.
"Summary of Community Decisions on Marketing Authorizations in Respect of Medicinal Products from Nov. 1, 2007 to Nov. 30, 2007," Official Journal of the European Union C316/42 (Dec. 28, 2007), http://ec.europa.eu/health/documents/community-register/html/h108.htm.
Tam, Tim F., "Iron Chelator Research: Past, Present, and Future", Current Medicinal Chemistry, 2003, pp. 983-995, vol. 10.
Turco, Salvatore J., "Intravenous Admixtures", Remington: The Science and Practice of Pharmacy. Ed. Daniel Limmer, 2000, pp. 807-820, Lippincott Williams & Wilkins, Baltimore.
Turco, Salvatore J. "Intravenous Admixtures", Remington: The Science and Practice of Pharmacy. Ed. David B. Troy, 2006, pp. 837-849, Lippincott Williams & Wilkins, Baltimore.
Usansky, Helen H. et al. "Computation of Log BB values for compounds transported through carrier-mediated mechanisms using in vitro permeability data from brain microvessel endothelial cell (BMEC) monolayers", Pharmaceutical Research, 2003, p. 390, vol. 20, Issue 3.
Voncken, Max et al., "Friedreich ataxia—update on pathogenesis and possible therapies", Neurogenetics, 2004, pp. 1-8, vol. 5.
Waldvogel, Daniel et al., "Increased Iron in the Dentate Nucleus of Patients with Friedreich's Ataxia", Annals of Neurology, 1999, pp. 123-125, vol. 46, No. 1.
Whitnall, Megan et al., "The MCK mouse heart model of Friedreich's ataxia: Alterations in iron-regulated proteins and cardiac hypertrophy are limited by iron chelation", PNAS, 2008, pp. 6757-9762, vol. 105, No. 28.

(56) References Cited

OTHER PUBLICATIONS

Whitnall, Megan et al., "Iron: A new Target for Pharmacological Intervention in Neurodegenerative Diseases", Seminars in Pediatric Neurology, 2006, pp. 186-197, vol. 13.
Wilson, Robert B. et al., "Normal Serum Iron and Ferritin Concentrations in Patients with Friedreich's Ataxia", Annals of Neurology, 1998, pp. 132-134, vol. 44, No. 1.
Huang X, "Iron overload and its association with cancer risk in humans: evidence for iron as a carcinogenic metal," Mutation Research, 2003, pp. 153-171, vol. 533.
Whitnall M et al., "A class of iron chelators with a wide spectrum of potent antitumor activity that overcomes resistance to chemotherapeutics," Proceedings of the National Academy of Sciences, 2006, pp. 14901-14906, vol. 103, No. 40.

\* cited by examiner

FLUORINATED DERIVATIVES OF 3-HYDROXYPYRIDIN-4-ONES

CROSS-REFERENCE TO RELATED APPLICATIONS

This application claims priority as a divisional application to U.S. patent application Ser. No. 13/382,130, filed Jun. 21, 2012, which is the U.S. national stage of PCT Application No. PCT/CA2010/001027 filed Jul. 5, 2010, which claims priority from U.S. Provisional Application No. 61/222,979 filed Jul. 3, 2009, the entire contents of which are each expressly incorporated by reference.

BACKGROUND OF THE INVENTION

The occurrence of in vivo iron toxicity in the human body can be categorized into iron overload and non-iron overload conditions. Iron overload conditions are common in thalassemia patients through chronic blood transfusions and in hereditary hemochromatosis patients. Non-iron overloaded conditions include anthracycline mediated cardiotoxicity, viral infections, neurodegenerative diseases, photo induced damage, and proliferative conditions. The potential use of iron chelators in the treatment of a variety of diseases is reviewed in Tam et al., Current Medicinal Chemistry, 2003, 10, 983-995 and Hider et al., BioMetals, 2007, 20, 639-654.

At present, there are several iron chelator drugs that have reached the market. Examples of those include deferiprone (Ferriprox™), ICL670 (ExJade™), dexrazoxane hydrochloride (Zinecard™) and desferrioxamine mesylate (Desferal™). However, only two of these compounds, namely deferiprone and ICL670, are orally active for the removal of iron in iron-overloaded diseases.

SUMMARY OF THE INVENTION

In designing 3-hydroxypyridin-4-one that will lead to improved brain exposure, one approach is to increase the lipophilicity of the chelator via the introduction of a trifluoroethyl group at the C2 or C5 or C6 position of the 3-hydroxypyridin-4-one (US20080242706). This invention is based in part on compounds with a trifluoroethyl group at the N1 position, or a 2-difluoroethyl group at the C2 position of the 3-hydroxypyridin-4-one skeleton. The use of low molecular weight substituents is also considered in the design of new bidentate 3-hydroxypyridin-4-one ligands (L). A $ML_n$ complex is formed upon complexation with a metal (M), for example $FeL_3$.

Amines are known to have favorable interaction with predominately negatively charged phospholipids head groups at the BBB (blood brain barrier). In general, bases penetrate better into the CNS (central nervous system) (Chapter 10, Blood Brain Barrier in Drug-Like Properties: Concepts, Structure Design and Methods, by Edward H. Kerns and Li Di, Academic Press, Elsevier 2008). Herein, a series of amino derivatives with trifluoroethyl at the C2 or N1 or C5 or C6 position of the 3-hydroxypyridin-4-one backbone are designed and synthesized. Selected examples of those compounds are 2-[1-(dimethylamino)-2,2,2-trifluoroethyl]-3-hydroxy-1-methylpyridin-4(1H)-one (Apo7041), 5-[1-(dimethylamino)-2,2,2-trifluoroethyl]-3-hydroxy-1,2-dimethylpyridin-4(1H)-one (Apo7053), and 6-[(dimethylamino)methyl]-3-hydroxy-1-methyl-2-(2,2,2-trifluoroethyl)pyridin-4(1H)-one (Apo7021), and 2-[(dimethylamino)methyl]-3-hydroxy-1-(2,2,2-trifluoroethyl)pyridin-4(1H)-one (Apo7067).

This invention is based in part on a serendipitous discovery that amine derivatives such as 2-[1-(dimethylamino)-2,2,2-trifluoroethyl]-3-hydroxy-1-methylpyridin-4(1H)-one (Apo7041) are less favorable than deferiprone in BBB penetration in cassette dosing BBB studies in rats. Physicochemical studies confirm that Apo7041 (pKa=3.51) is less basic than normal aliphatic amines. Certain selected amine derivatives of this invention are weak bases and have pKas in the range of 3.5 to 6.0.

The weak bases of this invention are lipophilic and may also possess the ability to accumulate in the acidic compartment of biological systems. In addition, the metal chelates of compounds of this invention may have a distinctive property of being stable at significantly lower pHs than the metal chelate of deferiprone. The compounds of this invention may be useful in biological conditions such as treatment of cancer, inflammatory lung disorders and renal disease wherein the therapy requires a weak base to accumulate in the acidic compartment and sequester free iron under slightly acidic conditions to form a stable ferric chelate, which results in the removal of iron.

On the other hand, fluorinated derivatives of 3-hydroxypyridin-4-ones with a basic amine with pKa>6.0 have different properties than the weakly basic amines such as Apo7041. An example of such is 2-[(dimethylamino)methyl]-3-hydroxy-1-(2,2,2-trifluoroethyl)pyridin-4(1H)-one (Apo7067, pKa=6.1). Apo7067 is more lipophilic than deferiprone and readily penetrates the BBB in cassette dosing BBB studies in rats.

Non-amino fluorinated 3-hydroxypyridin-4-ones derivatives of this invention are generally more lipophilic than deferiprone and can accumulate in the brain region. Examples of those compounds are 3-hydroxy-2-methyl-1-(2,2,2-trifluoroethyl)pyridin-4(1H)-one (Apo6995), 3-hydroxy-2-(hydroxymethyl)-1-(2,2,2-trifluoroethyl)pyridin-4(1H)-one (Apo7064), 2-(2,2-difluoroethyl)-3-hydroxy-1-methylpyridin-4(1H)-one (Apo7080) and 2-(2,2-difluoro-1-hydroxyethyl)-3-hydroxy-1-methylpyridin-4(1H)-one (Apo7078). Compounds such as Apo6995 may be useful as low molecular weight iron chelators for accumulation in the brain. One possible use is the treatment of Friedreich's ataxia, wherein the site of iron removal or redistribution is in the brain.

In illustrative embodiments of the present invention there is provided a compound of Formula I:

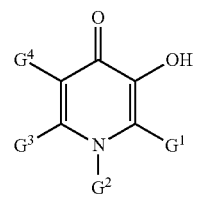

I wherein $G^1$ is H, $C_1$-$C_4$ alkyl, $CH_2OH$, $CH_2NR^1R^2$, $CH(R^4)CF_3$, $CH(R^7)CF_2H$, $NR^1R^2$, or

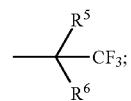

$G^2$ is H, $C_1$-$C_4$ alkyl, cyclopropyl or $(CH_2)_nCF_2R^3$; $G^3$ is H, $C_1$-$C_4$ alkyl, $CH_2OH$, $CH_2NR^1R^2$, $CH(R^6)CF_3$, $CH_2$-A-OH, $CH_2$-A-$NHR^9$ or $CH_2CF_3$ or

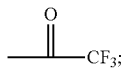

and $G^4$ is H, $C_1$-$C_4$ alkyl, halo or $CH(R^8)CF_3$; n is 1, 2 or 3; $R^1$ and $R^2$ are either (a) two independent groups or (b) together form a single ring group; $R^1$ and $R^2$, when independent groups, are independently selected from the group consisting of: H, $C_1$-$C_4$ alkyl, $C_3$-$C_6$ cycloalkyl, allyl, and propargyl; $R^1$ and $R^2$, when together form a single ring group, are selected from the group consisting of: piperazinyl, N—($C_1$-$C_4$ alkyl)-substituted piperazinyl, morpholinyl, and piperidinyl; $R^3$ is H or F; $R^4$ and $R^7$ are independently selected from the group consisting of: H, OH, $NR^1R^2$, imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl and -A-NH—$R^{10}$; and when $R^4$ or $R^7$ is imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl or -A-NH—$R^{10}$, a point of attachment of $R^4$ or $R^7$ to the CH moiety of $G^1$ is an N atom of $R^4$ or $R^7$; $R^5$ is $C_1$-$C_4$ alkyl; $R^6$ is H or OH; $R^8$ is selected from the group consisting of: $NR^1R^2$, imidazolyl, 1-2-4-triazolyl, piperazinyl, alkylpiperazinyl, N-benzylpiperazinyl, N-phenylpiperazinyl, 2-pyridylpiperazinyl and -A-NH—$R^{10}$; and when $R^8$ is imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl or -A-NH—$R^{10}$ a point of attachment of $R^8$ to the CH moiety of $G^4$ is an N atom of $R^8$; $R^9$ and $R^{10}$ are independently H or $C_1$-$C_4$ alkyl; A is —NH—$(CH_2)_m$—CO— or an alpha amino acid residue; m is 1, 2 or 3; and provided that: at least one of $G^1$, $G^2$, $G^3$ and $G^4$ comprise at least one fluorine moiety; when $G^1$ is $CH(R^4)CF_3$ and $R^4$ is H or OH, then either (i) $G^3$ is $CH_2NR^1R^2$, $CH_2$-A-OH, $CH_2$-A-$NHR^9$ or (ii) $G^4$ is halo or $CH(NR^1R^2)CF_3$; and when $G^3$ is $CH(R^6)CF_3$, then $G^1$ is $CH_2NR^1R^2$, $CH(R^4)CF_3$, $CH(R^7)CF_2H$, $NR^1R^2$ or

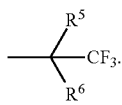

In illustrative embodiments of the present invention, there is provided use of a compound described herein for treatment of a medical condition related to a toxic concentration of iron. The use may be for preparation of a medicament. The medical condition related to a toxic concentration of iron may be selected from the group consisting of: cancer, pulmonary disease, progressive kidney disease and Friedreich's ataxia.

In illustrative embodiments of the present invention, there is provided a method of medical treatment comprising administering a therapeutically effective amount of a compound described herein to a subject having or suspected of having a medical condition related to a toxic concentration of iron. The medical condition related to a toxic concentration of iron may be selected from the group consisting of: cancer, pulmonary disease, progressive kidney disease and Friedreich's ataxia.

Other aspects and features of the present invention will become apparent to those ordinarily skilled in the art upon review of the following description of specific embodiments of the invention in conjunction with the accompanying figures.

DETAILED DESCRIPTION OF THE INVENTION

Figure 1:
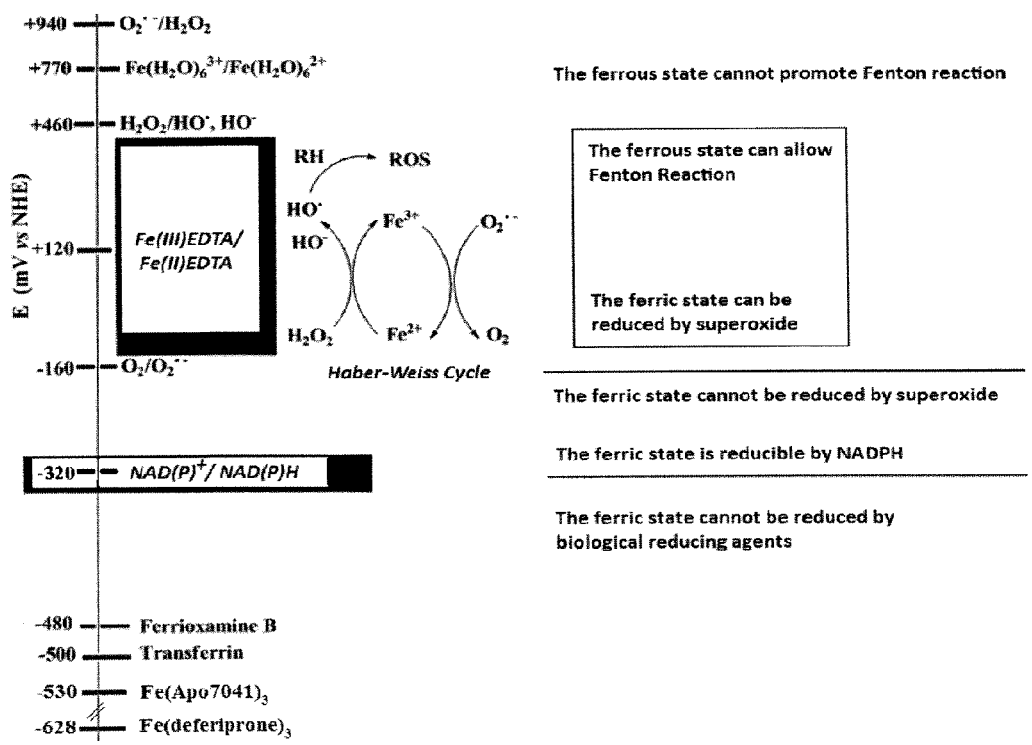
FIG. 1 is a diagrammatic representation of $E_{1/2}$ zone of established drugs such as deferiprone and desferrioxamine B. When a ferric chelate has an $E_{1/2}$ value that falls below −320 mV (mV vs. NHE), the chelate is not redox active and its properties fall within the $E_{1/2}$ zone of established drugs such as deferiprone and desferrioxamine B, and body protein such as transferrin. Compounds of Formula I have $E_{1/2}$ values that fall within the zone between ferrioxamine B (iron chelate of desferrioxamine B) and Fe(deferiprone)$_3$. Both deferiprone and Apo7041 are 3-hydroxypyridin-4-one derivatives. Deferiprone is 3-hydroxy-1,2-dimethylpyridin-4(1H)-one and Apo7041 is 2-[1-(dimethylamino)-2,2,2-trifluoroethyl]-3-hydroxy-1-methylpyridin-4(1H)-one.

Compounds of the present invention comprise compounds having a structure according to Formula I:

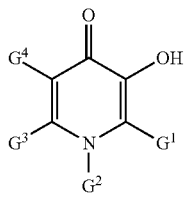

wherein
$G^1$ is H, $C_1$-$C_4$ alkyl, $CH_2OH$, $CH_2NR^1R^2$, $CH(R^4)CF_3$, $CH(R^7)CF_2H$, $NR^1R^2$, or

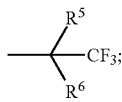

$G^2$ is H, $C_1$-$C_4$ alkyl, cyclopropyl or $(CH_2)_nCF_2R^3$;
$G^3$ is H, $C_1$-$C_4$ alkyl, $CH_2OH$, $CH_2NR^1R^2$, $CH(R^6)CF_3$, $CH_2$-A-OH, $CH_2$-A-$NHR^9$ or $CH_2CF_3$ or

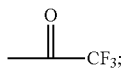

and
$G^4$ is H, $C_1$-$C_4$ alkyl, halo or $CH(R^8)CF_3$;
n is 1, 2 or 3;
$R^1$ and $R^2$ are either (a) two independent groups or (b) together form a single ring group;
$R^1$ and $R^2$, when independent groups, are independently selected from the group consisting of: H, $C_1$-$C_4$ alkyl, $C_3$-$C_6$ cycloalkyl, allyl, and propargyl;
$R^1$ and $R^2$, when together form a single ring group, are selected from the group consisting of: piperazinyl, N—($C_1$-$C_4$ alkyl)-substituted piperazinyl, morpholinyl, and piperidinyl;
$R^3$ is H or F;
$R^4$ and $R^7$ are independently selected from the group consisting of: H, OH, $NR^1R^2$, imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl and -A-NH—$R^{10}$; and when $R^4$ or $R^7$ is imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl or -A-NH—$R^{10}$, a point of attachment of $R^4$ or $R^7$ to the CH moiety of $G^1$ is an N atom of $R^4$ or $R^7$;
$R^5$ is $C_1$-$C_4$ alkyl;
$R^6$ is H or OH;
$R^8$ is selected from the group consisting of: $NR^1R^2$, imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl and -A-NH—$R^{10}$; and when $R^8$ is imidazolyl, 1-2-4-triazolyl, piperazinyl, N—$C_1$-$C_4$ alkylpiperazinyl, N-benzylpiperazinyl, N-phenylpiperazinyl, 2-pyridylpiperazinyl or -A-NH—$R^{10}$ a point of attachment of $R^8$ to the CH moiety of $G^4$ is an N atom of $R^8$;
$R^9$ and $R^{10}$ are independently H or $C_1$-$C_4$ alkyl;
A is —NH—$(CH_2)_m$—CO— or an alpha amino acid residue;
m is 1, 2 or 3; and
provided that:
at least one of $G^1$, $G^2$, $G^3$ and $G^4$ comprise at least one fluorine moiety;
when $G^1$ is $CH(R^4)CF_3$ and $R^4$ is H or OH, then either (i) $G^3$ is $CH_2NR^1R^2$, $CH_2$-A-OH, $CH_2$-A-$NHR^9$ or (ii) $G^4$ is halo or $CH(NR^1R^2)CF_3$; and
when $G^3$ is $CH(R^6)CF_3$, then $G^1$ is $CH_2NR^1R^2$, $CH(R^4)CF_3$, $CH(R^7)CF_2H$, $NR^1R^2$ or

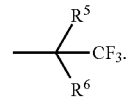

When $G^1$ comprises a fluorine moiety, then $G^1$ is selected from the group consisting of: $CH(R^4)CF_3$, $CH(R^7)CF_2H$, and

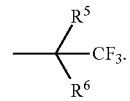

When $G^2$ comprises a fluorine moiety, then $G^2$ is $(CH_2)_n CF_2R^3$.
When $G^3$ comprises a fluorine moiety, then $G^3$ is selected from the group consisting of: $CH(R^6)CF_3$, $CH_2CF_3$ and

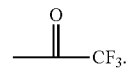

When $G^4$ comprises a fluorine moiety, then $G^4$ is $CH(R^8)CF_3$.

As used throughout this document, unless otherwise made clear by the context, A may be —NH—$(CH_2)_m$—CO— wherein m is 1, 2, or 3 or an alpha amino acid residue. A has a point of attachment to the compound via a nitrogen atom (N atom). The attachment point may be, for example, at the N-terminal of the amino acid residue. If the amino acid is lysine or ornithine, it is possible that either the alpha N or epsilon N of lysine or the alpha N or delta N of ornithine can be the attachment point. In the A-$NHR^9$ or A-$NHR^{10}$ moieties, the carboxylic acid of the amino acid residue forms an amide with the nitrogen atom of $NHR^9$ or $NHR^{10}$. In the A-OH moieties, the C-terminal of the amino acid residue is a carboxylic acid;

As used herein, an amino acid residue includes, but is not limited to, any of the naturally occurring alpha-, beta-, and gamma-amino carboxylic acids, including their D and L optical isomers, and the N-lower alkyl- and N-phenyl lower alkyl-derivatives of these amino acids. The amino acid residue is bonded through a nitrogen of the amino acid. The naturally occurring amino acids which can be incorporated into the present invention include, but are not limited to, alanine (ala), arginine (arg), asparagine (asn), aspartic acid (asp), cysteine (cys), cystine, glutamic acid (glu), glutamine (gin), glycine (gly), histidine (his), isoleucine (iso), leucine (leu), lysine (lys), methionine (met), ornithine (orn), phenylalanine (phe), proline (pro), serine (ser), threonine (thr), thyroxine, tryptophan (trp), tyrosine (tyr), valine (val), beta-alanine (β-ala), and gamma-aminobutyric acid (gaba). Preferred amino acid residues include proline, leucine, phenylalanine, isoleucine, alanine, gamma-amino butyric acid, valine, glycine, and phenylglycine.

All alpha-amino acids except glycine contain at least one asymmetric carbon atom. As a result, they are optically active, existing in either D or L form as a racemic mixture. Accordingly, some of the compounds of the present invention may be prepared in optically active form, or as racemic mixtures of the compounds claimed herein.

For example, the term A-OH wherein A is D-alanyl has the following structure:

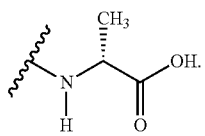 [SMILES: *N[C@H](C)C(=O)O]

The term A-NHMe wherein A is D-alanyl has the following structure

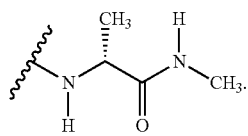

The term A-OH wherein A is —NH—$(CH_2)_m$—CO— and m is 2 has the following structure:

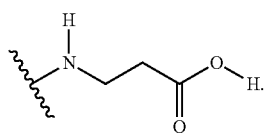

The term A-NHMe wherein A is epsilon-lysyl has the following structure:

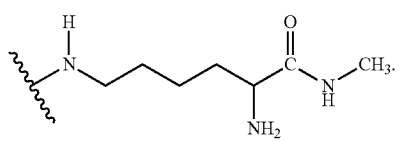 [SMILES: *NCCCCC(N)C(=O)NC]

The term A-NHMe wherein A is alpha-lysyl has the following structure:

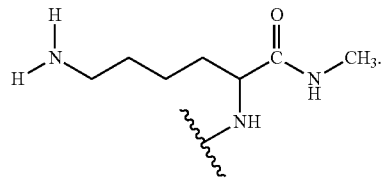 [SMILES: *NC(CCCCN)C(=O)NC]

As used herein, the term "alkyl," by itself or as part of another substituent, means, unless otherwise stated, a straight or branched chain hydrocarbon radical, and can include di- and multivalent radicals, having the number of carbon atoms designated (i.e. $C_1$-$C_{10}$ or 1- to 10-membered means one to ten carbons). If not expressly indicated, the number of carbons in an alkyl group may be considered to be $C_1$-$C_{10}$. and any of the other ranges and/or specific numbers therein. Examples of hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. The term "alkyl," unless otherwise noted, is not meant to include derivatives of alkyl such as "heteroalkyl."

The term "cycloalkyl", by themselves or in combination with other terms, represent, unless otherwise stated, cyclic versions of "alkyl". Examples of cycloalkyl include, but are not limited to, cyclopentyl, cyclohexyl, cycloheptyl, and the like.

The terms "halo" or "halogen" by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

As used herein, the term "substituted" refers to the replacement of a hydrogen atom on a compound with a substituent group. A substituent may be a non-hydrogen atom or multiple atoms of which at least one is a non-hydrogen atom and one or more may or may not be hydrogen atoms. For example, without limitation, substituted compounds may comprise one or more substituents selected from the group consisting of: R", OR", NR"R"', SR", halogen, SiR"R"'R"", OC(O)R", C(O)R", $CO_2$R", CONR"R"', NR"'C(O)$_2$R", S(O)R", S(O)$_2$R", CN and $NO_2$. As used herein, each R", R"', and R"" may be selected, independently, from the group consisting of: hydrogen, halogen, oxygen, substituted or unsubstituted heteroalkyl, substituted or unsubstituted aryl, substituted or unsubstituted alkyl, alkoxy or thioalkoxy groups, and arylalkyl groups.

"Moiety" refers to the radical of a molecule that is attached to another moiety. In particular, the term "Fluorine moiety" refers to the radical of a molecule that comprises at least one fluorine radical and/or atom.

Some embodiments of Formula I provide compounds wherein when $G^1$ is CH(NR$^1$R$^2$)CF$_3$, then $G^3$ and $G^4$ are independently H or $C_1$-$C_4$ alkyl, and $G^2$ is H, $C_1$-$C_4$ alkyl or cyclopropyl.

Some embodiments of Formula I provide compounds wherein when $G^2$ is $(CH_2)_n$CF$_2$R$^3$, then $G^1$ and $G^3$ are independently H, $C_1$-$C_4$ alkyl, $CH_2$OH or $CH_2$NR$^1$R$^2$.

Some embodiments of Formula I provide compounds wherein when $G^2$ is H, then $G^4$ is H or $C_1$-$C_4$ alkyl.

Some embodiments of Formula I provide compounds wherein when $G^3$ is

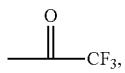

then $G^1$ and $G^4$ are independently H or $C_1$-$C_4$ alkyl.

Some embodiments of Formula I provide compounds wherein when $G^3$ is $CH_2CF_3$, then $G^1$ is $NR^1R^2$.

Some embodiments of Formula I provide compounds wherein when G is $CH_2NR^1R^2$, then $G^2$ is $(CH_2)_nCF_2R^3$.

Some embodiments of Formula I provide compounds wherein when $G^1$ is $CH(R^7)CF_2H$, then $G^3$ and $G^4$ are independently H or $C_1$-$C_4$ alkyl, and $G^2$ is $C_1$-$C_4$ alkyl or cyclopropyl.

Some embodiments of Formula I provide compounds wherein when $G^1$ is $CH(R^4)CF_3$, then $G^2$ is $C_1$-$C_4$ alkyl or cyclopropyl; provided that when $R^4$ is H or OH, then $G^3$ is $CH_2NR^1R^2$, $CH_2$-A-OH, $CH_2$-A-$NHR^9$.

Some embodiments of Formula I provide compounds wherein when $G^1$ is $CH(R^4)CF_3$ and $R^4$ is H or OH, then $G^4$ is halo.

Some embodiments of Formula I provide compounds wherein when $G^1$ or $G^3$ is $CH_2OH$, then $G^2$ is $(CH_2)_nCF_2R^3$.

Some embodiments of Formula I provide compounds wherein when $G^1$ is $NR^1R^2$, then $G^3$ is $CH_2CF_3$, $G^4$ is H or $C_1$-$C_4$ alkyl and $G^2$ is $C_1$-$C_4$ alkyl or cyclopropyl.

Some embodiments of Formula I provide compounds wherein when $G^4$ is $CH(R^8)CF_3$, then $G^1$ and $G^3$ are independently H or $C_1$-$C_4$ alkyl, and $G^2$ is hydrogen, $C_1$-$C_4$ alkyl or cyclopropyl.

Some embodiments of Formula I provide compounds wherein when $G^3$ is $CH_2$-A-OH or $CH_2$-A-NHR, then $G^4$ is H or $C_1$-$C_4$ alkyl, $G^2$ is $C_1$-$C_4$ alkyl or cyclopropyl and $G^1$ is $CH(R^4)CF_3$ where $R^4$ is H or OH.

Some embodiments of Formula I provide compounds wherein when $G^3$ is $CH_2NR^1R^2$, and $G^2$ is $C_1$-$C_4$ alkyl or cyclopropyl, then $G^4$ is H or $C_1$-$C_4$ alkyl, and $G^1$ is $CH(R^4)CF_3$ where $R^4$ is H or OH.

Some embodiments of Formula I provide compounds wherein when $G^1$ is $CH(R^4)CF_3$ and $R^4$ is H or OH, then either $G^3$ is $CH_2NR^1R^2$ or $G^4$ is halo.

Some embodiments of Formula I provide compounds wherein when $G^3$ is $CH(R^6)CF_3$, then $G^1$ is $CH_2NR^1R^2$ or $NR^1R^2$.

Some embodiments of Formula I provide compounds having a structure of Formula II

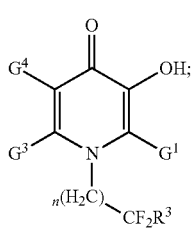

II wherein
$G^1$ is H, $C_1$-$C_4$ alkyl, —$CH_2OH$, or —$CH_2NR^1R^2$;
$G^3$ is H, $C_1$-$C_4$ alkyl, —$CH_2OH$, or —$CH_2NR^1R^2$;
$G^4$ is H, $C_1$-$C_4$ alkyl, or halo;

$R^1$ and $R^2$ are either (a) two independent groups or (b) together form a single ring group including the N to which they are bonded;

$R^1$ and $R^2$, when independent groups, are independently selected from the group consisting of: H, $C_1$-$C_4$ alkyl, $C_3$-$C_6$ cycloalkyl, allyl, and propargyl;

$R^1$ and $R^2$, when together form a single ring group including the N to which they are bonded, are selected from the group consisting of: piperazinyl, N—($C_1$-$C_4$ alkyl)-substituted piperazinyl, morpholino, and piperidinyl;

n is 1, 2 or 3; and $R^3$ is H, or F.

Some embodiments of Formula II provide compounds wherein n is 1.

Some embodiments of Formula II provide compounds wherein $G^4$ is H.

Some embodiments of Formula II provide compounds wherein $R^3$ is H.

Some embodiments of Formula II provide compounds wherein $R^3$ is F.

An example of a particular illustrative embodiment of Formula II is a compound in which $G^4$ is H; $G^3$ is methyl, $R^3$ is F, $G^2$ is trifluoroethyl, and $G^1$ is H. This compound may be termed 5-hydroxy-2-methyl-1-(2,2,2-trifluoroethyl)pyridin-4(1H)-one,

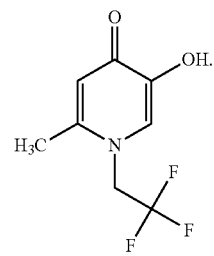

An example of a particular illustrative embodiment of Formula II is a compound in which $G^4$ is H; $G^3$ is H, $R^3$ is F, $G^2$ is trifluoroethyl, and $G^1$ is methyl. This compound may be termed 3-hydroxy-2-methyl-1-(2,2,2-trifluoroethyl)pyridin-4(1H)-one,

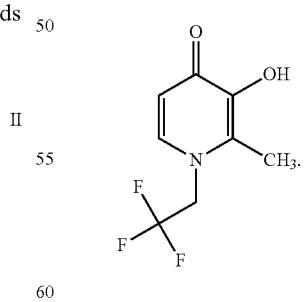

An example of a particular illustrative embodiment of Formula II is a compound in which $G^4$ is H; $G^3$ is H, $R^3$ is F, $G^2$ is trifluoroethyl, and $G^1$ is ethyl. This compound may be termed 2-ethyl-3-hydroxy-1-(2,2,2-trifluoroethyl)pyridin-4(1H)-one,

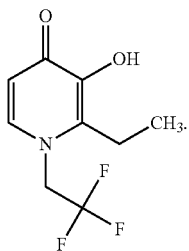 [SMILES: CCc1c(O)c(=O)ccn1CC(F)(F)F]

An example of a particular illustrative embodiment of Formula II is a compound in which $G^4$ is H; $G^3$ is H, $R^3$ is F, $G^2$ is trifluoroethyl, and $G^1$ is H. This compound may be termed 3-hydroxy-1-(2,2,2-trifluoroethyl)pyridin-4(1H)-one,

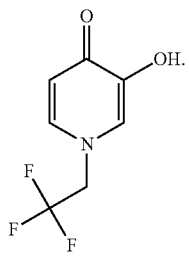 [SMILES: O=c1ccn(CC(F)(F)F)cc1O]

An example of a particular illustrative embodiment of Formula II is a compound in which $G^4$ is H; $G^3$ is H, $R^3$ is F, $G^2$ is trifluoroethyl, and $G^1$ is $CH_2OH$. This compound may be termed 3-hydroxy-2-(hydroxymethyl)-1-(2,2,2-trifluoroethyl)pyridin-4(1H)-one,

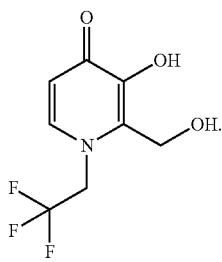 [SMILES: O=c1ccn(CC(F)(F)F)c(CO)c1O]

An example of a particular illustrative embodiment of Formula II is a compound in which $G^4$ is H; $G^3$ is methyl, $R^3$ is F, $G^2$ is trifluoroethyl, and $G^1$ is $CH_2NR^1R^2$ wherein $R^1$ is methyl and $R^2$ is methyl. This compound may be termed 2-[(dimethylamino)methyl]-3-hydroxy-6-methyl-1-(2,2,2-trifluoroethyl)pyridin-4(1H)-one,

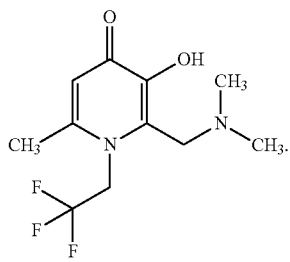 [SMILES: Cc1cc(=O)c(O)c(CN(C)C)n1CC(F)(F)F]

An example of a particular illustrative embodiment of Formula II is a compound in which $G^4$ is H; $G^3$ is H, $R^3$ is F, $G^2$ is trifluoroethyl, and $G^1$ is $CH_2NR^1R^2$ wherein $R^1$ is methyl and $R^2$ is methyl. This compound may be termed 2-[(dimethylamino)methyl]-3-hydroxy-1-(2,2,2-trifluoroethyl)pyridin-4(1H)-one,

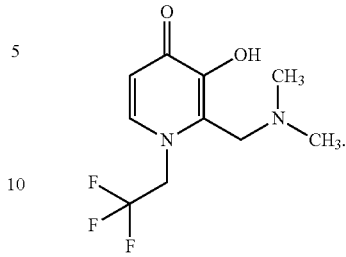

An example of a particular illustrative embodiment of Formula II is a compound in which $G^4$ is H; $G^3$ is methyl, $R^3$ is F, $G^2$ is trifluoroethyl, and $G^1$ is $CH_2OH$. This compound may be termed 3-hydroxy-2-(hydroxymethyl)-6-methyl-1-(2,2,2-trifluoroethyl)pyridin-4(1H)-one,

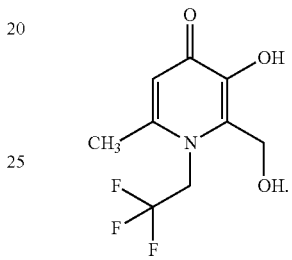

An example of a particular illustrative embodiment of Formula II is a compound in which $G^4$ is H; $G^3$ is methyl, $R^3$ is F, $G^2$ is trifluoroethyl, and $G^1$ is $CH_2NR^1R^2$ wherein $NR^1R^2$ is piperidinyl. This compound may be termed 3-hydroxy-6-methyl-2-(piperidin-1-ylmethyl)-1-(2,2,2-trifluoroethyl)pyridin-4(1H)-one,

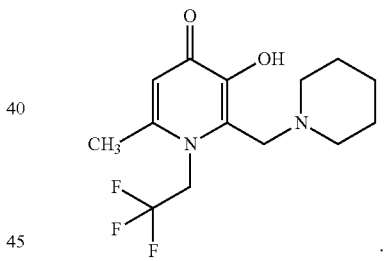

An example of a particular illustrative embodiment of Formula 0.11 is a compound in which $G^4$ is H; $G^3$ is H, $R^3$ is H, $G^2$ is difluoroethyl, and $G^1$ is methyl. This compound may be termed 1-(2,2-difluoroethyl)-3-hydroxy-2-methyl-pyridin-4(1H)-one,

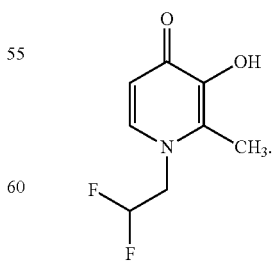

An example of a particular illustrative embodiment of Formula II is a compound in which $G^4$ is H; $G^3$ is methyl, $R^3$ is H, $G^2$ is difluoroethyl, and $G^1$ is H. This compound may be termed 1-(2,2-difluoroethyl)-5-hydroxy-2-methylpyridin-4(1H)-one,

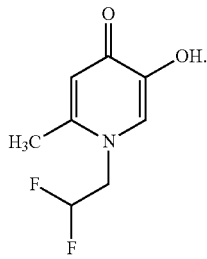

An example of a particular illustrative embodiment of Formula II is a compound in which $G^4$ is H; $G^3$ is methyl, $R^3$ is H, $G^2$ is difluoroethyl, and $G^1$ is $CH_2NR^1R^2$, $R^1$ is methyl and $R^2$ is methyl. This compound may termed 1-(2,2-difluoroethyl)-2-[(dimethylamino)methyl]-3-hydroxy-6-methylpyridin-4(1H)-one,

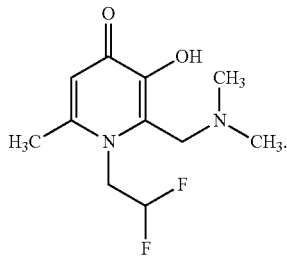 [SMILES: Cc1cc(=O)c(O)c(CN(C)C)n1CC(F)F]

Some embodiments of Formula I provide compounds having a structure of Formula III

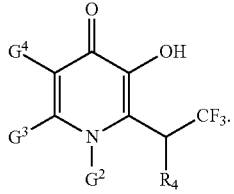

wherein $G^2$ is H, $C_1$-$C_4$ alkyl, or cyclopropyl;

$G^3$ is H, $C_1$-$C_4$ alkyl, $CH_2$-A-OH, $CH_2$-A-$NHR^9$, or $CH_2NR^1R^2$;

$G^4$ is H, $C_1$-$C_4$ alkyl, or halo;

$R^4$ is selected from the group consisting of: H, OH, $NR^1R^2$, imidazole, 1,2,4-triazole, piperazine, N—$C_1$-$C_4$ alkylpiperazine, N-benzylpiperazine, N-phenylpiperazine, 2-pyridylpiperazine, and -A-NH—$R^{10}$; and when $R^4$ is $NR^1R^2$, imidazole, 1,2,4-triazole, piperazine, N—$C_1$-$C_4$ alkylpiperazine, N-benzylpiperazine, N-phenylpiperazine, 2-pyridylpiperazine, or -A-NH—$R^{10}$, a point of attachment of $R^4$ to the —CH moiety of $G^1$ is an N-atom of $R^4$;

$R^1$ and $R^2$ are either (a) two independent groups or (b) together form a single ring group including the N to which they are bonded;

$R^1$ and $R^2$, when independent groups, are independently selected from the group consisting of: H, $C_1$-$C_4$ alkyl, $C_3$-$C_6$ cycloalkyl, allyl, and propargyl;

$R^1$ and $R^2$, when together form a single ring group including the N to which they are bonded, are selected from the group consisting of: piperazinyl, N—($C_1$-$C_4$ alkyl)-substituted piperazinyl, morpholino, and piperidinyl;

A is —NH—$(CH_2)_m$—CO— or an alpha amino acid residue;

m is 1, 2 or 3; and $R^9$ and $R^{10}$ are independently H, or $C_1$-$C_4$ alkyl.

Compounds of Formula III include compounds of Formula I wherein $G^1$ is $CH(R_4)CF_3$. Compounds Formula III may be further subdivided into three main subcategories, formula IIIA, formula IIIB and formula IIIC.

Compounds of formula IIIA are compounds of Formula III wherein $G^2$ is $C_1$-$C_4$ alkyl, or cyclopropyl; $G^3$ is H, or $C_1$-$C_4$ alkyl; and $R^4$ is selected from the group consisting of: $NR^1R^2$, imidazole, 1,2,4-triazole, piperazine, N—$C_1$-$C_4$ alkylpiperazine, N-benzylpiperazine, N-phenylpiperazine, 2-pyridylpiperazine and -A-NH—$R^{10}$.

Some embodiments of formula IIIA are compounds wherein $G^2$ is methyl.

Some embodiments of formula IIIA are compounds wherein $G^3$ is H and $G^4$ is H.

Some embodiments of formula IIIA are compounds wherein $R^4$ is $NR^1R^2$.

An example of a particular illustrative embodiment of Formula IIIA is a compound in which $G^4$ is H; $G^3$ is H, $G^2$ is methyl, $R^4$ is A-$NHR^{10}$, A is D-alanyl and $R^{10}$ is methyl. This compound may be termed N-methyl-$N^2$-[2,2,2-trifluoro-1-(3-hydroxy-1-methyl-4-oxo-1,4-dihydropyridin-2-yl)ethyl]-D-alaninamide and has the following structure:

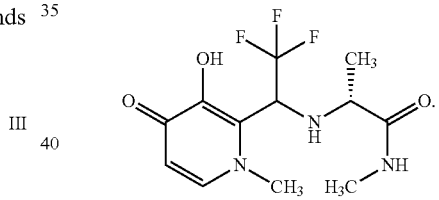

An example of a particular illustrative embodiment of Formula IIIA is a compound in which $G^4$ is H; $G^3$ is H, $G^2$ is methyl, $R^4$ is $NR^1R^2$, $R^1$ is methyl, and $R^2$ is methyl. This compound may be termed 2-[1-(dimethylamino)-2,2,2-trifluoroethyl]-3-hydroxy-1-methylpyridin-4(1H)-one and has the following structure:

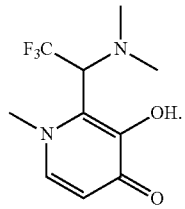

An example of a particular illustrative embodiment of Formula IIIA is a compound in which $G^4$ is H; $G^3$ is H, $G^2$ is methyl, $R^4$ is $NR^1R^2$, $R^1$ is methyl, and $R^2$ is propargyl. This compound may be termed 3-hydroxy-1-methyl-2-{2,2,2-trifluoro-1-[methyl(prop-2-yn-1-yl)amino]ethyl}pyridin-4(1H)-one and has the following structure:

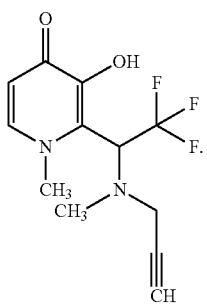 [SMILES: C#CCN(C)C(c1c(O)c(=O)ccn1C)C(F)(F)F]

An example of a particular illustrative embodiment of Formula IIIA is a compound in which $G^4$ is H; $G^3$ is H, $G^2$ is methyl, $R^4$ is $NR^1R^2$, R1 is H, $R^2$ is cyclopropyl. This compound may be termed 2-[1-(cyclopropylamino)-2,2,2-trifluoroethyl]-3-hydroxy-1-methylpyridin-4(1H)-one and has the following structure:

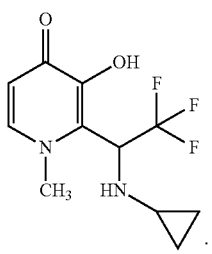 [SMILES: Cn1ccc(=O)c(O)c1C(NC1CC1)C(F)(F)F]

An example of a particular illustrative embodiment of Formula IIIA is a compound in which $G^4$ is H; $G^3$ is H, $G^2$ is methyl, $R^4$ is $NR^1R^2$, $R^1$ is H, $R^2$ is allyl. This compound may be termed 3-hydroxy-1-methyl-2-[2,2,2-trifluoro-1-(prop-2-en-1-ylamino)ethyl]pyridin-4(1H)-one and has the following structure:

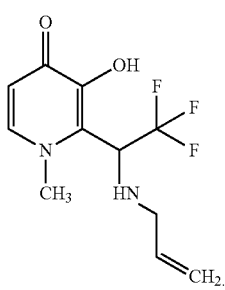 [SMILES: C=CCNC(c1c(O)c(=O)ccn1C)C(F)(F)F]

An example of a particular illustrative embodiment of Formula IIIA is a compound in which $G^4$ is H; $G^3$ is H, $G^2$ is methyl, $R^4$ is $NR^1R^2$, $NR^1R^2$ is piperidinyl. This compound may be termed 3-hydroxy-1-methyl-2-[2,2,2-trifluoro-1-(piperidin-1-yl)ethyl]pyridin-4(1H)-one and has the following structure:

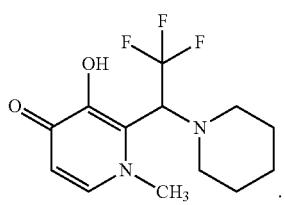

An example of a particular illustrative embodiment of Formula IIIA is a compound in which $G^4$ is H; $G^3$ is H, $G^2$ is methyl, $R^4$ is $NR^1R^2$, $NR^1R^2$ is N-methylpiperazinyl. This compound may be termed 3-hydroxy-1-methyl-2-[2,2,2-trifluoro-1-(4-methylpiperazin-1-yl)ethyl]pyridin-4(1H)-one and has the following structure:

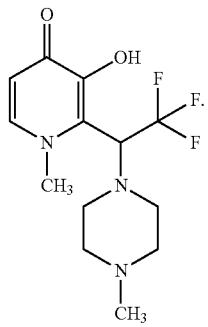 [SMILES: CN1CCN(C(c2c(O)c(=O)ccn2C)C(F)(F)F)CC1]

Compounds of formula IIIB are compounds of Formula III wherein G is $CH_2$-A-OH, $CH_2$-A-$NHR^9$, or $CH_2NR^1R^2$; $G^4$ is H, or $C_1$-$C_4$ alkyl; and $R^4$ is H, or OH.

Some embodiments of formula IIIB are compounds wherein $G^2$ is methyl.

Some embodiments of formula IIIB are compounds wherein $G^4$ is H.

An example of a particular illustrative embodiment of Formula IIIB is a compound in which $G^4$ is H; $G^3$ is $CH_2NR^1R^2$, $R^1$ is methyl, $R^2$ is methyl, $G^2$ is methyl, and $R^4$ is H. This compound may be termed 6-[(dimethylamino)methyl]-3-hydroxy-1-methyl-2-(2,2,2-trifluoroethyl)pyridin-4(1H)-one and has the following structure:

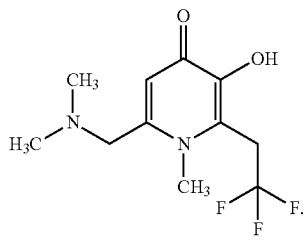 [SMILES: CN(C)Cc1cc(=O)c(O)c(CC(F)(F)F)n1C]

An example of a particular illustrative embodiment of Formula IIIB is a compound in which $G^4$ is H; $G^3$ is $CH_2NR^1R^2$, $R^1$ is methyl, $R^2$ is methyl, $G^2$ is methyl, and $R^4$ is OH. This compound may be termed 6-[(dimethylamino)methyl]-3-hydroxy-1-methyl-2-(2,2,2-trifluoro-1-hydroxyethyl)pyridin-4(1H)-one and has the following structure:

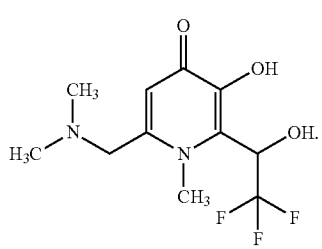 [SMILES: CN(C)Cc1cc(=O)c(O)c(C(O)C(F)(F)F)n1C]

An example of a particular illustrative embodiment of Formula IIIB is a compound in which $G^4$ is H; $G^3$ is $CH_2$-A-OH, A is L-alanyl, $G^2$ is methyl and $R^4$ is OH. This compound may be termed N-{[5-hydroxy-1-methyl-4-oxo- 6-(2,2,2-trifluoro-1-hydroxyethyl)-1,4-dihydropyridin-2-yl]methyl}-L-alanine and has the following structure:

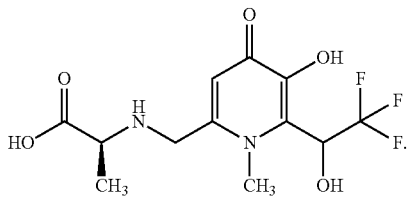 [SMILES: C[C@H](NCc1cc(=O)c(O)c(C(O)C(F)(F)F)n1C)C(=O)O]

An example of a particular illustrative embodiment of Formula IIIB is a compound in which $G^4$ is H; $G^3$ is $CH_2$-A-$NHR^9$, A is L-alanyl, $R^9$ is methyl, $G^2$ is methyl and $R^4$ is OH. This compound may be termed $N^2$-{[5-hydroxy-1-methyl-4-oxo-6-(2,2,2-trifluoro-1-hydroxyethyl)-1,4-dihydropyridin-2-yl]methyl}-N-methyl-L-alaninamide and has the following structure:

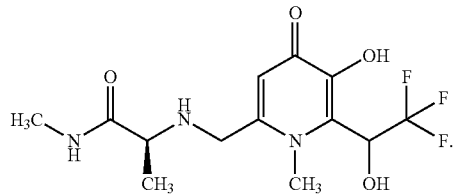

Compounds of formula IIIC are compounds of Formula III wherein $G^3$ is H or $C_1$-$C_4$ alkyl; and $G^4$ is halo.

Some embodiments of formula IIIC are compounds wherein $G^2$ is methyl.

Some embodiments of formula IIIC are compounds wherein $G^4$ is chloro.

An example of a particular illustrative embodiment of Formula IIIC is a compound in which $G^4$ is chloro, $G^3$ is methyl, $G^2$ is methyl, and $R^4$ is OH. This compound may be termed 3-chloro-5-hydroxy-1,2-dimethyl-6-(2,2,2-trifluoro-1-hydroxyethyl)pyridin-4(1H)-one and has the following structure:

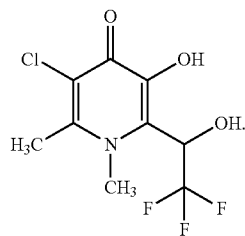

An example of a particular illustrative embodiment of Formula IIIC is a compound in which $G^4$ is chloro, $G^3$ is methyl, $G^2$ is methyl, and $R^4$ is H. This compound may be termed 3-chloro-5-hydroxy-1,2-dimethyl-6-(2,2,2-trifluoroethyl)pyridin-4(1H)-one and has the following structure:

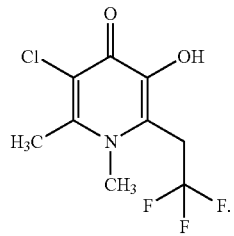

An example of a particular illustrative embodiment of Formula IIIC is a compound in which $G^4$ is chloro, $G^3$ is methyl, $G^2$ is methyl, $R^4$ is $NR^1R^2$, $R^1$ is methyl and $R^2$ is methyl. This compound may be termed 3-chloro-6-[1-(dimethylamino)-2,2,2-trifluoroethyl]-5-hydroxy-1,2-dimethylpyridin-4(1H)-one and has the following structure:

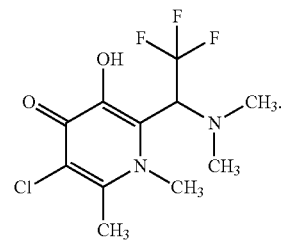 [SMILES: Cc1c(Cl)c(=O)c(O)c(C(N(C)C)C(F)(F)F)n1C]

An example of a particular illustrative embodiment of Formula IIIC is a compound in which $G^4$ is chloro, $G^3$ is H, $G^2$ is methyl, $R^4$ is $NR^1R^2$, $R^1$ is methyl and $R^2$ is methyl. This compound may be termed 5-chloro-2-[1-(dimethylamino)-2,2,2-trifluoroethyl]-3-hydroxy-1-methylpyridin-4(1H)-one and has the following structure:

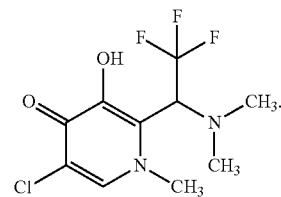 [SMILES: CN(C)C(c1c(O)c(=O)c(Cl)cn1C)C(F)(F)F]

An example of a particular illustrative embodiment of Formula IIIC is a compound in which $G^4$ is chloro, $G^3$ is H, $G^2$ is methyl, $R^4$ is $NR^1R^2$, and $NR^1R^2$ is piperidinyl. This compound may be termed 5-chloro-3-hydroxy-1-methyl-2-[2,2,2-trifluoro-1-(piperidin-1-yl)ethyl]pyridin-4(1H)-one and has the following structure:

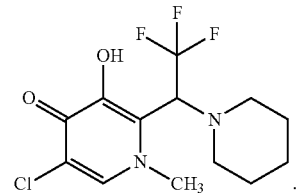 [SMILES: Cn1cc(Cl)c(=O)c(O)c1C(N1CCCCC1)C(F)(F)F]

An example of a particular illustrative embodiment of Formula IIIC is a compound in which $G^4$ is chloro, $G^3$ is H, $G^2$ is methyl, $R^4$ is H. This compound may be termed 5-chloro-3-hydroxy-1-methyl-2-(2,2,2-trifluoroethyl)pyridin-4(1H)-one and has the following structure:

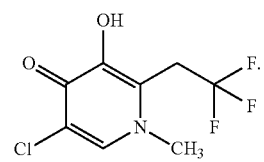

Some embodiments of Formula I provide compounds having a structure of Formula IV

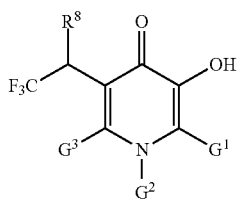

IV

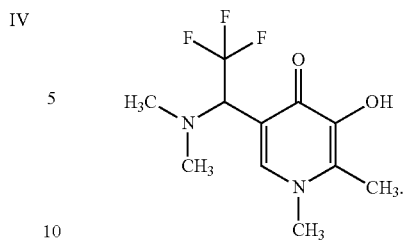

wherein

G¹ is H, or C₁-C₄ alkyl;

G² is H, C₁-C₄ alkyl, or cyclopropyl;

G³ is H, or C₁-C₄ alkyl;

R⁸ is selected from the group consisting of: NR¹R², imidazole, 1,2,4-triazole, piperazine, N—C₁-C₄ alkylpiperazine, N-benzylpiperazine, 2-pyridylpiperazine, and -A-NH—R¹⁰; a point of attachment of R⁸ to the —CH moiety of G¹ is an N-atom of R⁸;

R¹ and R² are either (a) two independent groups or (b) together form a single ring group including the N to which they are bonded;

R¹ and R², when independent groups, are independently selected from the group consisting of: H, C₁-C₄ alkyl, C₃-C₆ cycloalkyl, allyl, and propargyl;

R¹ and R², when together form a single ring group including the N to which they are bonded, are selected from the group consisting of: piperazinyl, N—(C₁-C₄ alkyl)-substituted piperazinyl, morpholino, and piperidinyl;

A is —NH—(CH₂)ₘ—CO— or an alpha amino acid residue;

m is 1, 2 or 3; and

R¹⁰ is H, or C₁-C₄ alkyl.

Some embodiments of Formula IV are compounds wherein G³ is H.

Some embodiments of Formula IV are compounds wherein G¹ is methyl.

An example of a particular illustrative embodiment of Formula IV is a compound in which G³ is H; G¹ is methyl, G² is H, R⁸ is A-NHR¹⁰, A is L-alanyl, and R¹⁰ is methyl. This compound may be termed N-methyl-N²-[2,2,2-trifluoro-1-(5-hydroxy-6-methyl-4-oxo-1,4-dihydropyridin-3-yl)ethyl]-alaninamide and has the following structure:

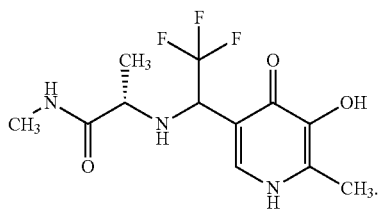 [SMILES: CNC(=O)[C@H](C)NC(c1c[nH]c(C)c(O)c1=O)C(F)(F)F]

An example of a particular illustrative embodiment of Formula IV is a compound in which G³ is H; G¹ is methyl, G² is methyl, R⁸ is NR¹R²; R¹ is methyl, and R² is methyl. This compound may be termed 5-[1-(dimethylamino)-2,2,2-trifluoroethyl]-3-hydroxy-1,2-dimethylpyridin-4(1H)-one and has the following structure:

An example of a particular illustrative embodiment of Formula IV is a compound in which G³ is H; G¹ is methyl, G² is methyl, R⁸ is NR¹R²; R¹ is H, and R² is methyl. This compound may be termed 3-hydroxy-1,2-dimethyl-5-[2,2,2-trifluoro-1-(methylamino)ethyl]pyridin-4(1H)-one and has the following structure:

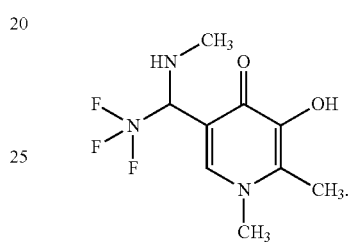

An example of a particular illustrative embodiment of Formula IV is a compound in which G³ is H; G¹ is methyl, G² is methyl, R⁸ is NR¹R²; NR¹R² is piperidinyl. This compound may be termed 3-hydroxy-1,2-dimethyl-5-[2,2,2-trifluoro-1-(piperidin-1-yl)ethyl]pyridin-4(1H)-one and has the following structure:

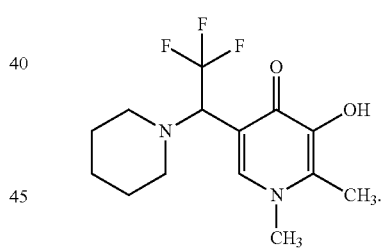

An example of a particular illustrative embodiment of Formula IV is a compound in which G³ is H; G¹ is methyl, G² is methyl, R⁸ is NR¹R²; NR¹R² is imidazolyl. This compound may be termed 3-hydroxy-1,2-dimethyl-5-[2,2,2-trifluoro-1-(1H-imidazol-1-yl)ethyl]pyridin-4(1H)-one and has the following structure:

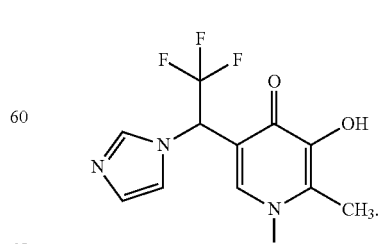

An example of a particular illustrative embodiment of Formula IV is a compound in which $G^3$ is H; $G^1$ is methyl, $G^2$ is methyl, $R^8$ is $NR^1R^2$; and $NR^1R^2$ is N-methylpiperazinyl. This compound may be termed 3-hydroxy-1,2-dimethyl-5-[2,2,2-trifluoro-1-(4-methylpiperazin-1-yl)ethyl]pyridin-4(1H)-one hydrochloride and has the following structure:

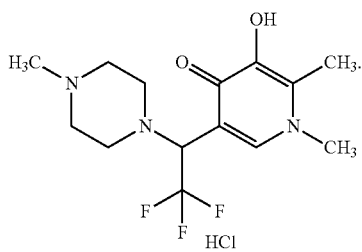

Some embodiments of Formula I provide compounds having a structure of Formula V

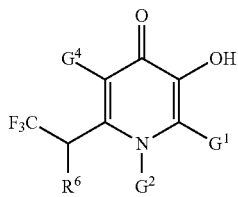

wherein $G^1$ is $CH_2NR^1R^2$, or $NR^1R^2$;
$G^2$ is $C_1$-$C_4$ alkyl, or cyclopropyl;
$G^4$ is H, or $C_1$-$C_4$ alkyl;
$R^6$ is H, or OH; and
$R^1$ and $R^2$ are either (a) two independent groups or (b) together form a single ring group including the N to which they are bonded;
$R^1$ and $R^2$, when independent groups, are independently selected from the group consisting of: H, $C_1$-$C_4$ alkyl, $C_3$-$C_6$ cycloalkyl, allyl, and propargyl;
$R^1$ and $R^2$, when together form a single ring group including the N to which they are bonded, are selected from the group consisting of: piperazinyl, N—($C_1$-$C_4$ alkyl)-substituted piperazinyl, morpholino, and piperidinyl.

Some embodiments of Formula V are compounds wherein $G^4$ is H.

Some embodiments of Formula V are compounds wherein $G^2$ is methyl.

An example of a particular illustrative embodiment of Formula V is a compound in which $G^4$ is H; $R^6$ is H, $G^2$ is methyl, $G^1$ is $NR^1R^2$, $R^1$ is methyl and $R^2$ is methyl. This compound may be termed 2-(dimethylamino)-3-hydroxy-1-methyl-6-(2,2,2-trifluoroethyl)pyridin-4(1H)-one

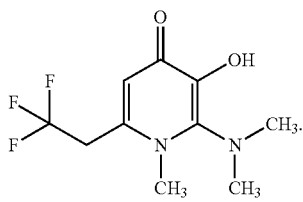

An example of a particular illustrative embodiment of Formula V is a compound in which $G^4$ is H; $R^6$ is OH, $G^2$ is methyl, $G^1$ is $CH_2NR^1R^2$, $R^1$ is methyl and $R^2$ is methyl, $R^1$ is methyl and $R^2$ is methyl. This compound may be termed 2-[(dimethylamino)methyl]-3-hydroxy-1-methyl-6-(2,2,2-trifluoro-1-hydroxyethyl)pyridin-4(1H)-one

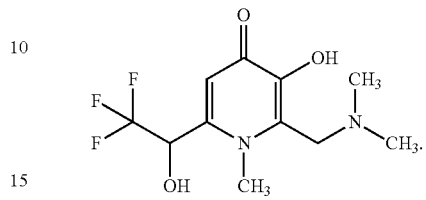

Some embodiments of Formula I provide compounds having a structure of Formula VI:

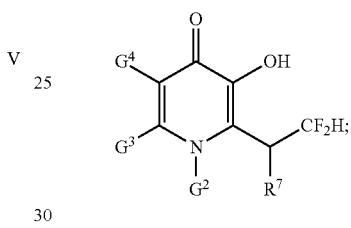

wherein $G^2$ is H, $C_1$-$C_4$ alkyl, or cyclopropyl;
$G^3$ is H, or $C_1$-$C_4$ alkyl;
$G^4$ is H, or $C_1$-$C_4$ alkyl;
$R^7$ is selected from the group consisting of: H, OH, $NR^1R^2$, imidazolyl, 1,2,4-triazolyl, piperazinyl, N—$C_1$-$C_4$ alkylpiperazinyl, N-benzylpiperazinyl, N-phenylpiperazinyl, 2-pyridylpiperazinyl, and —$CH_2$-A-NH—$R^{10}$; and when $R^7$ is $NR^1R^2$, imidazolyl, 1,2,4-triazolyl, piperazinyl, alkylpiperazinyl, N-benzylpiperazinyl, N-phenylpiperazinyl, 2-pyridylpiperazinyl or —$CH_2$-A-NH—$R^{10}$, a point of attachment of $R^7$ to the —CH moiety of $G^1$ is an N-atom of $R^7$;
$R^1$ and $R^2$ are either (a) two independent groups or (b) together form a single ring group including the N to which they are bonded;
$R^1$ and $R^2$, when independent groups, are independently selected from the group consisting of: H, $C_1$-$C_4$ alkyl, $C_3$-$C_6$ cycloalkyl, allyl, and propargyl;
$R^1$ and $R^2$, when together form a single ring group including the N to which they are bonded, are selected from the group consisting of: piperazinyl, N—($C_1$-$C_4$ alkyl)-substituted piperazinyl, morpholino, and piperidinyl;
A is —NH—$(CH_2)_m$—CO— or an alpha amino acid residue;
m is 1, 2 or 3; and
$R^{10}$ is H, $C_1$-$C_4$ alkyl.

An example of a particular illustrative embodiment of Formula VI is a compound in which $G^3$ is H, $G^4$ is H, $G^2$ is methyl, $G^1$ is $CH(R^7)CF_2H$, and $R^7$ is hydroxy. This compound may be termed 2-(2,2-difluoro-1-hydroxyethyl)-3-hydroxy-1-methylpyridin-4(1H)-one and has the following structure:

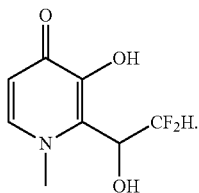

Another example of a particular illustrative embodiment of Formula VI is a compound in which $G^3$ is H, $G^4$ is H, $G^2$ is methyl, $G^1$ is $CH(R^7)CF_2H$, and $R^7$ is H. This compound may be termed 2-(2,2-difluoroethyl)-3-hydroxy-1-methyl-pyridin-4(1H)-one and has the following structure:

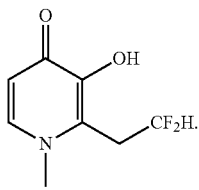

Some embodiments of Formula I provide compounds having a structure of Formula VII:

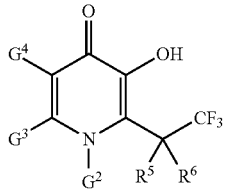

wherein
$G^2$ is H, $C_1$-$C_4$ alkyl, or cyclopropyl;
$G^3$ is H, or $C_1$-$C_4$ alkyl; and
$G^4$ is H, or $C_1$-$C_4$ alkyl.

Particular illustrative embodiments of Formula VII include compounds in which $G^2$ is methyl, $G^3$ is H, $G^4$ is H, $R^5$ is methyl, and $R^6$ is H or OH. An example of a particular illustrative embodiment of Formula VII is a compound in which $G^2$ is methyl, $G^3$ is H, $G^4$ is H, $R^5$ is methyl, and $R^6$ is OH. This compound may be termed 3-hydroxy-1-methyl-2-(1,1,1-trifluoro-2-hydroxypropan-2-yl)pyridin-4(1H)-one and has the following structure:

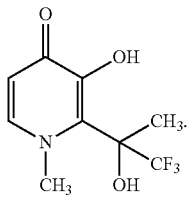

In some embodiments, compounds of the present invention comprise a 3-hydroxypyridin-4-one moiety having a halo group, attached to the $C_5$ position of the ring ($G^4$ is halo), and a trifluoroethyl moiety, at the $G^1$ or $G^2$ or $G^3$ position. In some of these embodiments, the halo group is a chloro group.

The following Schemes 1-9 depict examples of methods that can be used for the preparation of compounds of the Formulas I, II, III, IV, V, VI, and VII. All of the starting materials are prepared by procedures described in these schemes, by procedures well known to one of ordinary skill in organic chemistry or can be obtained commercially. All of the final compounds of the present invention may be prepared by procedures described in these schemes or by procedures analogous thereto.

Scheme 1

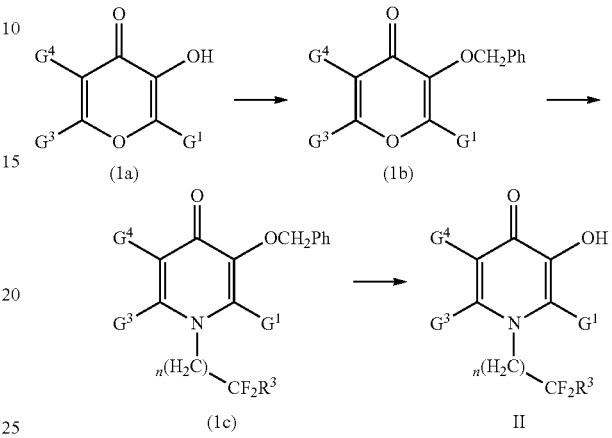

The compounds of Formula I wherein $G^2$=—$(CH_2)_n$$CF_2R^3$ can be prepared by the method as shown in Scheme 1, or by the methods given in the examples or by analogous methods. As shown in Scheme 1, compound (1a) wherein $G^1$ is H or $C_1$-$C_4$ alkyl, $G^3$ is H or $C_1$-$C_4$ alkyl, $G^4$ is H or $C_1$-$C_4$ alkyl, may be treated with sodium hydroxide and benzyl bromide or benzyl chloride to give the compound (1b). The amine insertion with compound (1b) may be conducted with trifluoroethylamine hydrochloride and an organic base such as pyridine in an inert solvent to give compound (1c) wherein n is 1 and $R^3$ is F, which may be deprotected either by hydrolysis with hydrochloric acid solution or by catalytic hydrogenation over 10% Pd/C to give a compound of formula II. Compound of formula II is a compound of Formula I wherein $R^3$ is F, and n is 1.

As an illustrative example, the compounds of Formula I wherein $G^1$ is H, $G^3$ is H, $G^4$ is H, n is 1, $R^3$ is F can be prepared by the method shown in Scheme 2.

Scheme 2

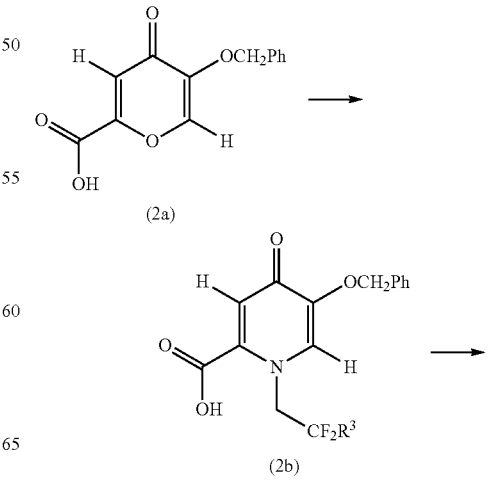

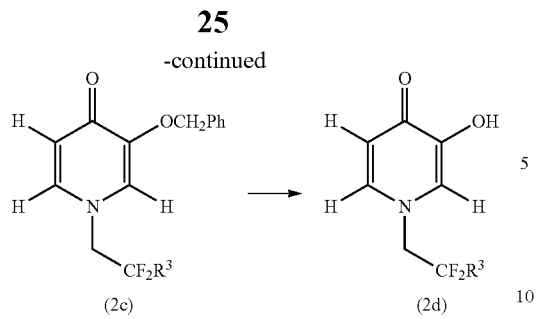

Compound (2a) may be reacted with $CF_2R^3CH_2NH_2$ in water to give a compound (2b), which upon heating in inert organic solvent such as dimethylformamide, affords the compound (2c), which may be deprotected with catalytic hydrogenation using hydrogen, catalytic palladium on charcoal to give a compound (2d), which is compound of Formula II wherein n is 1, $G^1$ is H, $G^3$ is H, $G^4$ is H. Compound (2d) is also a compound of formula I wherein $G^1$ is H, $G^3$ is H, $G^4$ is H, n is 1, $G^2$ is $-CH_2CF_2R^3$.

The compounds of Formula I wherein n is 1, $G^2$ is $CH_2CF_2R^3$, $G^1$ is $CH_2NR^1R^2$, $CH_2OH$, or a compound of formula II wherein $G^1$ is $CH_2OH$ or $CH_2NR^1R^2$ are prepared by the method as shown in Scheme 3.

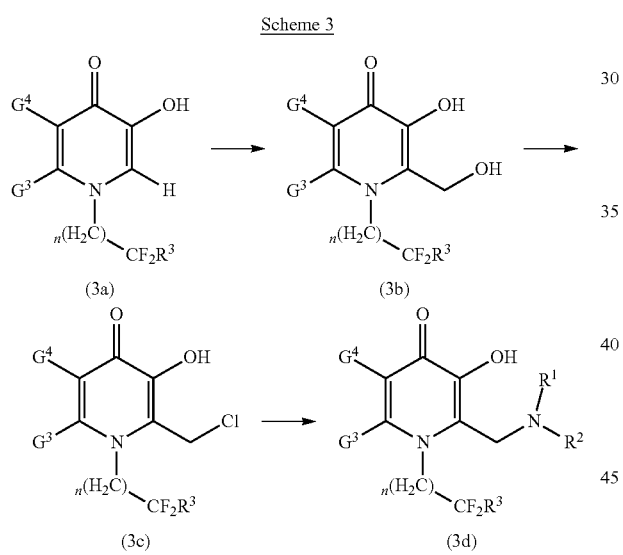

Compound (3a) may be reacted with formaldehyde and sodium hydroxide to give compound (3b). Reaction of compound (3b) with thionyl chloride in an inert solvent such as acetonitrile affords the chloro compound (3c), which may be quenched with an amine $R^1R^2NH$ to give the compound of Formula (3d), which is a compound of Formula I when $G^1$ is $CH_2NR^1R^2$. The compound may be isolated by conventional means. Alternatively, when n=1, compound (3a) may be reacted directly with bis-(dimethylamino)methane to give the compound (3d), which is a compound of Formula I wherein $G^1$ is $CH_2N(CH_3)_2$.

The compounds of Formula I wherein $G^1$ is $CH(R^4)CF_3$, $R^4$ is $NR^1R^2$, OH, H or the compounds of Formula III wherein $R^4$ is $NR^1R^2$, OH, H; $G^2$ is H, $C_1$-$C_4$ alkyl; $G^3$ is H, $C_1$-$C_4$ alkyl; $G^4$ is H, $C_1$-$C_4$ alkyl, halo; may be prepared by the method as shown in Scheme 4. For illustration purposes, the scheme shows the synthesis of a compound of Formula I or IIIA or IIIC wherein $G^3$ is H.

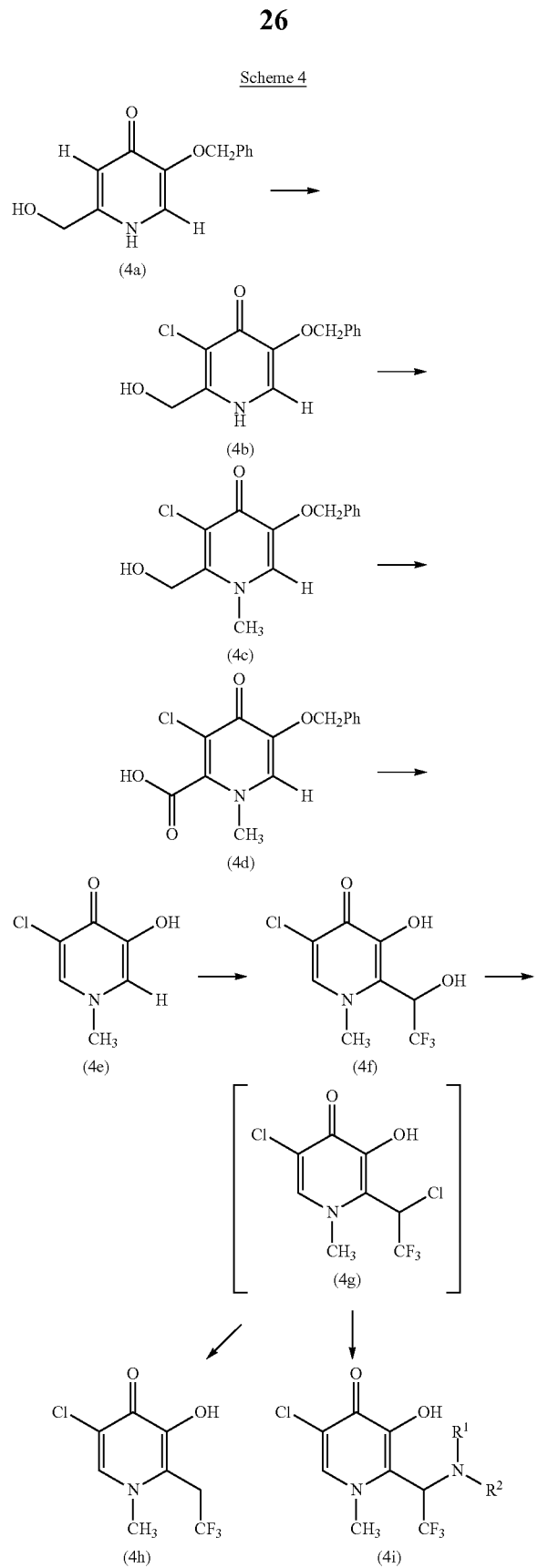

Compound (4a) may be reacted with sodium hypochlorite in 2N NaOH to give the chloro derivative (4b), which may then be reacted with potassium carbonate and methyl iodide in dimethylformamide to give the N-methyl compound (4c). TEMPO oxidation in an inert solvent such as acetone affords the carboxylic acid (4d). Acid deprotection and decarboxylation with 6N hydrochloric acid affords the starting material (4e). Compound (4e) may be reacted with $CF_3CH(OCH_3)OH$ to give the diol (4f). Treatment of thionyl chloride and pyridine yields the chloride (4g). Upon reacting compound (4g) with sodium borohydride, compound (4h) may be formed. Compound (4i) is obtained from the quenching of the chloride (4g) with $R^1R^2NH$.

Compound (4i) is a compound of Formula I wherein $G^1$ is $CH(R^4)CF^3$, $R^4$ is $NR^1R^2$ wherein $R^1$, $R^2$ are methyl, $G^2$ is methyl, $G^3$ is H, and $G^4$ is chloro. It is also a compound of formula III wherein $R^4$ is $NR^1R^2$ wherein $R^1$, $R^2$ are methyl, $G^2$ is methyl, $G^3$ is H, and $G^4$ is chloro.

Compound (4h) is a compound of Formula I wherein $G^1$ is $CH(R^4)CF_3$, $R^4$ is H, $G^2$ is methyl, $G^3$ is H, $G^4$ is chloro. It is also a compound of formula III wherein $R^4$ is H, $G^2$ is methyl, $G^3$ is H, $G^4$ is chloro.

Compound (4f) is a compound of Formula I wherein $G^1$ is $CH(R^4)CF_3$, $R^4$ is OH, $G^2$ is methyl, $G^3$ is H, $G^4$ is chloro. It is also a compound of formula III wherein $R^4$ is OH, $G^2$ is methyl, $G^3$ is H, $G^4$ is chloro.

The compound of Formula I wherein $G^4$ is $CH(R^8)CF_3$, $R^8$ is $NR^1R^2$, $G^3$ is H, $G^1$ is $C_1$-$C_4$ alkyl, $G^2$ is $C_1$-$C_4$ alkyl or the compound of formula IV wherein $R^8$ is $NR^1R^2$, $G^3$ is H, $G^1$ is methyl, $G^2$ is methyl may be prepared according to the representative procedures as outline in Scheme 5 below:

Scheme 5

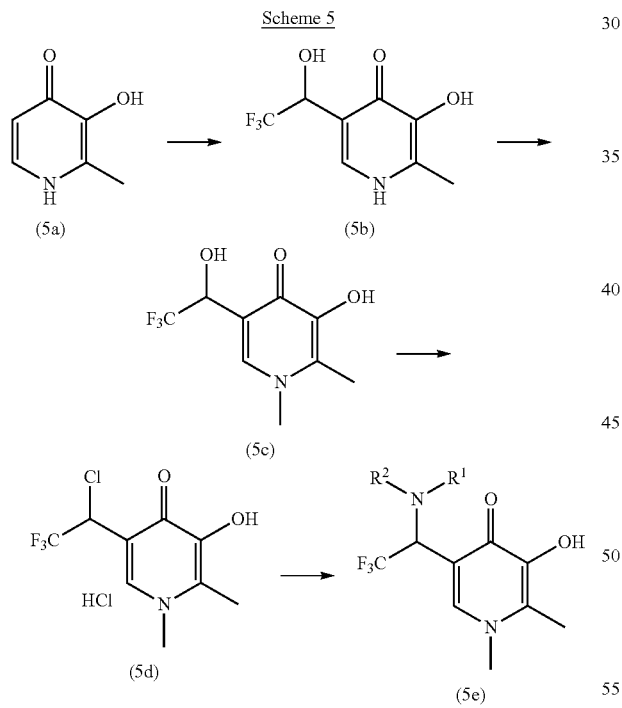

Compound (5c) may be prepared according to the procedure outlined in WO20080242706. Reaction of compound (5c) with thionyl chloride gives (5d) which may be quenched with an amine $R^1R^2NH$ to give compound (5e). Compound (5e) is a compound of Formula I wherein $G^4$=$CH(R^8)CF_3$, $R^8$ is $NR^1R^2$, $G^3$ is H, $G^1$ is methyl, $G^2$ is methyl. It is also a compound formula IV wherein $R^8$ is $NR^1R^2$, $G^3$ is H, $G^1$ is methyl, $G^2$=methyl. When $R^1$ is methyl, $R^2$ is methyl, compound (5e) has the chemical name 5-[1-(dimethylamino)-2,2,2-trifluoroethyl]-3-hydroxy-1,2-dimethylpyridin-4(1H)-one.

A compound of Formula I wherein $G^1$ is $CH(R^4)CF_3$, $R^4$ is H or OH, $G^2$ is $C_1$-$C_4$ alkyl, $G^3$ is $CH_2NR^1R^2$, $G^4$ is H or a compound of formula IIIB wherein $R^4$ is H or OH, $G^2$ is methyl, $G^3$ is $CH_2NMe_2$, $G^4$ is H may be prepared according to the representative procedures as outline in Scheme 6 below:

Scheme 6

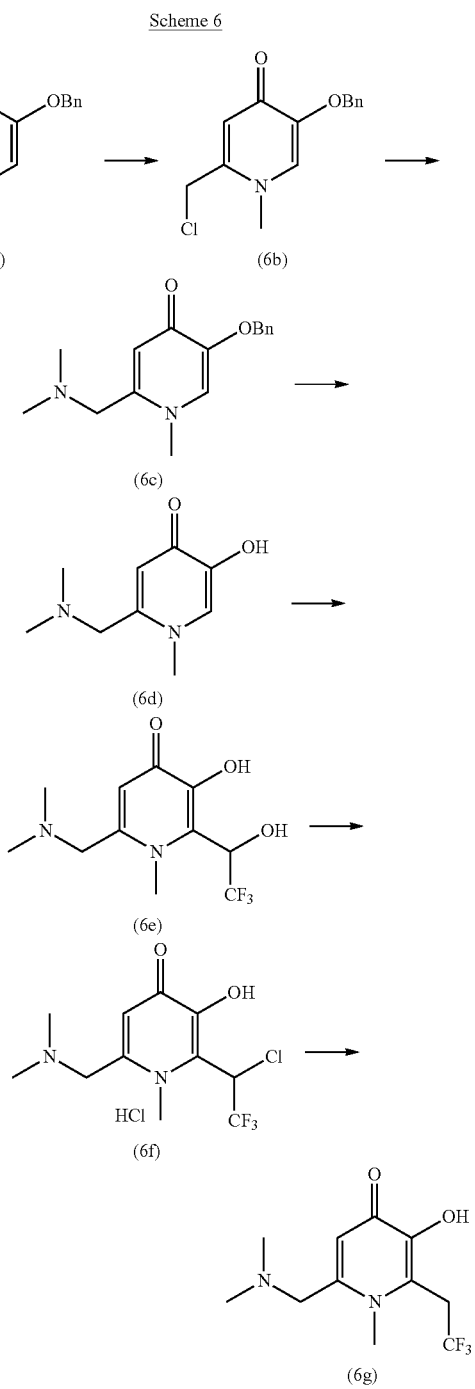

Alcohol (6a) may be converted to the chloro compound (6b) with thionyl chloride. Upon quenching with dimethylamine, compound (6c) is formed, which may be deprotected by catalytic hydrogenation with palladium on charcoal to give compound (6d). Reaction of compound (6d) with $CF_3CH(OH)OCH_3$ and potassium carbonate affords the diol (6e), which reacts with thionyl chloride to give the compound (6f). Reduction of the chloro compound with catalytic hydrogenation yields the compound (6g). Compound (6e) is a compound of Formula I wherein $G^4$ is H, $G^3$ is $CH_2NR^1R^2$, $R^1$ is methyl, $R^2$ is methyl, $G^2$ is methyl, $G^1$ is $CH(R^4)CF_3$, $R^4$ is OH. It is also a compound of formula IIIB wherein $G^4$ is H, $G^3$ is $CH_2NR^1R^2$, $R^1$ is methyl, $R^2$ is methyl, $G^2$ is methyl, $R^4$ is OH. Compound (6e) has the chemical name 6-[(dimethylamino)methyl]-3-hydroxy-1-methyl-2-(2,2,2-trifluoro-1-hydroxyethyl)pyridin-4(1H)-one.

Compound (6g) is a compound of Formula I wherein $G^4$ is H, $G^3$ is $CH_2NR^1R^2$, $R^1$ is methyl, $R^2$ is methyl, $G^2$ is methyl, $G^1$ is $CH(R^4)CF_3$, $R^4$ is H. It is also a compound of formula IIIB wherein $G^4$=H, $G^3$=$CH_2NR^1R^2$, $R^1$ is methyl, $R^2$ is methyl, $G^2$ is methyl, $G^1R^4$ is H. Compound (6e) has the chemical name 6-[(dimethylamino)methyl]-3-hydroxy-1-methyl-2-(2,2,2-trifluoroethyl)pyridin-4(1H)-one.

A compound of Formula I wherein $G^3$ is H or $C_1$-$C_4$ alkyl; $G^4$ is H, or $C_1$-$C_4$ alkyl; $G^1$ is $CH(R^7)CF_2H$, or a compound of formula VI wherein $G^3$ is H or $C_1$-$C_4$ alkyl; $G^4$ is H, or $C_1$-$C_4$ alkyl; $R^7$ is H, OH, $NR^1R^2$ may be prepared according to the representative procedures as outline in Scheme 7 below:

pound of Formula (7b). This intermediate may be converted to compounds (7e) and (7d) in a similar manner as described for the conversion of compound (4f) to (4h) and (4i) (Scheme 4). (7b) is a compound of Formula I wherein $G^1$ is $CH(R^7)CF_2H$, $R^7$ is OH or a compound of formula VI wherein $R^7$ is OH. (7e) is a compound of Formula I wherein $R^7$ is H, or a compound of formula VI wherein $R^7$ is H and (7d) is a compound of Formula I wherein $G^1$ is $CH(R^7)CF_2H$, $R^7$ is $NR^1R^2$ or a compound of formula VI wherein $R^7$ is $NR^1R^2$. For example, when $G^2$ is methyl, $G^3$ is H, $G^4$ is H in scheme 1, the compound (7e) is 2-(2,2-difluoroethyl)-3-hydroxy-1-methylpyridin-4(1H)-one and the compound (7b) is 2-(2,2-difluoro-1-hydroxyethyl)-3-hydroxy-1-methylpyridin-4(1H)-one.

The compound of Formula I wherein $G^3$ is $CH(R^6)CF_3$, $R^6$ is H, $G^1$ is $NR^1R^2$ or a compound of formula V wherein $R^6$ is H, $G^3$ is $CH_2CF_3$, $G^1$ is $NR^1R^2$ may be prepared according to the representative procedures as outline in Scheme 8 below:

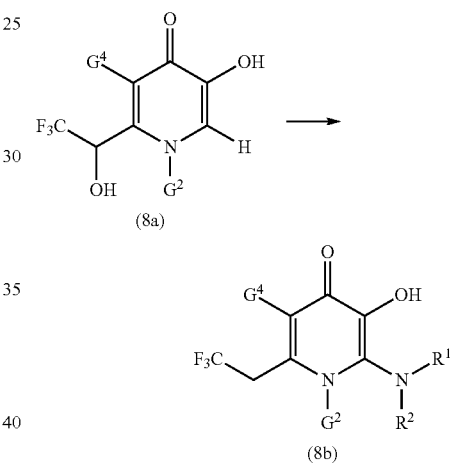

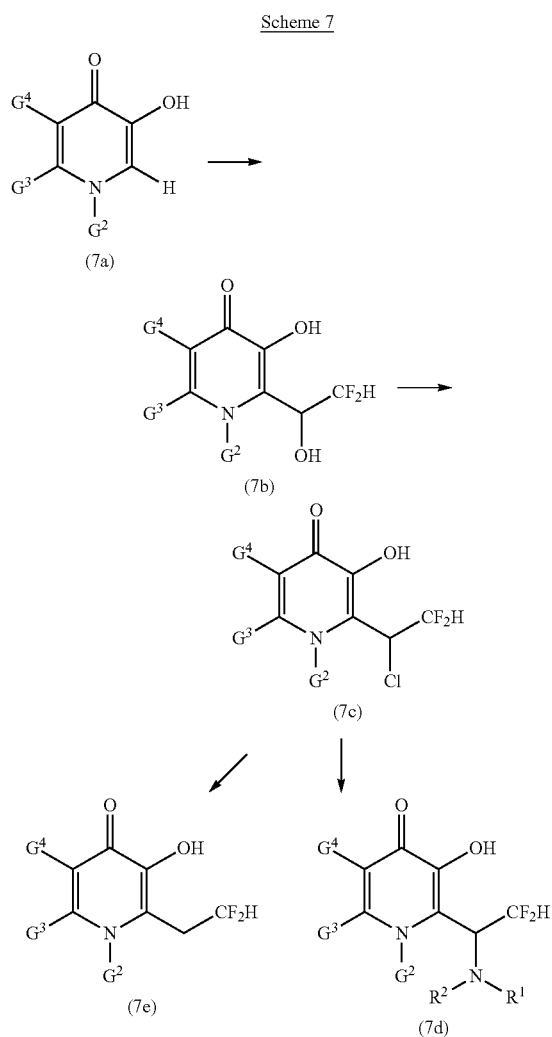

Compound (7a) may be reacted with difluoroacetaldehyde ethyl hemiacetal and potassium carbonate to give the com- Compound (8a) wherein $G^2$ is $C_1$-$C_4$ alkyl, $G^4$ is H may be first reacted with thionyl chloride in an inert solvent. Quenching the reaction with an amine $R^1R^2NH$ affords the compound (8b). The structure of (8b) may be confirmed by NMR and MS spectroscopy. The compound of Formula (8b) is a compound of Formula I wherein $G^2$ is $C_1$-$C_4$ alkyl, $G^4$ is H, or $C_1$-$C_4$ alkyl, $R^6$ is H; or a compound of formula V wherein $R^6$ is H, $G^2$ is $C_1$-$C_4$ alkyl, $G^1$ is $NR^1R^2$, $G^4$ is H. For example, the compound 5-hydroxy-1-methyl-2-(2,2,2-trifluoro-1-hydroxyethyl)pyridin-4(1H)-one is a compound (8a) wherein $G^4$ is H, $G^2$ is methyl. Compound (8a) can be converted to 2-(dimethylamino)-3-hydroxy-1-methyl-6-(2,2,2-trifluoroethyl)pyridin-4(1H)-one, a compound of (8b) wherein $R^1$ is methyl, $R^2$ is methyl, $G^2$ is methyl, $G^4$ is hydrogen with dimethylamine according to the method described in Scheme 8.

Compound of Formula I wherein $G^1$ is $C(R^5)(R^6)CF_3$, $R^5$ is $C_1$-$C_4$ alkyl, $R^6$ is OH or a compound of formula VII wherein $R^5$ is $C_1$-$C_4$ alkyl, $R^6$ is OH may be prepared according to the representative procedures as shown in Scheme 9 below:

Scheme 9

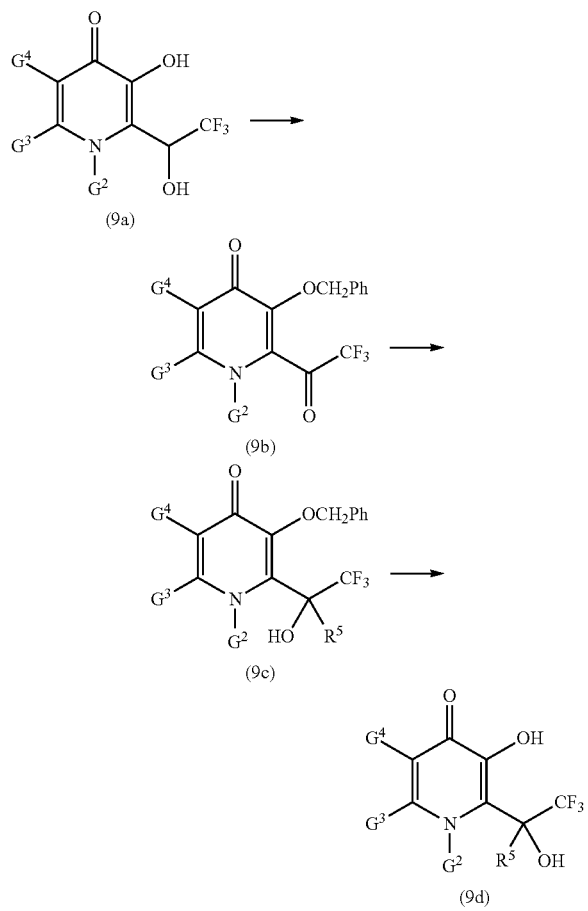

Compound (9a) may be first reacted with Dess-Martin oxidation reagent to give compound 9b, which may be reacted with the Grignard reagent $R^5$—MgCl or $R^5$—MgBr to give compound 9c. Catalytic hydrogenation of 13 with palladium on charcoal affords compound 9d, which is a compound of Formula I when $R^5$ is $C_1$-$C_4$ alkyl, $R^6$ is OH. For example, in when $G^2$ is methyl, $G^3$ is H, $G^4$ is H, $R^5$ is methyl in Scheme 9, the product (9d) is the compound 3-hydroxy-1-methyl-2-(1,1,1-trifluoro-2-hydroxypropan-2-yl)pyridin-4(1H)-one.

Many compounds of this invention or for use in this invention may be formed as salts. In such cases, pharmaceutical compositions in accordance with this invention may comprise a salt of such a compound, preferably a physiologically acceptable salt, which are known in the art. Pharmaceutical preparations will typically comprise one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in Remington: the Science & Practice of Pharmacy by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition according to the invention includes a therapeutically effective amount or a prophylactically effective amount. A "therapeutically effective amount" refers to an amount effective, at dosages and for periods of time necessary, to achieve the desired therapeutic result, such as improved iron distribution or reduced levels of toxic iron. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as such as improved iron distribution or reduced levels of toxic iron. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

As used herein, a "subject" may be a human, non-human primate, rat, mouse, cow, horse, pig, sheep, goat, dog, cat, etc. The subject may be suspected of having or at risk for having a medical condition related to a toxic concentration of iron. The medical condition related to a toxic concentration of iron may be selected from the group consisting of: cancer, pulmonary disease, progressive kidney disease and Friedreich's ataxia. Diagnostic methods for various medical conditions related to a toxic concentration of iron and the clinical delineation of various medical conditions related to a toxic concentration of iron and their diagnoses are known to those of ordinary skill in the art.

An important property of iron is its ability to donate and accept an electron readily between the ferrous ($Fe^{2+}$) and ferric ($Fe^{3+}$) species. This can be a liability as iron can play a critical role in both the Fenton and the Haber-Weiss reactions in catalyzing the production of hydroxyl radicals. Thus, in conditions wherein the reduction of Fe(III) to Fe(II) is facilitated, the generation of these active oxygen species (hydroxyl radical) can cause considerable damage to biomolecules in the living system that include cellular membranes, proteins and DNA.

  (reduction of metal)

  (Fenton reaction)

  (Haber-Weiss cycle)

Iron chelators can either inhibit or facilitate the participation of iron in the Fenton and Haber-Weiss reactions that produce toxic oxygen radicals. Since certain iron chelators can potentially promote $Fe^{3+}$ reduction, early evaluations on whether the chelator can promote, prevent, or has no effect on $Fe^{3+}$ reduction are essential.

There are several quintessential methods and chemical models that have been used to study the capacity of the chelators to restrict the participation of iron in radical generating reactions via the indirect observation of radical formation (Dean R T and Nicholson P (1994) Free Radical Res 20:83-101 and Gutteridge J M (1990) Free Radical Res Commun 9:119-125). The use of cyclic voltammetry, and benzoic acid hydroxylation assay in screening the compounds of formula I are illustrated in the examples 30 and 31, respectively.

The neuroprotective effect of compounds of formula I is demonstrated in the hydrogen peroxide induced apoptosis in SH-SY5Y neuroblastoma cells assay in example 32A. The protective effective of compounds of formula I against endogenously produced Aβ toxicity is shown in example 32B. Cytotoxicity was also induced by the dopaminergic neurotoxin $MPP^+$ on SV-NRA cells. The neuroprotective action of selected compounds of formula I is further demonstrated in $MPP^+$ treated SV-NRA cells in Example 33 below.

In-vivo pharmacokinetic (PK) and blood brain barrier (BBB) studies were conducted in male Sprague-Dawley rats using cassette dosing via oral administration. The topic of cassette dosing has been reviewed by Manitpisitkul, P. and White, R. E. (August 2004), Drug Discovery, Vol 9. No. 15, pp. 652-658. The results are summarized in the Table below:

| Oral Cassette Dosing Studies of a compound of formula I in male Sprague-Dawley rats, AUCs is normalized to 1 mg/kg dose | | | | |
|---|---|---|---|---|
| Cpd | AUC brain* (ug-h/mL) | AUC plasma* (ug-h/mL) | AUC brain/AUC plasma | CL (L/h-kg) |
| Apo6995 | 0.30 | 0.26 | 1.2 | 3.89 |
| Apo7030 | 0.59 (cal.) | 0.59 | 1.00 | 1.68 |
| Apo7041 | 0.45 | 0.60 | 0.75 | 1.67 |
| Apo7080 | 0.7 | 0.92 | 0.76 | 1.09 |
| Apo7067 | 0.74 | 0.5 | 1.50 | 2.00 |
| Apo7056 | 0.77 | 1.38 | 0.56 | 0.72 |
| Clioquinol | 0.042 | 0.028 | 1.5 | 3.52 |

List of Compounds of Formula I Tested in Cassette Dosing BBB Studies

| Cpd | $G^4$ | $G^3$ | $G^2$ | $G^1$ |
|---|---|---|---|---|
| Apo6995 | H | H | $CF_3CH_2$ | $CH_3$ |
| Apo7030 | H | H | $CF_3CH_2$ | $CH_3CH_2$ |
| Apo7041 | H | H | $CH_3$ | $CF_3CH(NMe_2)—$ |
| Apo7080 | H | H | $CH_3$ | $CF_2HCH_2—$ |
| Apo7067 | H | H | $CF_3CH_2$ | $Me_2NCH_2—$ |
| Apo7056 | $CF_3CH(NHMe)—$ | H | $CH_3$ | $CH_3$ |

Figure 4:
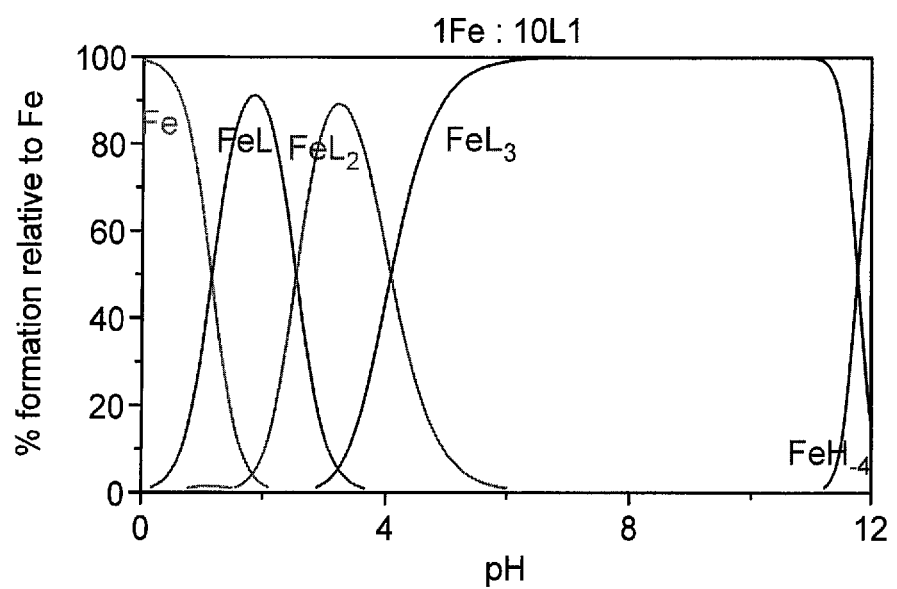
FIG. 4 is a diagrammatic representation of the Fe specification plot of the Fe: deferiprone system in the ratio of 1:10 with [Fe]=1×10$^{-6}$ M and [deferiprone]=1×10$^{-5}$ M.

It is generally accepted that 1,2-dimethyl-3-hydroxypyrid-4-one and its alkyl derivatives are bidentate ligands (Ls) and react with Fe(III) to form neutral 1:3 chelates. In the specification plot as shown in FIG. 4, the percentage of $FeL_3$ species is close to 100 at pH 7.4 when deferiprone is used as ligand. The resulting Fe chelate ($FeL_3$) is not redox active, as evidenced by cyclic voltammetry analysis. However, if the pH is lowered to 6.0, a mixture of $FeL_2^+$ and $FeL_3$ species are now present in solution. Deferiprone (1,2-dimethyl-3-hydroxypyrid-4-one) is effective on the removal of Fe(III) at pH>7.2 at physiological conditions, but at a lower pH, deferiprone and its alkyl derivatives are significantly less effective.

Hider et al. (J. Pharm. Pharmacol. 2000, 52, 263-273; European Journal of Medicinal Chemistry 2008, 42, 1035-1047) reported the use of alkylamino derivatives of 3-hydroxypyridin-4-ones. Two specification plots are illustrated with two different concentration of 2-ethyl-3-hydroxy-1-[2-(piperidin-1-yl)ethyl]pyridin-4(1H)-one [L] at $1×10^{-5}$ M and $7×10^{-4}$ M, respectively, while maintaining the concentration of [Fe] fixed at $1×10^{-6}$M. The $FeL_3$ chelate has a broader stability profile only at pH>5 and above, and when [L] is $7×10^{-4}$ M (FIG. 9 of J. Pharm. Pharmacol. 2000, 52, 271). However, at a concentration of [L] at $1×10^{-5}$ M, the $FeL_3$ stability profile is very similar to that of Fe-deferiprone complex.

Figure 5:
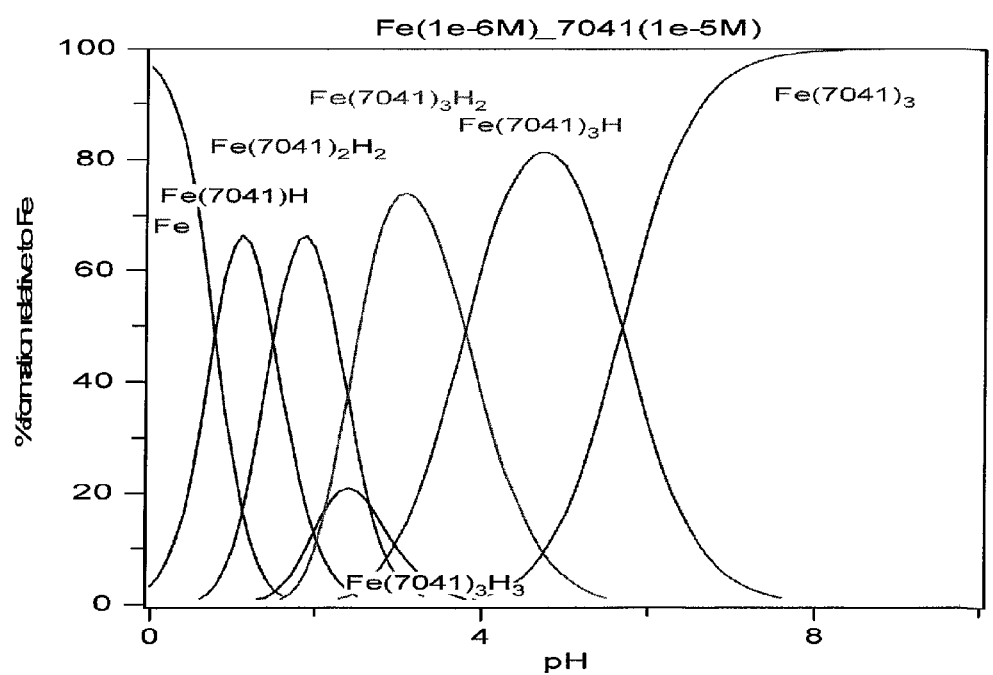
FIG. 5 is a diagrammatic representation of the Fe specification plot of the Fe: Apo7041 system in the ratio of 1:10 with [Fe]=1×10$^{-6}$ M and [Apo7041]=1×10$^{-5}$ M.

Selected amino compounds of this invention such as Apo7041 have $FeL_3$ chelate stability that extends from pH 5 and above. Analysis of photospectroscopic data of the Fe chelate shows that the fluorinated 3-hydroxypyridin-4-one with weak base amino group is a stronger proton acceptor than the oxygen atom in the Fe—O bond of the chelate. Between pH 5 to 7.2, the Fe(III) is trapped as a ferric chelate in the form of $FeL_3$ and $FeL_3H$. The Apo7041 specification plot in FIG. 5 showed that no $FeL_2$ is present at above pH 5.0. In addition, the ligand concentration [L] does not affect the outcome of specification plot in this chemical study.

Figure 6:
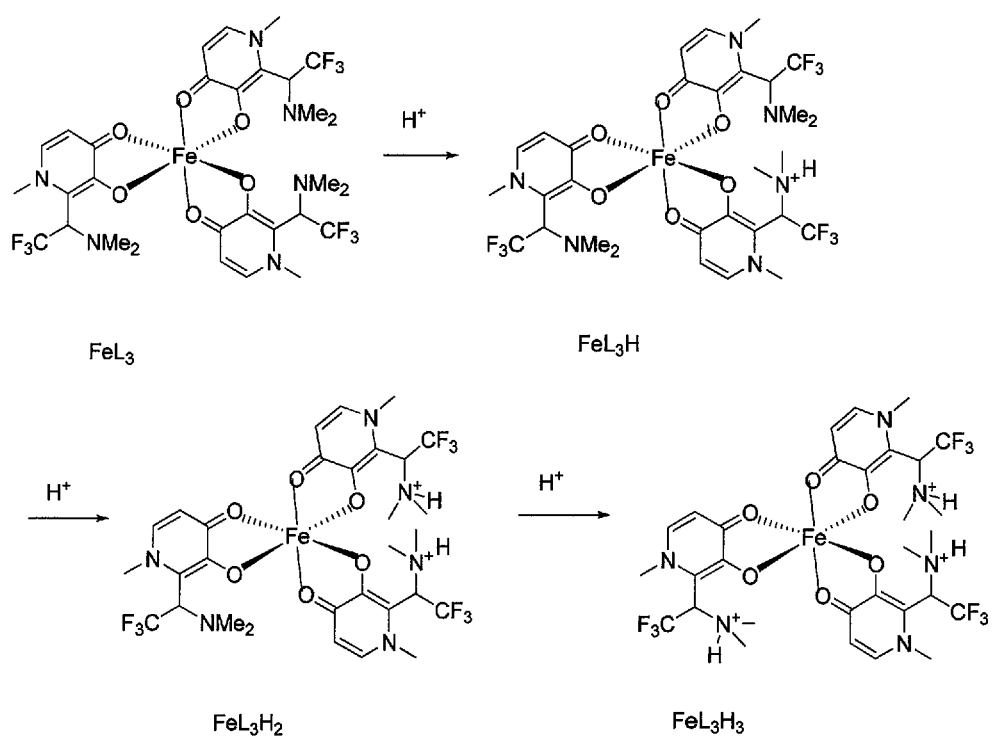
FIG. 6 is a diagrammatic representation of the protonation of the chelate of Apo7041. The Fe-chelate of a weak base is a proton sink. Protonated FeL$_3$ species via protonation of the amine moieties FeL$_3$ to FeL$_2$ are present in acidic medium. Conversion of FeL$_3$ to FeL$_2$ occurs only at very low acidic pH.
Figure 7:
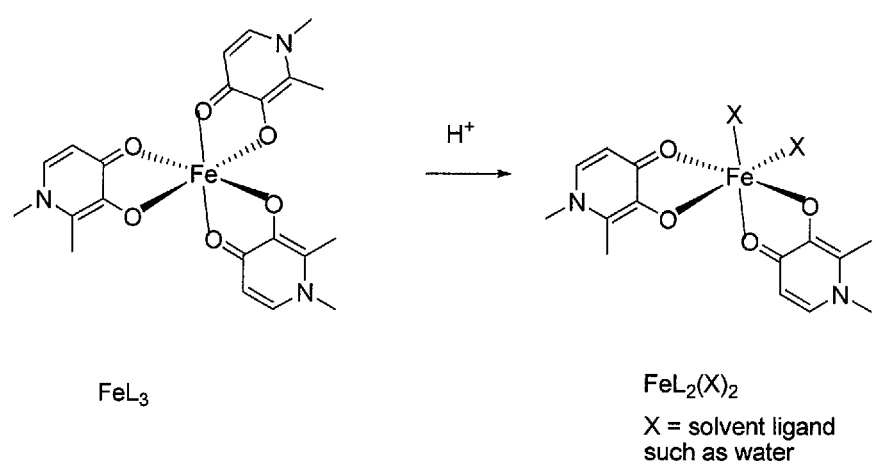
FIG. 7 is a diagrammatic representation of the degradation of FeL$_3$ to FeL$_2$ for neutral 3-hydroxypyridin-4-ones.

The number of weak basic amines available as proton acceptor is three in the ferric chelate. Before the scission of the Fe—O bond of the 1:3 chelate, all three amino groups have to be protonated. The characteristic of this compound behaving as an internal proton sink results in an improvement in the chelate stability at low pH, which offers clear advantage over the neutral 3-hydroxypyridin-4-ones such as deferiprone. FIG. 6 and FIG. 7 outline the comparison of the neutral and basic amine chelates. Upon dropping the pH to around 5.0, a significant amount of $FeL_3$ decomposed to give $FeL_2$ via the cleavage of the Fe—O bond when L is a neutral ligand. However, the chelates from the basic amines derivatives of formula I in this invention are stable at lower pHs.

Figure 8:
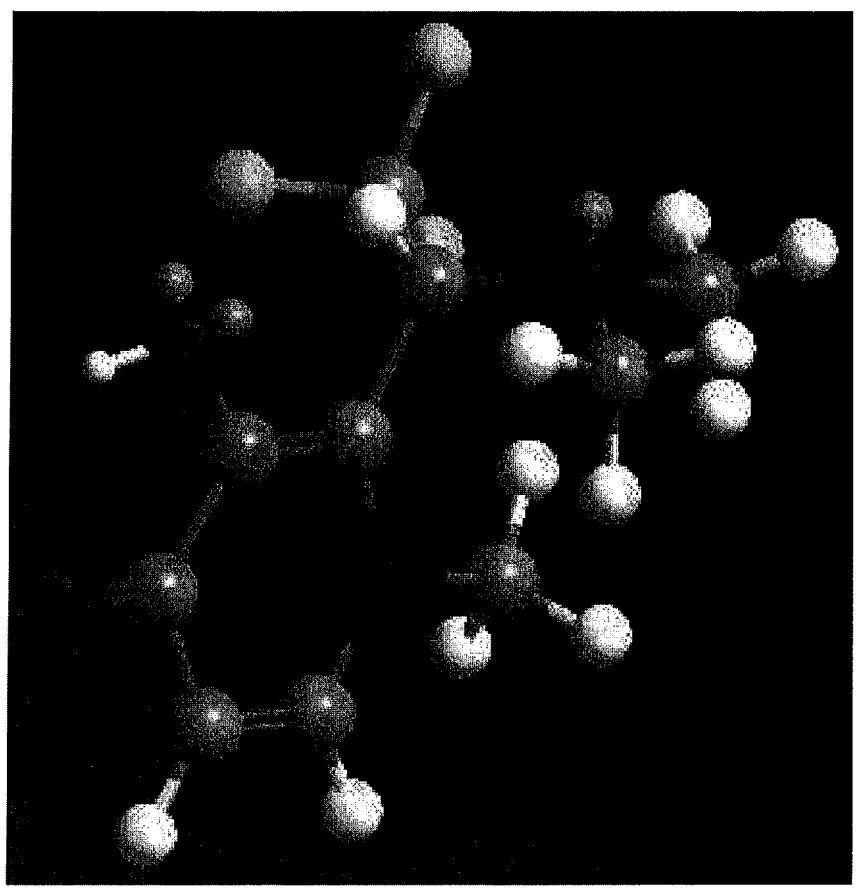
FIG. 8 is a diagrammatic representation of the Apo7041 ligand. The steric bulk at the $C_2$ position is designed to block phase II metabolism involving glucuronidation of the $C_3$ oxygen.

Deferiprone undergoes Phase II metabolism resulting in extensive glucuronidation at the C3 oxygen of the 3-hydroxypyridin-4-one skeleton. Therefore, a high oral dose of deferiprone is required to achieve therapeutic effect. Selected compounds of this invention are designed specifically to block the C3 oxygen from glucuronidation by the introduction of a bulky C3 or C5 trifluoroethyl moiety substituted with an amine derivative. In modeling studies, a simple trifluoroethyl group has the same steric bulk as an isopropyl group. For example, the steric bulk of a 1-dimethylamino-2-trifluoroethyl substituent may prevent the C3 O-glucuronidation without affecting the formation of the ferric chelate $FeL_3$. The 3D modeling of the compound $Fe(Apo7041)_3$ is shown in FIG. 8.

Figure 2:
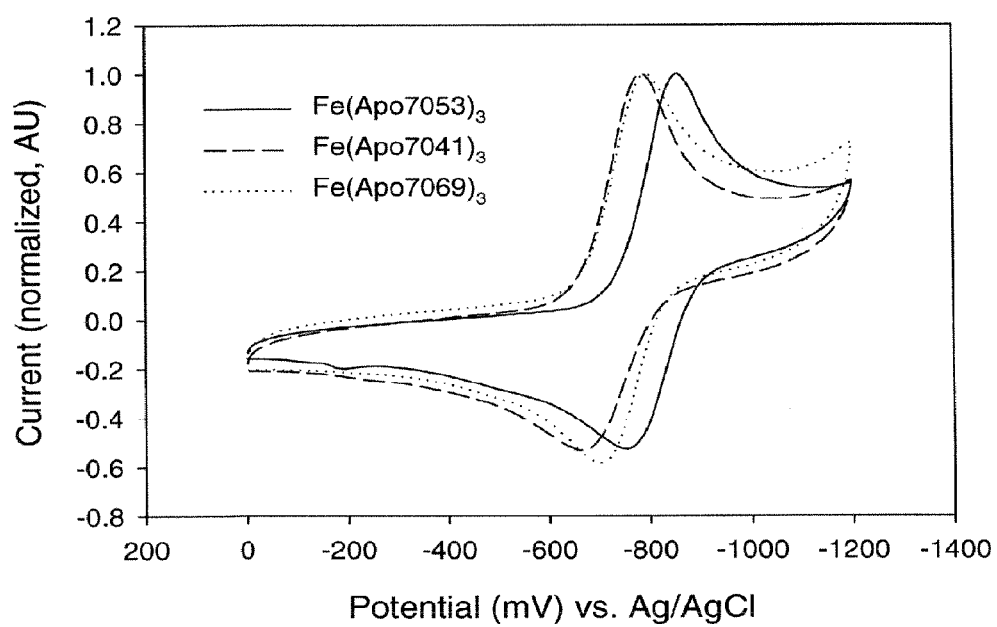
FIG. 2 is a diagrammatic representation of the cyclic voltammetry (CV) of the Fe chelate of three representative compounds of Formula I, Apo7041 ($G^2$=Me, $G^1$=CH(NMe$_2$)CF$_3$, $G^4$=H, $G^3$=H), Apo7053 ($G^2$=Me, $G^1$=Me, $G^4$=CH(NMe$_2$)CF$_3$, $G^3$=H), Apo7069 ($G^2$=CH$_2$CHF$_2$, $G^1$=Me, $G^4$=H, $G^3$=H).

Cyclic voltammetry experiments show that a stable $Fe(Apo7041)_3$ is formed with $E_{1/2}=-731$ mV (FIG. 2). The data showed that the $Fe(Apo7041)_3$ is non redox active and is a stable chemical entity. The cumulative log $\beta_{130}$ value of Apo7041 for Fe(III) is 38.8 (Table 29B in example 29B), which is relatively higher than that of deferiprone with a value of 37.24 (Table 1). Unlike other amine derivatives of 3-hydroxypyridin-4-on reported by Hider et al., the pKa of the C2-amino moiety of Apo7041 is 3.5 in 0.1 M aqueous NaCl. Thus, at pH 3.5, the protonated form and the non-protonated form of the amine exist in a 1:1 ratio. With an incremental unit increase in pH, there will be significantly more free base present in the media.

Selected amino derivatives of this invention have better metal selectivity when compared to deferiprone. The metal binding properties of Apo7041 are compared to those of deferiprone in Table 1. For example, the cumulative log $\beta_{120}$ for Zn(II) and Cu(II) are 13.2 and 17.3, respectively, for Apo7041, which are 2 to 3 orders of magnitude lower as compared to those for deferiprone at 15.0 and 20.5, respectively, in 0.1M aqueous NaCl/MeOH, 1/1, v/v. Thus, the amine derivatives of this invention are selective for Fe(III). The ranking according to binding affinities are Fe(III)>>Cu(II)>>Zn(II).

TABLE 1

Comparison of the metal binding properties of the amino compound Apo7041 and deferiprone.[a,b]

| Properties | Deferiprone | Apo7041 |
|---|---|---|
| $pKa$[a] | $pKa_1 = 10.6$<br>$pKa_2 = 4.0$ | $pKa_1 = 10.1$<br>$pKa_2 = 3.2$<br>$pKa_3 = 2.0$ |
| $Cu^{2+}$ chelation[a] | $Log\beta_1 = 10.8$<br>$Log\beta_2 = 20.5$<br>$pCu^{2+} = 9.9$ | $Log\beta_{111} = 14.1$<br>$Log\beta_{122} = 27.9$<br>$Log\beta_{121} = 23.0$<br>$Log\beta_{120} = 17.3$<br>$pCu^{2+} = 7.7$ |
| $Zn^{2+}$ chelation[a] | $Log\beta_1 = 8.1$<br>$Log\beta_2 = 15.0$<br>$pZn^{2+} = 6.3$ | $Log\beta_{111} = 13.1$<br>$Log\beta_{121} = 19.6$<br>$Log\beta_{120} = 13.2$<br>$pZn^{2+} = 6.0$ |
| $Fe^{3+}$ chelation[b] | $pKa_1 = 9.92$<br>$pKa_2 = 3.55$<br>$Log\beta_{110} = 14.85$<br>$Log\beta_{120} = 27.25$<br>$Log\beta_{130} = 37.24$<br>$pFe^{3+} = 20.2$ | $pFe^{3+} = 23.4$ |

[a]Except for $Fe^{3+}$, the pKas and log β values were determined in 0.1M aqueous NaCl/MeOH, 1/1, v/v, mixture.
[b]For $Fe^{3+}$, the pKas and log β values were determined in 0.1M aqueous NaCl. For details, see Example 29B A utility of compounds of this invention may be in the treatment of patients with kidney disease in which the presence of iron is detected in the urine. The detection of both protein content and free iron in urine as a possible method of monitoring kidney disease has been reported in U.S. Pat. No. 6,906,052.

One biological function of the kidney is to retain protein. The term "proteinuria" means the presence of an excess of serum proteins in the urine, and may be a sign of renal (kidney) damage. Injury to the glomerulus or tubule or pancreas can adversely affect the ability of the kidney to retain protein. In the urine of animals with nephritic syndrome, the pH of the urine can vary from pH 5.2 to 7.8. Animal experiments have shown that iron is bound to transferrin at a pH of 6.05. When the pH drops to below 6.0, there is a marked increase in unbound iron. Iron dissociated from transferrin is able to cause potentially serious free radical damage to the kidney. Small low molecular chelator such as deferiprone has been used to chelate the free iron as a possible treatment therapy.

Cooper et al. reported the urinary iron specification (American Journal of Kidney Diseases, 25, 1995, 314-319) in nephrotic syndrome where iron is presented to the tubule fluid in a nonreactive form in association with transferrin as a result of the glomerular protein leak. In nephritic rats, iron remains bound to transferrin throughout the nephron and is excreted as such in the urine at alkaline pH. As urine pH decreases below 6, iron starts to dissociate from transferrin. As mentioned earlier, free iron is redox active and may cause further progression of the renal diseases.

A weak base compound can accumulate at an acidic compartment to exert its biological action. Neutral compounds and strong bases do not accumulate in such a manner. For example, the antisecretory agent omeprazole is a weak base that concentrates in the acidic compartment of the parietal cell to exert its pharmacological properties. The amino derivatives of 3-hydroxypyridin-4-one of this invention favor the accumulation at sites wherein the compartment is slightly acidic. One such example may be the nephron of kidney disease patients.

The amino derivatives of 3-hydroxypyridin-4-one of this invention have at least one of a number of properties: (a) they are weak amines that can accumulate in the acidic compartment of a biological system; (b) the 1:3 $FeL_3$ chelates are stable at lower pH between 5 and 7.2 when compared to the chelate from the neutral alkyl derivatives of 3-hydroxypyridin-4-one such as deferiprone; (c) they are non-redox active as evidenced by the cyclic voltammetric study; (d) they carry a bulky substituent at the C2 or C5 position that may block the glucuronidation of the C3-OH, and may thus require a lower therapeutic dose of drug; (e) higher clearance rate than deferiprone in cassette dosing pharmacokinetic studies. Thus compounds of this invention may have a propensity to undergo urinary excretion, and it is understood that the relevant site of free iron for renal disease patients is the kidney.

Another possible utility of the amino compounds of this invention is in the treatment of cancer and inflammatory lung disorders. Buss et al. reviewed the role of iron chelation in cancer therapy (Current Medicinal Chemistry, 2003, 12, 1021-1034). DNA damage after oxidative stress involves a transition metal such as iron. Lysosomes contain a comparatively high concentration of redox-active iron, which is mainly generated from the degradation of iron-containing proteins. The acidic compartment of the lysosome further facilitates iron catalysed oxidative reactions (Kurz et al., Biochem. J. (2004) 378, 1039-1045). The iron chelator DFO has been reported to inhibit DNA synthesis and cell proliferation. DFO is a weak base with a free amino terminal and can accumulate in the lysosome to exert its chelation mechanism. Unfortunately, DFO is a large peptide hexadentate chelator and will not easily penetrate the cell. The amine compounds of this invention are low molecular weight compounds. The weak basic nature of the compound and its lipophilic character allows the compound to accumulate in the acidic compartment of the lysosomes.

Richardson et al. reported that the most important cellular pool of redox-active iron may exist within lysosomes, making the organelles vulnerable to oxidative stress (Expert Opinion on Investigational Drugs, August 2005, Vol. 14, No. 8, Pages 997-1008). Oxidative stress will result in tissue damage. As a result, iron-chelating therapy that targets the lysosome may be a possible treatment strategy for inflammatory pulmonary diseases. Weak base cell-permeable low molecular weight iron chelators may accumulate in the acidic compartment of lysosomes, and may therefore be more effective than desferrioxamine as cytoprotective agents. Therefore, another possible utility for the weak bases of this invention is the use of such compounds for the treatment of inflammatory pulmonary diseases.

Most of the non-amino $N^1$-trifluoroethyl or $C^2$-difluoroethyl derivatives of 3-hydroxypyridin-4-one of this invention are intermediates for the synthesis of the amino derivatives. In addition, compounds of formula I wherein $G^1$ is $C_1$-$C_6$ alkyl and $G^2$ is trifluoroethyl or $G^1$ is difluoroethyl and $G^2$ is $C_1$-$C_6$ alkyl are examples of derivatives of 3-hydroxypyridin-4-ones without an amine side chain. Some of these neutral derivatives of 3-hydroxypyridin-4-one of this invention are significantly more lipophilic than deferiprone. In BBB cassette dosing studies, they display higher brain to plasma concentration ratio, making them more favorable for accumulation in the brain. These compounds may be targeted for accumulation in the brain and used towards treatment of diseases such as Friedreich's ataxia wherein the chelator is used to reduce ataxia and cerebellar iron in the brain.

All compounds of this invention have specificity for the complexation of Fe(III) with favorable phenolic C3 OH pKas and pFe(III)>19, a smooth 1:3 ferric chelate formation as evident by Job's plot, and a $D_{7.4}$ value >0.1. Further, the metal selectivity studies show that the compound does not chelate essential metals such as calcium, magnesium and zinc.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

Various alternative embodiments and examples of the invention are described herein. These embodiments and examples are illustrative and should not be construed as limiting the scope of the invention.

Example 1

Preparation of 3-hydroxy-2-methyl-1-(2,2,2-trifluoroethyl)pyridin-4(1H)-one

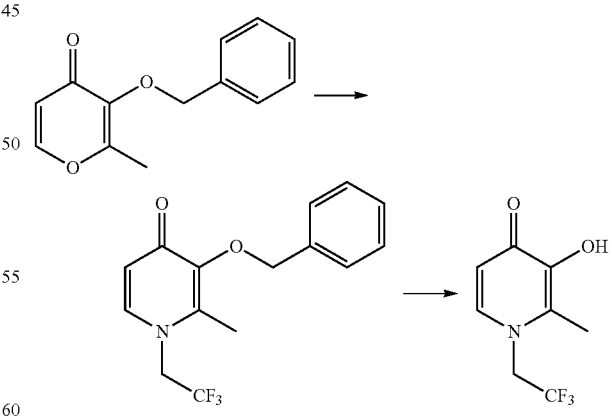

(a) Preparation of 3-(benzyloxy)-2-methyl-1-(2,2,2-trifluoroethyl)pyridin-4(1H)-one 3-(Benzyloxy)-2-methyl-4H-pyran-4-one (1.00 g, 4.6 mmol) was mixed with trifluoroethylamine hydrochloride (1.35 g, 10.0 mmol) in pyridine (10 mL). The reaction mixture was heated in a sealed flask at 75° C. for 5 hours. The mixture was concentrated and the residue was purified by column chromatography on silica gel with 5% methanol in ethyl acetate as eluant to give 3-(benzyloxy)-2-methyl-1-(2,2,2-trifluoroethyl)pyridin-4(1H)-one (0.82 mg) as beige solid. Yield=60%; $^1$H NMR (CDCl$_3$, 90 MHz) δ (ppm): 7.02-7.58 (m, 6H), 6.42 (d, J=7.5 Hz, 1H), 5.20 (s, 2H), 4.30 (q, J=8.3 Hz, 2H) and 2.10 (s, 3H).

(b) Preparation of 3-hydroxy-2-methyl-1-(2,2,2-trifluoroethyl)pyridin-4(1H)-one 3-(Benzyloxy)-2-methyl-1-(2,2,2-trifluoroethyl)pyridin-4(1H)-one (820 mg, 2.8 mmol) was mixed with 10% palladium on charcoal (wet, 84 mg) in methanol (20 mL). The mixture was stirred at room temperature under hydrogen at 30 psi in a Parr apparatus for 35 minutes. The mixture was filtered through Celite™ and the filtrate was concentrated. The residue was triturated with ether to give 3-hydroxy-2-methyl-1-(2,2,2-trifluoroethyl)pyridin-4(1H)-one (511 mg) as off-white solid. Yield=89%; $^1$H NMR (DMSO-D$_6$, 90 MHz) δ (ppm): 7.60 (d, J=7.4 Hz, 1H), 6.20 (d, J=7.4 Hz, 1H), 4.99 (q, J=8.8 Hz, 2H) and 2.29 (s, 3H).

Example 2

Preparation of 3-hydroxy-2-ethyl-1-(2,2,2-trifluoroethyl)pyridin-4(1H)-one

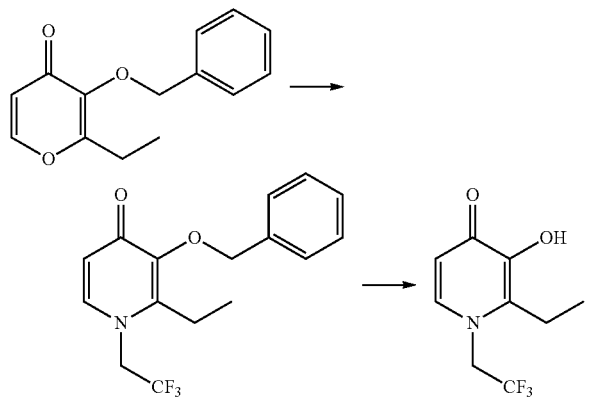

(a) In a similar manner as in example 1(a), 3-(benzyloxy)-2-ethyl-1-(2,2,2-trifluoroethyl)pyridin-4(1H)-one (1.10 g) was prepared from 3-(benzyloxy)-2-ethyl-4H-pyran-4-one (1.20 g, 5.2 mmol) and 2,2,2,-trifluoroethylamine hydrochloride (3.57 g, 26.1 mmol) in pyridine (10 mL). Yield=67%; $^1$H NMR (MeOD-D$_4$, 90 MHz) δ (ppm): 7.07-7.59 (m, 6H), 6.51 (d, J=7.7 Hz, 1H), 5.20 (s, 2H), 4.38 (q, J=7.7 Hz, 2H), 2.58 (q, J=7.5 Hz, 2H) and 0.97 (t, J=7.5 Hz, 3H); MS m/z 312 [M+1]$^+$.

(b) In a similar manner as described in example 1(b), 2-ethyl-3-hydroxy-1-(2,2,2-trifluoroethyl)pyridin-4(1H)-one (0.30 g) was prepared from 3-(benzyloxy)-2-ethyl-1-(2,2,2-trifluoroethyl)pyridin-4(1H)-one (0.90 g, 2.9 mmol) with 10% palladium on charcoal (wet, 90 mg) in methanol (5 mL) and ethanol (35 mL) under hydrogen at 15 psi for 1.5 hours. Yield=47%; $^1$H NMR (DMSO-D$_6$, 400 MHz) δ (ppm): 7.58 (d, J=7.3 Hz, 1H), 6.41 (d, J=7.3 Hz, 1H), 4.92 (q, J=8.1 Hz, 2H), 2.72 (t, J=7.5 Hz, 2H) and 1.20 (t, J=7.5 Hz, 3H); MS m/z 222 [M+1]$^+$.

Example 3

Preparation of 1-(2,2-difluoroethyl)-3-hydroxy-2-methylpyridin-4(1H)-one

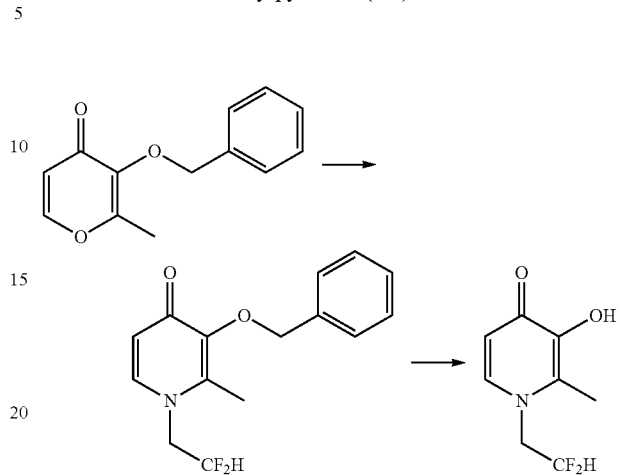

(a) Preparation of 3-(benzyloxy)-1-(2,2-difluoroethyl)-2-methylpyridin-4(1H)-one.

3-(Benzyloxy)-2-methyl-4H-pyran-4-one (432 mg, 2.0 mmol) was mixed with 2,2-difluoroethylamine (655 mg, 8.0 mmol) and triethylamine hydrochloride (1.10 g, 8.0 mmol) in pyridine (6 mL) in a sealed vial. The reaction mixture was heated at 110° C. for overnight. The solid was filtered and washed with ethyl acetate. The filtrate was concentrated under reduced pressure and the residue was mixed with water, and then extracted with ethyl acetate. The organic layer was washed with water and brine. The product was purified by column chromatography on silica gel with 5% methanol in ethyl acetate as eluant to give 3-(benzyloxy)-1-(2,2-difluoroethyl)-2-methylpyridin-4(1H)-one (337 mg) as pale-yellow solid. Yield=60%; $^1$H NMR (MeOD-D$_4$, 90 MHz) δ (ppm): 7.66 (d, J=7.1 Hz, 1H), 7.16-7.55 (m, 5H), 6.46 (d, J=7.1 Hz, 1H), 5.55 (t, J=55.0 Hz, 1H), 4.45 (t, J=14.8 Hz, 1H) and 2.20 (s, 3H); MS m/z 280 [M+1]$^+$.

(b) In a similar manner as example 1(b), 1-(2,2-difluoroethyl)-3-hydroxy-2-methylpyridin-4(1H)-one (160 mg) was prepared from 3-(benzyloxy)-1-(2,2-difluoroethyl)-2-methylpyridin-4(1H)-one (337 mg, 1.2 mmol) with 10% Pd/C (wet, 90 mg) in methanol under 1 atmosphere of hydrogen using a balloon for 5 minutes. Yield=70%; $^1$H NMR (MeOD-D$_4$, 90 MHz) δ (ppm): 7.60 (d, J=7.3 Hz, 1H), 6.39 (d, J=7.3 Hz, 1H), 6.23 (tt, J=54.0, 2.9 Hz, 1H), 4.51 (td, J=14.8, 2.9 Hz, 2H) and 2.43 (s, 3H); MS m/z 190 [M+1]$^+$.

Example 4

Preparation of 5-hydroxy-2-methyl-1-(2,2,2-trifluoroethyl)pyridin-4(1H)-one

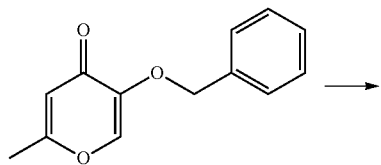

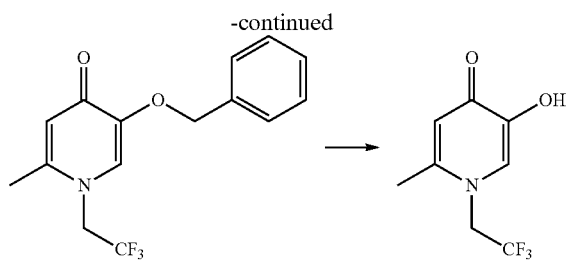

(a) Preparation of 5-(benzyloxy)-2-methyl-1-(2,2,2-trifluoroethyl)pyridin-4(1H)-one.

5-(Benzyloxy)-2-methyl-4H-pyran-4-one (4.32 g, 20.0 mmol) was mixed with trifluoroethylamine (6.92 g, 70.0 mmol) in 6N HCl (11.7 mL) and ethanol (5.8 mL). The reaction mixture was heated in a sealed flask at 100° C. for 20 hours. The mixture was then concentrated in vacuo and the residue was diluted with water. The solid was filtered, washed with water and ether to give 5-(benzyloxy)-2-methyl-1-(2,2,2-trifluoroethyl)pyridin-4(1H)-one (5.01 g) as white solid. Yield=84%; $^1$H NMR (MeOD-D$_4$, 90 MHz) δ (ppm): 7.99 (s, 1H), 7.14-7.65 (m, 5H), 6.80 (s, 1H), 4.91-5.25 (m, 4H), 2.53 (s, 3H).

(b) 5-(Benzyloxy)-2-methyl-1-(2,2,2-trifluoroethyl)pyridin-4(1H)-one (45.8 g, 164 mmol) was mixed with 6N HCl (100 mL) and isopropanol (20 mL). The mixture was heated at 110° C. oil bath for 8 hours and then concentrated by rotary evaporator. The residue was triturated with acetone and ether to give 5-hydroxy-2-methyl-1-(2,2,2-trifluoroethyl)pyridin-4(1H)-one hydrochloride (24.5 g). Yield=65%; $^1$H NMR (MeOD-D$_4$, 90 MHz) δ (ppm): 8.18 (s, 1H), 7.21 (s, 1H), 5.31 (q, J=8.2 Hz, 2H) and 2.67 (s, 3H).

Example 5

Preparation of 1-(2,2-difluoroethyl)-5-hydroxy-2-methylpyridin-4(1H)-one

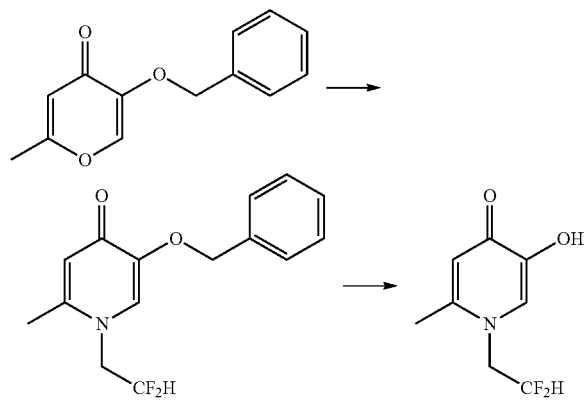

(a) In a similar manner as described in example 4(a), 5-(benzyloxy)-1-(2,2-difluoroethyl)-2-methylpyridin-4 (1H)-one (2.20 g) was prepared from a mixture of 5-(benzyloxy)-2-methyl-4H-pyran-4-one (3.00 g, 13.8 mmol), difluoroethylamine (2.48 g, 55.2 mmol), triethylamine hydrochloride (5.58 g, 55.2 mmol) and pyridine (15 mL). Yield=58%; $^1$H NMR (90 MHz, MeOD-D$_4$) δ (ppm): 7.53 (s, 1H), 7.27-7.45 (m, 5H), 6.36 (s, 1H), 5.56-6.77 (tt, J=54.9, 3.6 Hz, 1H), 5.04 (s, 2H), 4.24-4.60 (td, J=14.9, 2.7, 2H) and 2.36 (s, 3H); MS m/z 280 [M+1]$^+$.

(b) In a similar manner as described in example 1(b), 1-(2,2-difluoroethyl)-5-hydroxy-2-methylpyridin-4(1H)-one (230 mg) was prepared from 5-(benzyloxy)-1-(2,2-difluoroethyl)-2-methylpyridin-4(1H)-one (500 mg, 1.80 mmol) with 10% Pd/C (wet, 50 mg) in methanol (40 mL) under hydrogen at 15 psi pressure in a Parr apparatus for 27 minutes. Yield=99%; $^1$H NMR (MeOD-D$_4$, 90 MHz) δ (ppm): 7.46 (s, 1H), 6.37 (s, 1H), 5.62-6.83 (tt, J=54.9, 3.6. Hz, 1H), 4.26-4.60 (td, J=15.3, 2.4 Hz, 2H) and 2.38 (s, 3H); MS m/z 190 [M+1]$^+$.

Example 6

Preparation of 3-hydroxy-1-(2,2,2-trifluoroethyl)pyridin-4(1H)-one

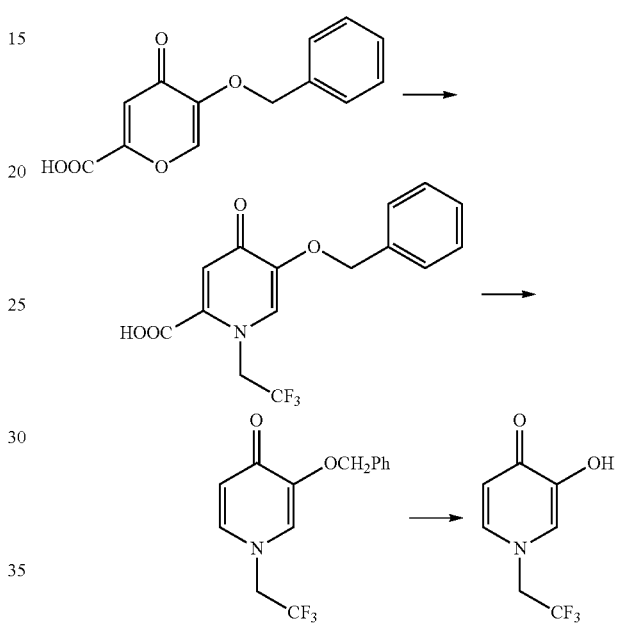

(a) 5-(Benzyloxy)-4-oxo-4H-pyran-2-carboxylic acid (10.5 g, 42.7 mmol) was dissolved in sodium hydroxide solution (1.71 g, 42.7 mmol in 77 mL de-ionized water). 2,2,2-Trifluoroethylamine hydrochloride (23.1 g, 171 mmol) was added and the resulting suspension was stirred at 70° C. (oil-bath temperature) in the sealed flask for 17 hours. The reaction mixture was then filtered and the off-white solid was washed with de-ionized water (20 mL×5) to give 5-(benzyloxy)-4-oxo-1-(2,2,2-trifluoroethyl)-1,4-dihydropyridine-2-carboxylic acid (6.00 g). Yield=43%; $^1$H NMR (MeOD-D$_4$, 90 MHz) δ 7.30 (s, 1H), 6.76-7.09 (m, 5H), 6.71 (s, 1H), 4.93 (d, J=8.4 Hz, 2H) and 4.65 (s, 2H); MS m/z 328 [M+1]$^+$.

(b) 5-(Benzyloxy)-4-oxo-1-(2,2,2-trifluoroethyl)-1,4-dihydropyridine-2-carboxylic acid (4.70 g, 14.4 mmol) was mixed with DMF (25 mL) and heated to 130° C. (bath temperature) for 3 hours. The mixture was concentrated under reduced pressure using a rotary evaporator and the residue was mixed with ethyl acetate (50 mL). It was then stirred for 2 hours at room temperature and filtered. The filtrate was concentrated to give 3-(benzyloxy)-1-(2,2,2-trifluoroethyl)pyridin-4(1H)-one (3.58 g). Yield=69%; $^1$H NMR (DMSO-D$_6$, 400 MHz) δ (ppm) 7.57-7.84 (m, 2H), 7.22-7.57 (m, 5H), 6.25 (br. s, 1H) and 4.69-5.28 (m, 4H); MS m/z 284 [M+1]$^+$.

(c) 3-(Benzyloxy)-1-(2,2,2-trifluoroethyl)pyridin-4(1H)-one (1.2 g, 4.2 mmol) was mixed with 10% Palladium on charcoal (wet, 0.12 g) in ethanol (70 mL). The resulting mixture was hydrogenated at 15 psi of hydrogen pressure for 1.5 hours. Palladium was removed by filtration through a layer of Celite™ and the Celite™ cake was washed with methanol (5 mL×3). The filtrate was evaporated to give 3-hydroxy-1-(2,2,2-trifluoroethyl)pyridin-4(1H)-one (0.78 g) as white solid. Yield=95%; $^1$H NMR (DMSO-D$_6$, 400 MHz) δ (ppm) 7.60 (d, J=7.1 Hz, 1H), 7.46 (s, 1H), 6.23 (d, J=7.1 Hz, 1H) and 4.80-5.00 (m, 2H); MS m/z 194 [M+1]$^+$.

Example 7

Preparation of 3-hydroxy-2-(hydroxymethyl)-6-methyl-1-(2,2,2-trifluoroethyl)pyridin-4(1H)-one

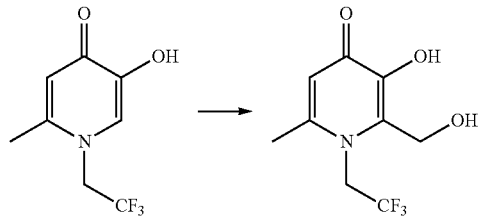 [SMILES: Cc1cc(=O)c(O)cn1CC(F)(F)F ; Cc1cc(=O)c(O)c(CO)n1CC(F)(F)F]

5-Hydroxy-2-methyl-1-(2,2,2-trifluoroethyl)pyridin-4(1H)-one hydrochloride (4.87 g. 20.0 mmol) was mixed with 37% formaldehyde (30 mL) and 6N sodium hydroxide (7 mL, 42.0 mmol). The reaction mixture was stirred at 39-42° C. for 11 hours, and then additional 37% formaldehyde (30 mL) was added. The reaction mixture was stirred at 37° C. for 12 hours and then left at room temperature for a further 12 hours. The solid was filtered and the filtrate was acidified to pH about 5 to 6. The solution was concentrated with silica gel and the product was purified by column chromatography with a gradient mixture of 5-10% methanol in ethyl acetate as eluant to give the title compound 3-hydroxy-2-(hydroxymethyl)-6-methyl-1-(2,2,2-trifluoroethyl)pyridin-4(1H)-one (3.02 g) as pale-peach solid. Yield 63.5%; $^1$H NMR (DMSO-D$_6$+D$_2$O, 90 MHz) δ (ppm): 6.20 (s, 1H), 5.15 (q, J=8.8 Hz, 2H), 4.33-4.92 (m, 2H) and 2.37 (s, 3H); MS m/z 238 [M+1]$^+$.

Example 8

A. Preparation of 2-[(dimethylamino)methyl]-3-hydroxy-6-methyl-1-(2,2,2-trifluoroethyl)pyridin-4(1H)-one

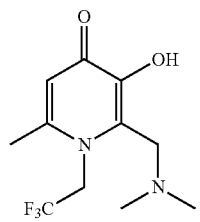

5-Hydroxy-2-methyl-1-(2,2,2-trifluoroethyl)pyridin-4(1H)-one hydrochloride (415 mg, 1.7 mmol) was mixed with N,N,N',N'-tetramethylmethanediamine (4 mL) in ethanol (10 mL) and heated at 80° C. for 21 hours. The reaction mixture was concentrated by rotary evaporator and the residue was triturated with water to give 2-[(dimethylamino)methyl]-3-hydroxy-6-methyl-1-(2,2,2-trifluoroethyl)pyridin-4(1H)-one (315 mg) as white solid. Yield=70%; $^1$H NMR (DMSO-D$_6$+D$_2$O, 90 MHz) δ (ppm): 6.20 (s, 1H), 5.15 (q, J=8.8 Hz, 2H), 4.69 (br. s, 2H) and 2.37 (s, 3H); MS m/z 265 [M+1]$^+$.

B. Preparation of 2-[(dimethylamino)methyl]-3-hydroxy-1-(2,2,2-trifluoroethyl)pyridin-4(1H)-one

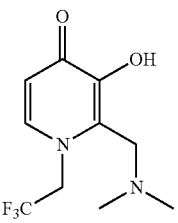

In a similar manner, 2-[(dimethylamino)methyl]-3-hydroxy-1-(2,2,2-trifluoroethyl)pyridin-4(1H)-one (0.21 g) was prepared from 3-hydroxy-1-(2,2,2-trifluoroethyl)pyridin-4(1H)-one (0.60 g, 3.1 mmol) reacted with N,N,N',N'-tetramethyldiaminomethane (8.50 mL, 62.2 mmol) in ethanol (10 mL) at 75° C. for 20 hours. Yield=27%; $^1$H NMR (MeOD-D$_4$, 90 MHz) δ (ppm): 7.81 (d, J=7.5 Hz, 1H), 6.52 (d, J=7.5 Hz, 1H), 5.07 (d, J=8.0 Hz, 2H), 4.60 (s, 2H) and 2.94 (s, 6H); MS m/z 251 [M+1]$^+$.

C. Preparation of 1-(2,2-difluoroethyl)-2-[(dimethylamino)methyl]-3-hydroxy-6-methylpyridin-4(1H)-one

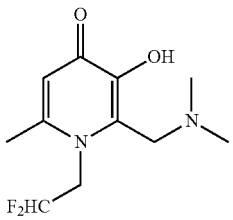

In a similar manner, 1-(2,2-difluoroethyl)-2-[(dimethylamino)methyl]-3-hydroxy-6-methylpyridin-4(1H)-one (0.41 g) was prepared from 1-(2,2-difluoroethyl)-5-hydroxy-2-methylpyridin-4(1H)-one (0.40 g, 2.1 mmol) and N,N,N',N'-tetramethyldiaminomethane (4.3 mL, 31.7 mmol) in ethanol (10 mL) at 75° C. for 19 h. Yield=78%; $^1$H NMR (DMSO-D$_6$, 90 MHz) δ ppm: 6.45 (tt, J=55.1, 3.5 Hz, 1H), 6.24 (s, 1H), 4.74 (td, J=14.6, 3.5 Hz, 2H), 3.55 (s, 2H), 2.37 (s, 3H), 2.17 (s, 6H); MS m/z 247 [M+1]$^+$.

Example 9

Preparation of 3-hydroxy-6-methyl-2-(piperidin-1-ylmethyl)-1-(2,2,2-trifluoroethyl)pyridin-4(1H)-one

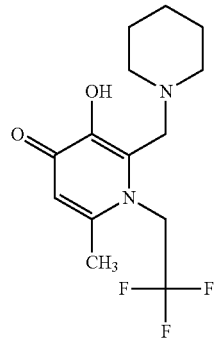 [SMILES: Cc1cc(=O)c(O)c(CN2CCCCC2)n1CC(F)(F)F]

3-Hydroxy-2-(hydroxymethyl)-6-methyl-1-(2,2,2-trifluoroethyl)pyridin-4(1H)-one (375 mg, 1.6 mmol) was mixed with acetonitrile at 80° C. and the thionyl chloride (753 mg, 6.3 mmol) was added. The reaction mixture was stirred for 5 minutes and then concentrated by rotary evaporator to give 2-(chloromethyl)-3-hydroxy-6-methyl-1-(2,2,2-trifluoroethyl)pyridin-4(1H)-one hydrochloride. The chloride compound was added to a solution of piperidine (672 mg, 7.9 mmol) in isopropanol (5 mL) at room temperature. Five minutes later, the reaction mixture was diluted with water and extracted with ethyl acetate. The organic layer was washed with water twice and brine, dried and concentrated. The residue was triturated with ether/hexanes to give 3-hydroxy-6-methyl-2-(piperidin-1-ylmethyl)-1-(2,2,2-trifluoroethyl)pyridin-4(1H)-one (165 mg) as pale orange solid. Yield=34%; $^1$H NMR (MeOD-D$_4$, 90 MHz) δ (ppm): 6.37 (s, 1H), 3.72 (br. s, 2H), 2.45 (br. m, 7H) and 1.51 (br. m, 6H); MS m/z 305 [M+1]$^+$.

Example 10

Preparation of N-methyl-N2-[2,2,2-trifluoro-1-(3-hydroxy-1-methyl-4-oxo-1,4-dihydropyridin-2-yl)ethyl]-D-alaninamide and N-methyl-N2-[2,2,2-trifluoro-1-(3-hydroxy-1-methyl-4-oxo-1,4-dihydropyridin-2-yl)ethyl]-L-alaninamide (Apo6998 and Apo6999)

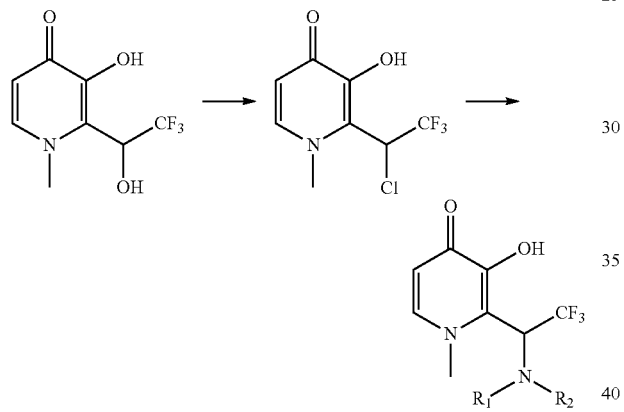

To a solution of 3-hydroxy-1-methylpyridin-4(1H)-one hydrochloride (100.0 g, 0.62 mol) dissolved in a solution of 6N NaOH (206.9 mL) at ice-water bath was added trifluoroacetaldehyde methyl hemiacetal (131.9 mL, 1.24 mmol). The resulting solution was heated to 95° C. for overnight. The reaction mixture was then cooled, and at ice-water bath the pH of the mixture was adjusted to about 5 using a 6N HCl solution. The precipitated solid was collected by filtration, and the solid was thoroughly washed with de-ionized water (100 mL×2), and then dried under vacuum at 43° C. for overnight to afford 3-hydroxy-1-methyl-2-(2,2,2-trifluoro-1-hydroxyethyl)pyridin-4(1H)-one (94.8 g) as a white solid. Yield=68% yield; $^1$H NMR (90 MHz, MeOD-D$_4$) δ (ppm): 7.60 (d, J=7.1 Hz, 1H), 6.40 (d, J=7.2 Hz, 1H), 5.92 (q, J=8.2 Hz, 1H), 3.98 (s, 3H); MS m/z 224 [M+1]$^+$, 158 (100%).

To an ice cooled suspension of

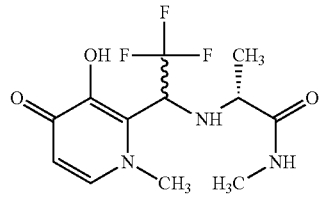 [SMILES: CNC(=O)[C@@H](C)NC(c1c(O)c(=O)ccn1C)C(F)(F)F]

3-hydroxy-1-methyl-2-(2,2,2-trifluoro-1-hydroxyethyl)pyridin-4(1H)-one (1.60 g, 7.2 mmol) in 50 mL of acetonitrile was added dropwise SOCl$_2$ (0.80 mL, 10.8 mmol) followed by pyridine (0.6 mL, 7.2 mmol). The resulting suspension was stirred for 0.5 h and then refluxed for 2 h. The reaction mixture was evaporated to dryness. To a suspension of the residue in 10 mL of acetonitrile was added a suspension of L-H-Ala-NHMe.HCl (1.19 g, 8.6 mmol) and Et$_3$N (4.0 mL, 28.7 mmol) in 20 mL of acetonitrile. The resulting mixture was stirred at RT for overnight. The reaction mixture was evaporated to dryness, and the residue was purified by flash chromatography on silica gel (10% conc NH$_4$OH in IPA as eluant) to afford 2.20 g of the two diastereoisomers, Apo6998 and Apo6999. A sample of each diastereoisomers was obtained through further purification by Biotage using reverse phase C18 cartridge.

More polar isomer by HPLC (Rt=3.43 min) (110 mg). $^1$H NMR (400 MHz, MeOD-D$_4$) δ (ppm): 7.68 (d, J=7.1 Hz, 1H), 6.41 (d, J=7.1 Hz, 1H), 4.68-4.80 (m, 1H), 3.83 (s, 3H), 3.41-3.56 (m, 1H), 2.57 (s, 3H), 1.30 (d, J=6.1 Hz, 3H); MS m/z 330 [M+Na]$^+$, 308 [M+1]$^+$, 126 (100%).

Less polar isomer by HPLC (Rt=3.68 min) (100 mg). $^1$H NMR (400 MHz, MeOD-D$_4$) δ (ppm): 7.70 (d, J=7.1 Hz, 1H), 6.44 (d, J=7.1 Hz, 1H), 4.60-4.70 (m, 1H), 3.79 (s., 3H), 3.20-3.24 (m, 1H), 2.75 (s, 3H), 1.28 (d, J=6.1 Hz, 3H); MS m/z 330 [M+Na]$^+$, 308 [M+1]$^+$, 126 (100%).

HPLC condition: Column: Symmetry C18, 5 µm; 3.9 mm×150 mm; Flow rate: 1.0 mL/min; Mobile phase: A=0.035% HClO$_4$, B=Acetonitrile; Gradient (min-B %): 0-10, 10-100, 12-100, 14-50.

Example 11

Preparation of 2-[1-(dimethylamino)-2,2,2-trifluoroethyl]-3-hydroxy-1-methylpyridin-4(1H)-one (Apo7041)

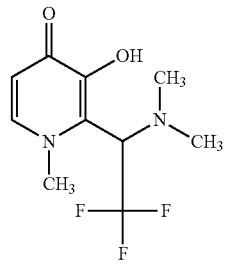 [SMILES: CN(C)C(c1c(O)c(=O)ccn1C)C(F)(F)F]

To a suspension of 3-hydroxy-1-methyl-2-(2,2,2-trifluoro-1-hydroxyethyl)pyridin-4(1H)-one (5.00 g, 22.4 mmol) in 40 mL of acetonitrile at ice-water bath was added Vilsmeier's reagent (4.30 g, 33.6 mmol) portionwise. The resulting mixture was stirred for 2 h before being added to a suspension of dimethylamine hydrochloride (6.00 g, 73.6 mmol) and Et$_3$N (15.0 mL, 107.6 mmol) in 30 mL of acetonitrile. The resulting suspension was stirred at RT for overnight. The solid was filtered off and the filtrate was concentrated to dryness. The residue was purified by flash chromatography on silica gel (10% MeOH in EtOAc as eluant) to afford title compound, Apo7041 (1.8 g). Yield=32%; $^1$H NMR (90 MHz, CD$_3$OD-D$_4$) δ (ppm): 7.63 (d, J=7.3 Hz, 1H), 6.41 (d, J=7.3 Hz, 1H), 4.78 (q, J=8.1 Hz, 1H), 3.99 (s, 3H), 2.41 (s, 6H); MS m/z 273 [M+Na]$^+$, 251 [M+1]$^+$, 206 (100%).

Example 12

A. Preparation of 3-hydroxy-1-methyl-2-{2,2,2-trifluoro-1-[methyl(prop-2-yn-1-yl)amino]ethyl}pyridin-4(1H)-one (Apo7057)

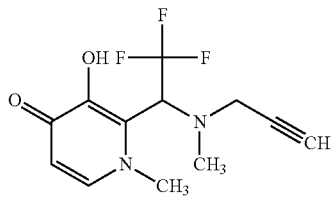

To 20 mL acetonitrile cooled in an ice-water bath was added DMF (0.42 mL, 5.4 mmol) followed by oxalyl chloride (0.47 mL, 5.4 mmol) dropwise. To this resulting suspension was added 3-hydroxy-1-methyl-2-(2,2,2-trifluoro-1-hydroxyethyl)pyridin-4(1H)-one (1.0 g, 4.5 mmol) in one portion. The mixture was then stirred for 2 h. Then, Et$_3$N (2.50 mL, 17.9 mmol) was added to this reaction mixture followed by N-methyl propargylamine (0.75 mL, 9.0 mmol). The reaction mixture was stirred at RT for overnight. The solid was filtered off, and the filtrate was concentrated to dryness. The residue was purified by flash chromatography on silica gel (5% MeOH in CH$_2$Cl$_2$ as eluant) to afford the title compound, Apo7057 (570 mg) as an orange powder. Yield=46.4%; $^1$H NMR (400 MHz, DMSO+a few drops of D$_2$O) δ (ppm): 7.6 (br. s., 1H), 6.25 (d, J=7.1 Hz, 1H), 5.15 (br. s., 1H), 3.87 (s, 3H), 3.37-3.67 (m, 2H), 3.23 (br. s., 1H), 232 (br. s., 3H); MS m/z 275 [M+1]$^+$, 206 (100%).

B. Preparation of 3-hydroxy-1-methyl-2-[2,2,2-trifluoro-1-(piperidin-1-yl)ethyl]pyridin-4(1H)-one (Apo7058)

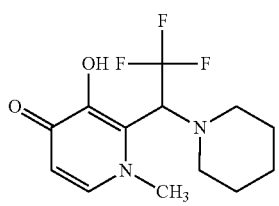 [SMILES: Cn1ccc(=O)c(O)c1C(N1CCCCC1)C(F)(F)F]

In a similar manner, Apo7058 was prepared from 3-hydroxy-1-methyl-2-(2,2,2-trifluoro-1-hydroxyethyl)pyridin-4(1H)-one (1.0 g, 4.5 mmol) and piperidine (0.88 mL, 8.9 mmol). The title compound Apo7058 (700 mg) was obtained as a white solid after purification by flash chromatography (4% MeOH in CH$_2$Cl$_2$ as eluant). Yield=54%; $^1$H NMR (400 MHz, DMSO-D6, 75° C.) δ (ppm): 7.59 (d, J=6.8 Hz, 1H), 6.19 (d, J=6.8 Hz, 1H), 4.82 (q, J=9.0 Hz, 1H), 3.88 (s, 3H), 2.46-2.84 (m, 4H), 1.29-1.74 (m, 6H) MS m/z 291 [M+1]+, 206 (100%).

C. Preparation of 3-hydroxy-1-methyl-2-[2,2,2-trifluoro-1-(4-methylpiperazin-1-yl)ethyl]pyridin-4(1H)-one (Apo7073)

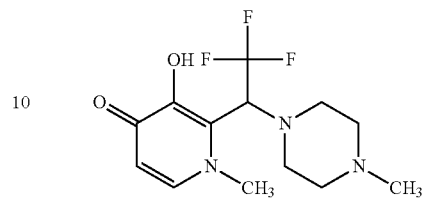

In a similar manner, Apo7073 was prepared from 3-hydroxy-1-methyl-2-(2,2,2-trifluoro-1-hydroxyethyl)pyridin-4(1H)-one (1.0 g, 4.5 mmol) and 1-methylpiperazine (1.0 mL, 9.0 mmol). The title compound Apo7073 (401 mg) was obtained after purification by Biotage reverse C$_{18}$ column. Yield=29%; $^1$H NMR (400 MHz, DMSO-d6, 75° C.) δ (ppm): 7.63 (d, J=6.8 Hz, 1H), 6.21 (d, J=7.4 Hz, 1H), 4.94 (q, J=8.5 Hz, 1H), 3.86 (s, 3H), 3.05 (br. s., 4H), 2.92 (br. s., 4H), 2.64 (s, 3H); MS m/z 306 [M+1]$^+$, 206 (100%).

D. Preparation of 2-[1-(cyclopropylamino)-2,2,2-trifluoroethyl]-3-hydroxy-1-methylpyridin-4(1H)-one (Apo7074)

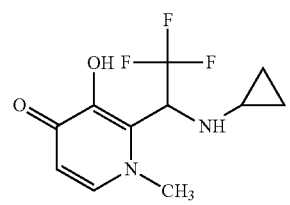 [SMILES: Cn1ccc(=O)c(O)c1C(NC1CC1)C(F)(F)F]

In a similar manner, Apo7074 was prepared from 3-hydroxy-1-methyl-2-(2,2,2-trifluoro-1-hydroxyethyl)pyridin-4(1H)-one (1.0 g, 4.5 mmol) and cyclopropylamine (0.62 mL, 9.0 mmol). The title compound Apo7074 (470 mg) was obtained after purification by flash chromatography (5% MeOH in CH$_2$Cl$_2$ as eluant). Yield=40%; $^1$H NMR (400 MHz, DMSO+a few drops of D$_2$O) δ (ppm): 7.67 (d, J=6.8 Hz, 1H), 6.25 (d, J=7.1 Hz, 1H), 4.70 (q, J=8.1 Hz, 1H), 3.74 (s, 3H), 2.04 (br. s., 1H), 0.34-0.43 (m, 4H); MS m/z 263 [M+1]$^+$, 206 (100%).

E. Preparation of 3-hydroxy-1-methyl-2-[2,2,2-trifluoro-1-(prop-2-en-1-ylamino)ethyl]pyridin-4(1H)-one (Apo7075)

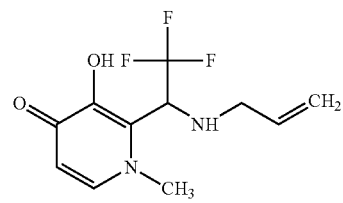 [SMILES: C=CCNC(c1c(O)c(=O)ccn1C)C(F)(F)F]

In a similar manner, Apo7075 was prepared from 3-hydroxy-1-methyl-2-(2,2,2-trifluoro-1-hydroxyethyl)pyridin-4

(1H)-one (1.0 g, 4.5 mmol) and allylamine (0.67 mL, 9.0 mmol). The title compound Apo7075 (497 mg) was obtained after purification by flash chromatography (5% MeOH in CH$_2$Cl$_2$ as eluant). Yield=42%; $^1$H NMR (400 MHz, DMSO+a few drops of D$_2$O) δ (ppm): 7.65 (d, J=7.1 Hz, 1H), 6.24 (d, J=7.4 Hz, 1H), 5.70-5.80 (m, 1H), 5.14 (d, J=17.4 Hz, 1H), 5.06 (d, J=10.1 Hz, 1H), 4.63 (q, J=8.2 Hz, 1H), 3.67 (s, 3H), 3.15-3.19 (m, 2H); MS m/z 263 [M+1]$^+$, 206 (100%).

Example 13

A. Preparation of 5-(benzyloxy)-3-chloro-2-methyl-pyridin-4(1H)-one

To a solution of 5-(benzyloxy)-2-methylpyridin-4(1H)-one (9.00 g, 41.8 mmol) in 2M sodium hydroxide (62.5 mL, 125 mmol) under ice-water bath, a solution of 10-14% sodium hypochlorite (62.5 mL) was added slowly during 20 minutes. The reaction mixture was stirred at room temperature for another hour. The reaction mixture was carefully neutralized with 6N HCl to pH about 7 with external cooling to keep the internal temperature below 25° C. The solid was filtered and washed with water (3×), then dried in a vacuum oven for overnight. Thus, 5-(benzyloxy)-3-chloro-2-methylpyridin-4(1H)-one (9.03 g) was obtained as a white solid. Yield=86%; $^1$H NMR (DMSO-D$_6$, 90 MHz) δ (ppm): 11.74 (br. s, 1H), 7.14-7.68 (m, 6H), 5.02 (s, 2H) and 2.33 (s, 3H).

B. Preparation of 5-(benzyloxy)-3-chloro-2-(hydroxymethyl)pyridin-4(1H)-one

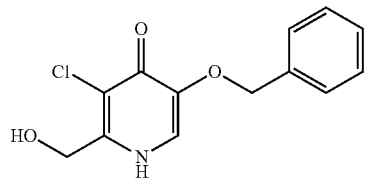 [SMILES: O=c1c(OCc2ccccc2)c[nH]c(CO)c1Cl]

In a similar manner, 5-(benzyloxy)-3-chloro-2-(hydroxymethyl)pyridin-4(1H)-one (10.50 g) was prepared from 5-(benzyloxy)-2-(hydroxymethyl)pyridin-4(1H)-one (11.56 g, 50 mmol) and a solution of 10-14% sodium hypochlorite (75 mL) in 2M sodium hydroxide (75 mL) solution. Yield=81%; $^1$H NMR (DMSO-D$_6$, 90 MHz) δ (ppm): 11.35 (br. s, 1H), 7.05-7.66 (m, 6H), 5.79-6.32 (m, 1H), 5.03 (s, 2H) and 4.54 (s, 2H).

C. Preparation of 5-(benzyloxy)-3-chloro-1,2-dimethylpyridin-4(1H)-one

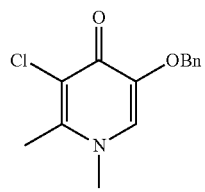 [SMILES: Cc1c(Cl)c(=O)c(OCc2ccccc2)cn1C]

5-(Benzyloxy)-3-chloro-2-methylpyridin-4(1H)-one (3.00 g, 12.0 mmol) was suspended in 25 mL of DMF.

Potassium carbonate (3.30 g, 24.0 mmol) was added followed by the addition of iodomethane (1.53 mL, 24.0 mmol). The progress of the reaction was monitored by TLC (30% ethyl acetate in hexanes). Upon completion, the reaction was allowed to stir at room temperature. Water was added and a white precipitate formed. The solid was collected by suction filtration, allowed to air dry and then further dried under vacuum. Thus, 5-(benzyloxy)-3-chloro-1,2-dimethylpyridin-4(1H)-one (2.00 g) was obtained. Yield=63%; $^1$H NMR (MeOD-D$_4$, 90 MHz,) δ (ppm): 7.61 (s, 1H), 7.27-7.46 (m, 5H), 5.21 (s, 2H), 3.75 (s, 3H) and 2.54 (s, 3H).

D. Preparation of 5-(benzyloxy)-3-chloro-2-(hydroxymethyl)-1-methylpyridin-4(1H)-one

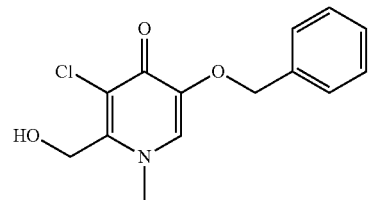 [SMILES: Cn1cc(OCc2ccccc2)c(=O)c(Cl)c1CO]

In a similar manner, 5-(benzyloxy)-3-chloro-2-(hydroxymethyl)-1-methylpyridin-4(1H)-one (7.52 g) was prepared from 5-(benzyloxy)-3-chloro-2-(hydroxymethyl)pyridin-4(1H)-one (10.0 g, 37.6 mmol), iodomethane (10.7 g, 75.2 mmol) and potassium carbonate (10.3 g, 75.2 mmol) in DMF (50 mL). Yield=72%; $^1$H NMR (DMSO-D$_6$, 90 MHz) δ (ppm): 7.77 (s, 1H), 7.17-7.58 (m, 5H), 5.65 (br. s, 1H), 5.04 (s, 2H), 4.70 (br. s, 2H) and 3.81 (s, 3H).

E. Preparation of 5-(benzyloxy)-3-chloro-1-methyl-4-oxo-1,4-dihydropyridine-2-carboxylic acid

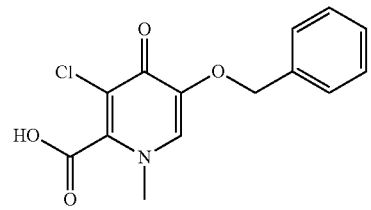 [SMILES: Cn1cc(OCc2ccccc2)c(=O)c(Cl)c1C(=O)O]

To a mixture of 5-(benzyloxy)-3-chloro-2-(hydroxymethyl)-1-methylpyridin-4(1H)-one (4.90 g, 17.5 mmol), TEMPO (120 mg, 0.77 mmol) and potassium bromide (120 mg, 1.00 mmol) in acetone (50 mL) and saturated sodium bicarbonate (40 mL) below 7° C. was added dropwise a 10-14% sodium hypochlorite (50 mL) solution during 30 minutes. After being stirred for 2 hours, the reaction mixture was diluted with water and adjusted to pH about 1.5 with 6N HCl. The solid was filtered and washed with water to give 5-(benzyloxy)-3-chloro-1-methyl-4-oxo-1,4-dihydropyridine-2-carboxylic acid (2.89 g) as a white solid. Yield=56%; $^1$H NMR (DMSO-D$_6$, 90 MHz) δ (ppm): 7.79 (s, 1H), 7.16-7.62 (m, 5H), 5.03 (s, 2H) and 3.67 (s, 3H); MS m/z 294 [M+1]$^+$.

F. Preparation of 3-(benzyloxy)-5-chloro-1-methyl-pyridin-4(1H)-one

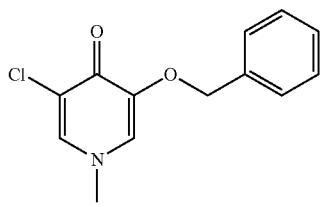 [SMILES: Cn1cc(Cl)c(=O)c(OCc2ccccc2)c1]

5-(Benzyloxy)-3-chloro-1-methyl-4-oxo-1,4-dihydro-pyridine-2-carboxylic acid (3.50 g, 11.9 mmol) was heated in DMF (10 mL) for one hour. The reaction mixture was concentrated by rotary evaporation and the residue was triturated with ethyl acetate/ether to give 3-(benzyloxy)-5-chloro-1-methylpyridin-4(1H)-one (2.80 g) as a pale brown solid. Yield=94%; $^1$H NMR (DMSO-D$_6$, 90 MHz) δ (ppm): 8.08 (d, J=1.8 Hz, 1H), 7.68 (d, J=1.8 Hz, 1H), 7.19-7.58 (m, 5H), 5.01 (s, 2H) and 3.67 (s, 3H).

Example 14

A. Preparation of 3-chloro-5-hydroxy-1-methylpyridin-4(1H)-one

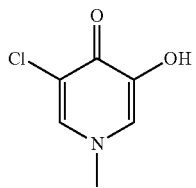

3-(Benzyloxy)-5-chloro-1-methylpyridin-4(1H)-one (2.70 g, 10.8 mmol) was mixed in 6N HCl (15 mL) and ethanol (10 mL). After being refluxed for 2 hours, the reaction mixture was concentrated by rotary evaporator. The residue was mixed with water (5 mL) and basified to pH 8-9 with concentrated ammonia. An off-white precipitate came out, ant the mixture was again concentrated in vacuo to remove volatiles. The off-white solid was collected by suction filtration and dried to give 3-chloro-5-hydroxy-1-methylpyridin-4(1H)-one (1.32 g). Yield=76.6%; $^1$H NMR (DMSO-D$_6$, 90 MHz) δ (ppm): 7.98 (s, 1H), 7.47 (s, 1H) and 3.67 (s, 3H).

B. Preparation of 3-chloro-5-hydroxy-1,2-dimethylpyridin-4(1H)-one

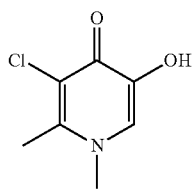

In a similar manner, 3-chloro-5-hydroxy-1,2-dimethyl-pyridin-4(1H)-one (600 mg), was prepared by refluxing a mixture of 5-(benzyloxy)-3-chloro-1,2-dimethylpyridin-4(1H)-one (2.00 g, 7.6 mmol) with 6N HCl (20 mL) and methanol (10 mL) at 100° C. for 2 hours. Yield=46%; $^1$H NMR (MeOD-D$_4$, 90 MHz) δ (ppm): 8.08 (s, 1H) 4.08 (s, 3H) and 2.72 (s, 3H); MS m/z 174 [M+1]$^+$.

Example 15

A. Preparation of 3-chloro-5-hydroxy-1,2-dimethyl-6-(2,2,2-trifluoro-1-hydroxyethyl)pyridin-4(1H)-one

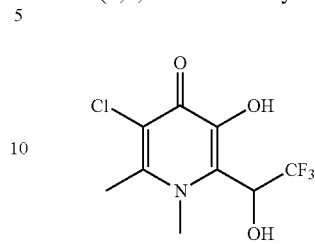

3-Chloro-5-hydroxy-1,2-dimethylpyridin-4(1H)-one (500 mg, 2.80 mmol) was suspended in trifluoroacetaldehyde methyl hemiacetal (3 mL). Potassium carbonate (119 mg, 0.86 mmol) was added and the mixture was heated to 120° C. After 2.5 hours, the reaction mixture was allowed to cool to room temperature, then diluted with methanol and filtered. The filtrate was concentrated to dryness and diluted with acetone. The solution was filtered and the filtrate was concentrated to give 3-chloro-5-hydroxy-1,2-dimethyl-6-(2,2,2-trifluoro-1-hydroxyethyl)pyridin-4(1H)-one (650 mg) as a pink solid. Yield=85%; $^1$H-NMR (MeOD-D$_4$, 90 MHz) δ (ppm): 5.9 (q, J=9.1 Hz, 1H), 4.01 (s, 3H) and 2.65 (s, 3H); MS-ESI m/z 272 [M+1]$^+$.

B. Preparation of 6-chloro-3-hydroxy-1-methyl-2-(2,2,2-trifluoro-1-hydroxyethyl)pyridin-4(1H)-one

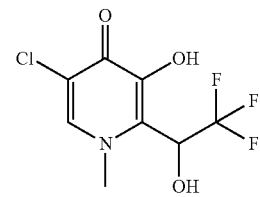 [SMILES: Cn1cc(Cl)c(=O)c(O)c1C(O)C(F)(F)F]

In a similar manner, 5-chloro-3-hydroxy-1-methyl-2-(2,2,2-trifluoro-1-hydroxyethyl)pyridin-4(1H)-one (1.40 g) was prepared from 3-chloro-5-hydroxy-1-methylpyridin-4(1H)-one (1.27 g, 8.0 mmol) and trifluoroacetaldehyde methyl hemiacetal (12.7 mL) in presence of potassium carbonate (0.22 g, 1.6 mmol). Yield=68%; $^1$H NMR (DMSO-D$_6$) δ (ppm): 8.10 (s, 1H), 5.80 (q, J=8.7 Hz, 1H) and 3.88 (s, 3H); MS m/z 258 [M+1]$^+$.

Example 16

A. Preparation of 3-chloro-6-hydroxy-1,2-dimethyl-6-(2,2,2-trifluoroethyl)pyridin-4(1H)-one

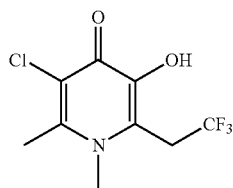 [SMILES: Cc1c(Cl)c(=O)c(O)c(CC(F)(F)F)n1C]

3-Chloro-5-hydroxy-1,2-dimethyl-6-(2,2,2-trifluoro-1-hydroxyethyl)pyridin-4(1H)-one (300 mg, 1.10 mmol) was suspended in 10 mL of acetonitrile and thionyl chloride (398 μL, 5.50 mmol) was added dropwise. The reaction was stirred at room temperature. After 2 hours, the reaction was concentrated. The crude was diluted with 10 mL of methanol and sodium borohydride (329 mg, 8.80 mmol) was added in small portions. After 15 hours, the reaction was filtered and the filtrate was concentrated in vacuo. The resulting solid was dissolved in methanol and ethyl acetate added, filtered and concentrated. The crude product was purified by column chromatography on silica gel using a mixture of 30% EtOAc in MeOH as eluant. Fractions rich in product were combined and evaporated to dryness. The residue product was recrystallised from methanol/ethyl acetate to give 3-chloro-5-hydroxy-1,2-dimethyl-6-(2,2,2-trifluoroethyl)pyridin-4(1H)-one (172 mg) as a white solid. Yield=61%; $^1$H NMR (MeOD-D$_4$, 90 MHz) δ (ppm): 4.1 (q, J=9.0 Hz, 2H), 3.99 (s, 3H) and 2.77 (s, 3H); MS m/z 256 [M+1]$^+$.

B. Preparation of 5-chloro-3-hydroxy-1-methyl-2-(2,2,2-trifluoroethyl)pyridin-4(1H)-one

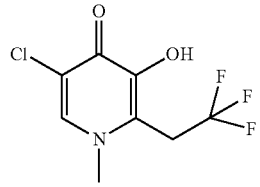

In a similar manner, 5-chloro-3-hydroxy-1-methyl-2-(2,2,2-trifluoroethyl)pyridin-4(1H)-one (117 mg) was prepared from 5-chloro-3-hydroxy-1-methyl-2-(2,2,2-trifluoro-1-hydroxyethyl)pyridin-4(1H)-one (580 mg, 2.30 mmol). Yield=22%; $^1$H NMR (MeOD-D$_4$, 90 MHz) δ (ppm): 8.04 (s, 1H), 3.91 (q, J=9.9 Hz, 2H) and 3.84 (s, 3H); MS m/z 242 [M+1]$^+$.

Example 17

A. Preparation of 3-chloro-6-[1-(dimethylamino)-2,2,2-trifluoroethyl]-5-hydroxy-1,2-dimethylpyridin-4(1H)-one

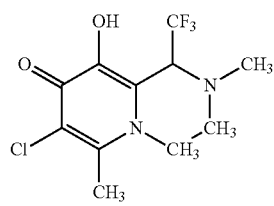 [SMILES: Cc1c(Cl)c(=O)c(O)c2n1CCN(C)C2C(F)(F)F]

3-Chloro-5-hydroxy-1,2-dimethyl-6-(2,2,2-trifluoro-1-hydroxyethyl)pyridin-4(1H)-one (618 mg, 2.3 mmol) was mixed with pyridine (276 μL, 3.4 mmol) in acetonitrile (10 mL) at room temperature. Thionyl chloride (249 μL, 3.41 mmol) was added dropwise. After being stirred at room temperature for 30 minutes, the reaction mixture was concentrated by rotary evaporation. The residue was dried under vacuum and then mixed with ethanol (20 mL) under ice-water bath. An ethanolic dimethylamine (5.6 M, 4.06 mL, 22.8 mmol) solution was added at about 5° C. and the mixture was stirred for 20 minutes. The reaction mixture was concentrated by rotary evaporation. The residue was mixed with water (10 mL) and the pH of the solution was adjusted to 5.5. The precipitated solid was collected by suction filtration, and washed with water, then triturated with ether/hexanes to give 3-chloro-6-[1-(dimethylamino)-2,2,2-trifluoroethyl]-5-hydroxy-1,2-dimethyl pyridin-4(1H)-one (380 mg) as an off-white solid. Yield=56%; $^1$H NMR (CDCl$_3$, 90 MHz) δ (ppm): 4.88 (q, J=8.6 Hz, 1H), 4.08 (s, 3H), 2.65-2.81 (m, 3H) and 2.39 (s, 6H); MS m/z 299 [M+1]+.

B. Preparation of 5-chloro-2-(1-(dimethylamino)-2,2,2-trifluoroethyl)-3-hydroxy-1-methylpyridin-4(1H)-one

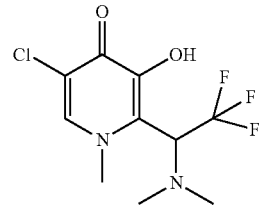 [SMILES: CN(C)C(c1c(O)c(=O)c(Cl)cn1C)C(F)(F)F]

In a similar manner, 5-chloro-2-(1-(dimethylamino)-2,2,2-trifluoroethyl)-3-hydroxy-1-methylpyridin-4(1H)-one (290 mg) was prepared from 5-chloro-3-hydroxy-1-methyl-2-(2,2,2-trifluoro-1-hydroxyethyl)pyridin-4(1H)-one (386 mg, 1.5 mmol). Yield=68%; $^1$H NMR (MeOD-D$_4$, 90 MHz) δ (ppm): 8.04 (s, 1H), 4.69-4.85 (m, 1H), 4.05 (br. s, 3H) and 2.42 (br. s, 6H); MS m/z 285 [M+1]$^+$.

C. Preparation of 5-chloro-3-hydroxy-1-methyl-2-(2,2,2-trifluoro-1-(piperidin-1-yl)ethyl)pyridin-4(1H)-one

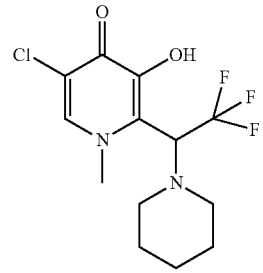 [SMILES: Cn1cc(Cl)c(=O)c(O)c1C(N1CCCCC1)C(F)(F)F]

In a similar manner, 5-chloro-3-hydroxy-1-methyl-2-(2,2,2-trifluoro-1-(piperidin-1-yl)ethyl)pyridin-4(1H)-one (302 mg) was prepared from 5-chloro-3-hydroxy-1-methyl-2-(2,2,2-trifluoro-1-hydroxyethyl)pyridin-4(1H)-one (386 mg, 1.5 mmol). Yield=60%; $^1$H NMR (MeOD-D$_4$, 90 MHz) δ (ppm): 8.03 (br. s, 1H), 4.57-4.83 (m, 1H), 3.74-4.35 (m, 3H), 2.21-3.02 (m, 4H) and 1.44-1.89 (m, 6H); MS m/z 325 [M+1]$^+$.

Example 18

A. Preparation of 2-(2,2-difluoro-1-hydroxyethyl)-3-hydroxy-1-methylpyridin-4(1H)-one (Apo7078)

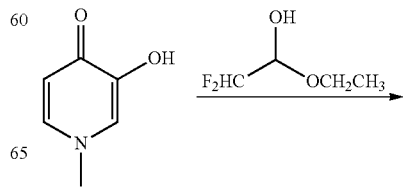

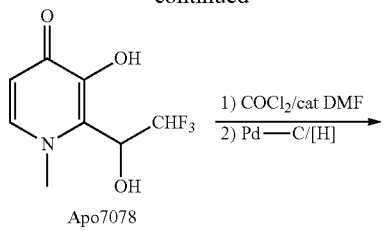

Apo7078

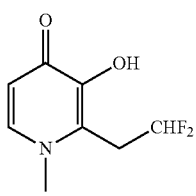

Apo7080

A sealed suspension of 3-hydroxy-1-methylpyridin-4 (1H)-one (1.00 g, 8.0 mmol) and potassium carbonate (0.11 g, 0.8 mmol) in 2.4 mL of difluroacetaldehyde ethyl hemiacetal was heated to 50° C. for 18 h. The volatile components were evaporated under reduced pressure. The residue was dissolved in 3 mL of de-ionized water then cooled in an ice-water bath, and the pH was adjusted to 5-6 with a 1N HCl solution. The precipitate was collected by suction filtration and dried. Thus, the title compound Apo7078 was obtained (410 mg) as a white solid. Yield=25%; $^1$H NMR (400 MHz, CD$_3$OD) δ (ppm): 7.62 (d, J=7.1 Hz, 1H), 6.41 (d, J=7.1 Hz, 1H), 6.30 (dt, $^3$J=55.8 Hz, $^2$J=5.1 Hz, 1H), 5.45 (dt, $^2$J=5.1 Hz, $^3$J=11.4 Hz, 1H), 3.96 (s, 3H); MS m/z 206 [M+1]$^+$, 188 (100%).

B. Preparation of 2-(2,2-difluoroethyl)-3-hydroxy-1-methylpyridin-4(1H)-one (Apo7080)

To 10 mL of acetonitrile at ice-water bath was added DMF (0.14 mL, 1.8 mmol) followed by oxalyl chloride (0.15 mL, 1.8 mmol) dropwise. To this resulting suspension was added 2-(2,2-difluoro-1-hydroxyethyl)-3-hydroxy-1-methylpyridin-4(1H)-one (0.30 g, 1.5 mmol) in one portion, and the resulting mixture was stirred for 2 h. A solid was collected by filtration, and it was dissolved in 150 mL of acetonitrile. To this resulting solution was added Pd/C (10%, wet, 0.20 g, 66.7% w/w), and the mixture was subjected to hydrogenation under 40 psi hydrogen pressure for 2 h. The catalyst was filtered off, and the filtrate was evaporated to dryness. The residue was dissolved in de-ionized water, and the pH was adjusted to 5-6 using a 6N NaOH solution. The precipitate was collected via suction filtration to afford the crude product (100 mg) as an off-white solid. The crude was further purified by Biotage using reversed phase C18 cartridge to afford the title compound, Apo7080 (66 mg) as white solid. Yield=24%; $^1$H NMR (400 MHz, CD$_3$OD) δ (ppm): 7.65 (d, J=7.2 Hz, 1H), 6.41 (d, J=7.2 Hz, 1H), 6.19 (tt, J=56.5, 4.7 Hz, 1H), 3.83 (s, 3H), 3.51 (dt, $^3$J=15.9 Hz, $^2$J=4.6 Hz, 2H); MS m/z 190 [M+1]$^+$, 188 (100%).

Example 19

Preparation of N-2-{[5-hydroxy-1-methyl-4-oxo-6-(2,2,2-trifluoro-1-hydroxyethyl)-1,4-dihydropyridin-2-yl]methyl}-N-methyl-L-alaninamide (Apo7033)

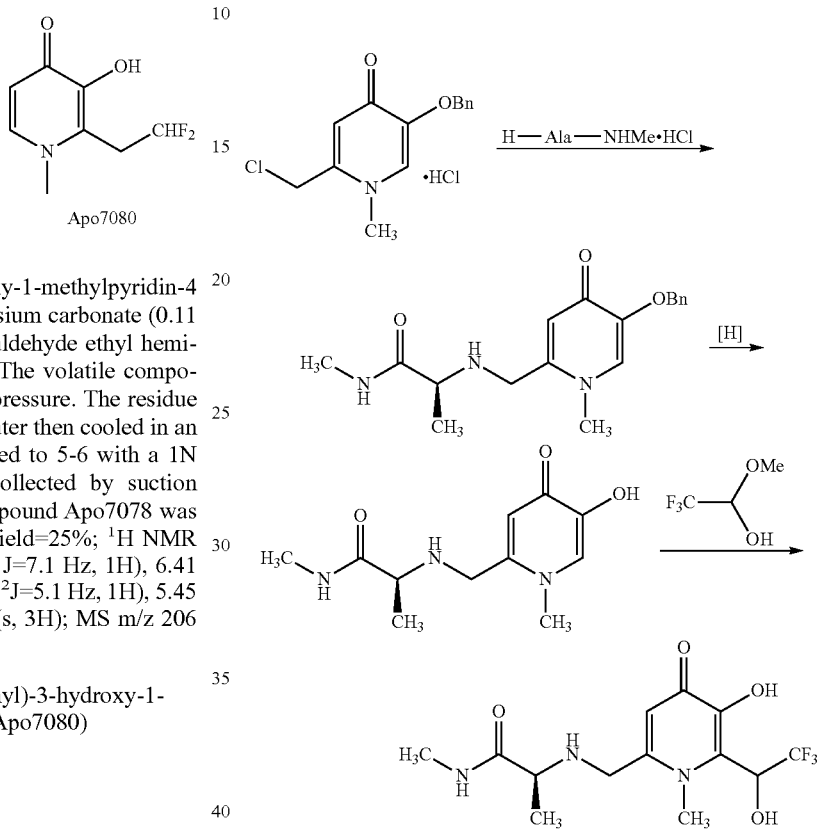

Apo7033

A mixture of 5-(benzyloxy)-2-(chloromethyl)-1-methylpyridin-4(1H)-one hydrochloride (7.55 g, 25.0 mmol), H-Ala-NHMe.HCl (5.14 g, 37.0 mmol) and diisopropylethylamine (12.5 mL, 72.0 mmol) in CH$_3$CN (50 mL) was heated at 85° C. under a nitrogen atmosphere for overnight. Volatiles were removed in vacuo, and the residue was pre-purified by column chromatography on silica gel using a mixture of MeOH and ethyl acetate as eluant (solvent gradient of 10, 15 and 20% MeOH in ethyl acetate). The fractions rich in product were combined and evaporated to dryness. Further purification by column chromatography on silica gel using a mixture of H$_2$O and CH$_3$CN (1-5% H$_2$O content) and then a 10% MeOH in dichloromethane solution afforded (S)-2-((5-(benzyloxy)-1-methyl-4-oxo-1,4-dihydropyridin-2-yl)methylamino)-N-methylpropanamide (7.17 g) in 87% yield. MS m/z 352 [M+Na]$^+$, 330 (100%) [M+1]$^+$, 228, 138, 91.

A mixture of (S)-2-((5-(benzyloxy)-1-methyl-4-oxo-1,4-dihydropyridin-2-yl)methylamino)-N-methylpropanamide (7.04 g, 21.4 mmol) and 10% Pd/C (0.90 g) in MeOH (70 mL) was subjected to hydrogenation in a Parr apparatus at 50 psi of hydrogen pressure for 2 h. The reaction mixture was filtered over celite and the filtrate was concentrated in vacuo. The resulting solid was dried in a vacuum oven at 44°

C. for overnight. Thus, (S)-2-((5-hydroxy-1-methyl-4-oxo-1,4-dihydropyridin-2-yl)methylamino)-N-methylpropanamide was obtained as an orange solid (4.90 g) in 96% yield. $^1$H NMR (CD$_3$COOD) δ (ppm): 7.77 (s, 1H), 7.03 (s, 1H), 4.30-4.34 (m, 3H, OCH$_2$+CHCH$_3$), 3.98 (s, 3H), 2.80 (s, 3H), 1.56 (d, J=6.3 Hz, 3H, CHCH$_3$); MS m/z 262 [M+Na]$^+$, 240 (100%) [M+1]$^+$, 138, 110.

A mixture of (S)-2-((5-hydroxy-1-methyl-4-oxo-1,4-dihydropyridin-2-yl)methylamino)-N-methylpropanamide (3.13 g, 13.1 mmol), trifluoroacetaldehyde methyl hemiacetal (3.6 mL, 38.0 mmol) and potassium carbonate (2.62 g, 19.0 mmol) in CH$_3$CN (35 mL) was heated at 75-80° C. for overnight. Analysis of the reaction mixture by TLC using a solvent mixture of 28-30% conc. NH$_4$OH in IPA as eluant indicated incomplete consumption of the starting material. A further portion of trifluoroacetaldehyde methyl hemiacetal (4 mL) was added, and the mixture was heated at 95-100° C. for another 24 h. On cooling to room temperature, the mixture was purified by column chromatography on silica gel using a mixture of MeOH and ethyl acetate as eluant (solvent gradient of 10, 15 and 20% MeOH in ethyl acetate). Thus, the title compound N-2-{[5-hydroxy-1-methyl-4-oxo-6-(2,2,2-trifluoro-1-hydroxyethyl)-1,4-dihydropyridin-2-yl] methyl}-N-methyl-L-alaninamide, Apo7033, was obtained as a yellowish solid (1.53 g) in 35% yield. $^1$H NMR (DMSO-D$_6$) δ (ppm): 7.79 (t, J=4.4 Hz, 1H, NH), 6.30 (s, 1H), 5.87 (q, J=8.7 Hz, 1H, CHCF$_3$), 3.82 (s, 3H, NCH$_3$), 3.61-3.65 (dd, $^2$J=14.5 and $^4$J=1.9 Hz, 1H, 0.5 NHCH$_2$), 3.47-3.52 (apparent t, J=15.2 Hz, 1H, 0.5 NHCH$_2$), 3.08 (q, J=6.8 Hz, 1H, CHCH$_3$), 2.59 (d, J=4.2 Hz, 3H, NHCH$_3$), 1.12 (dd, $^2$J=6.8 and $^4$J=2.3 Hz, 3H, CHCH$_3$); $^{13}$C NMR (DMSO-D$_6$) δ (ppm): 175.0 (C=O), 169.6 (C=O), 149.2, 147.3, 125.6, 125.0 (q, J=283 Hz, CHCF$_3$), 113.1 (CH), 65.2 (q, J=33 Hz, CHCF$_3$), 56.9 (CH), 48.9 (CH$_2$), 36.6 (NCH$_3$), 25.8 (NHCH$_3$), 19.6 (CH$_3$); MS m/z 360 [M+Na]$^+$, 338 (100%) [M+1]$^+$, 236.

Example 20

N-{[5-hydroxy-1-methyl-4-oxo-6-(2,2,2-trifluoro-1-hydroxyethyl)-1,4-dihydropyridin-2-yl]m ethyl}-L-alanine (Apo7032)

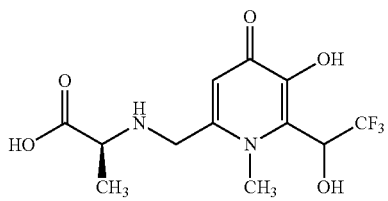 [SMILES: C[C@H](NCc1cc(=O)c(O)c(C(O)C(F)(F)F)n1C)C(=O)O]

The experiment in the last step of the previous example (example 19) was repeated (2.9 mmol scale) except that the mixture was purified by column chromatography on silica gel using a mixture of 28-30% conc. NH$_4$OH and IPA as eluant (solvent gradient of 10, 15 and 20 and 25% NH$_4$OH in IPA). In this case, the title acid compound N-{[5-hydroxy-1-methyl-4-oxo-6-(2,2,2-trifluoro-1-hydroxyethyl)-1,4-dihydropyridin-2-yl]methyl}-L-alanine (Apo7032) was obtained as an orange solid (0.7 g) in 78% yield. MS m/z 347 [M+Na]$^+$, 325 (100%) [M+1]$^+$, 236.

Example 21

Preparation of the diastereoisomers of N-methyl-2-[2,2,2-trifluoro-1-(5-hydroxy-6-methyl-4-oxo-1,4-dihydro-pyridin-3-yl)-ethylamino]-propionamide (Apo6884 and Apo6885)

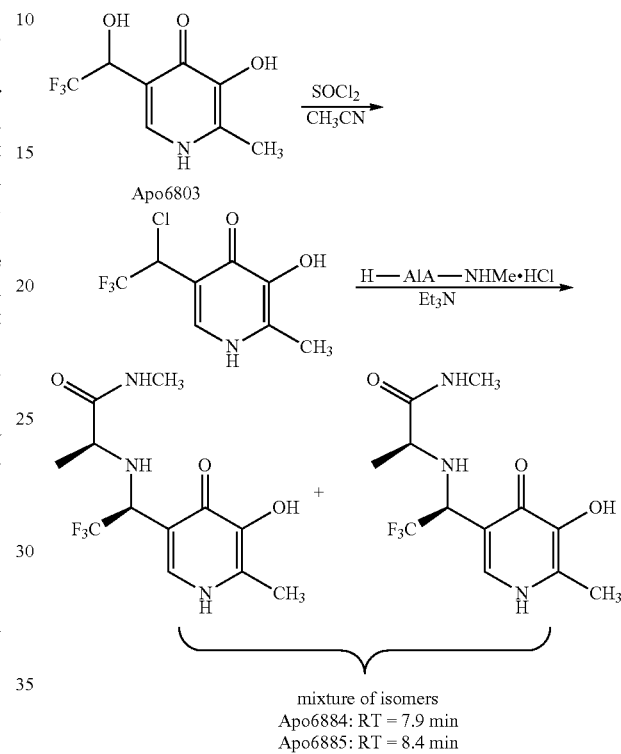

mixture of isomers
Apo6884: RT = 7.9 min
Apo6885: RT = 8.4 min

Thionyl chloride (2.5 mL, 33.7 mmol) was added to a suspension of 3-hydroxy-2-methyl-5-(2,2,2-trifluoro-1-hydroxy-ethyl)-1H-pyridin-4-one (1.50 g, 6.7 mmol) in acetonitrile (33 mL) at room temperature. The resulting mixture was stirred for 30 min as a clear solution resulted. The progress of the reaction was monitored by TLC (methanol:dichloromethane, 1:10, v:v), which indicated consumption of the starting material. The reaction mixture was evaporated to dryness to give crude 5-(1-chloro-2,2,2-trifluoro-ethyl)-3-hydroxy-2-methyl-1H-pyridin-4-one as a solid.

The solid was dissolved in acetonitrile (35 mL), and H-Ala-NHMe hydrochloric acid salt (1.15 g, 8.3 mmol) was added followed by triethylamine (4.0 mL, 28.7 mmol). The heterogeneous mixture was stirred for 60 min, while the progress of the reaction was monitored by HPLC Method 1. HPLC analysis of the crude reaction mixture indicated the presence of two product peaks in a ratio of about 4/3, and with RT of 7.9 and 8.4 min, respectively. The reaction mixture was filtered to remove solid materials, and the filtrate was evaporated to dryness to give a solid. The solid was dissolved in ethyl acetate, and the organic solution was extracted with a 20% ammonium chloride solution (3×40 mL). The aqueous fractions were combined (pH 6) and the pH was adjusted to 7 with a NaOH solution. The aqueous solution was then extracted with ethyl acetate (2×50 mL). The ethyl acetate fractions were combined and evaporated to dryness to give N-methyl-2-[2,2,2-trifluoro-1-(5-hydroxy-6- methyl-4-oxo-1,4-dihydro-pyridin-3-yl)-ethylamino]-propionamide as a pair of diastereoisomers (850 mg, 41% yield, HPLC Method: Column: XTerra MS C18, 4.6×250 mm; A=Aqueous phase: 4 mM Tris, 2 mM EDTA, pH 7.4; B=Organic phase: $CH_3CN$; Flow rate=1.0 mL/min; Injection volume=5 μL; Wavelength (λ): 220, 254, 280, 450 nm. Gradient method; min-B % 0-5, 15-55, 25-55, 25.05-5, 30-5. Apo6884, RT=7.9 min, AUC=44% at λ=280 nm, and Apo6885, RT=8.4 min, AUC=35% at λ=280 nm). Samples of the two diastereoisomers were obtained after repeated purification using the Biotage© system (C18 reverse phase cartridge; a mixture of acetonitrile and de-ionized water as eluant; gradient elution). Apo6884: 82 mg, RT=7.9 min, HPLC purity (AUC): 99% at λ=280 nm; $^1$H NMR (DMSO-$D_6$) δ (ppm): 11.59 (br s, 1H), 7.74 (br s, 1H), 7.56 (s, 1H), 4.62 (m, 1H), 3.12 (m, 2H), 2.49 (s, 3H), 2.18 (s, 3H), 1.09 (d, J=6.3 Hz, 3H); MS-ESI m/z 308 $[M+1]^+$, 249, 206 (100%), 103. Apo6885: 95 mg, RT=8.4 min, HPLC purity (AUC): 99% at λ=280 nm; $^1$H NMR (DMSO-$D_6$) δ (ppm): 11.65 (br s, 1H), 7.67 (s, 1H), 7.63 (br s, 1H), 4.43 (m, 1H), 3.39 (m, 1H), 2.93 (m, 1H), 2.62 (d, J=4.7 Hz, 3H), 2.18 (s, 3H), 1.07 (d, J=6.9 Hz, 3H); MS-ESI m/z 308.0 $[M+1]^+$, 249, 206 (100%), 103.

Example 22

Preparation of 5-[1-(dimethylamino)-2,2,2-trifluoroethyl]-3-hydroxy-1,2-dimethylpyridin-4(1H)-one (Apo7053)

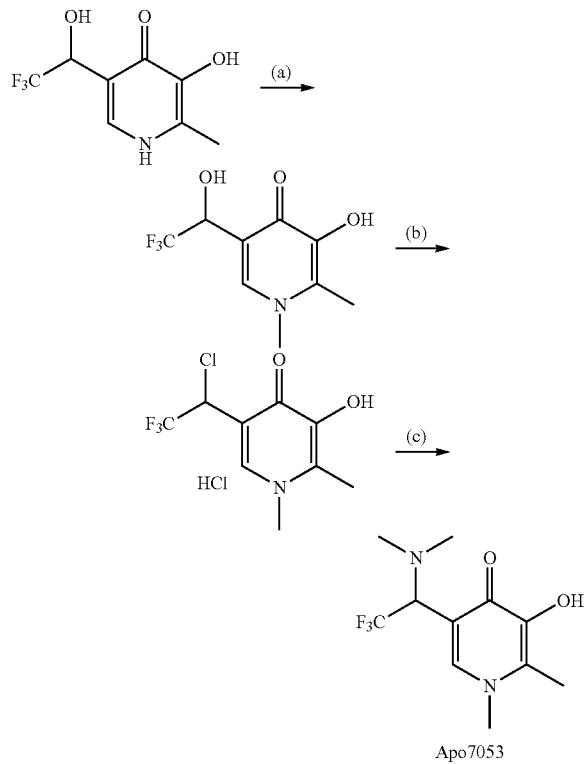

Apo7053

(a) To a suspension of 3-hydroxy-2-methyl-5-(2,2,2-trifluoro-1-hydroxyethyl)pyridin-4(1H)-one (5.33 g, 23.9 mmol) and acetonitrile (50 mL) was added potassium carbonate (4.96 g, 35.9 mmol). The mixture was stirred at room temperature and iodomethane (15 mL, 239.8 mmol) was added. The progress of the reaction was monitored by HPLC (Column: XTerra MS C18, 4.6×250 mm; A=Aqueous phase: 4 mM Tris, 2 mM EDTA, pH 7.4; B=Organic phase: $CH_3CN$; Flow rate=1.0 mL/min; Injection volume=5 μL; Wavelength (λ): 220, 254, 280, 450 nm. Gradient method; min-B % 0-5, 15-55, 25-55, 25.05-5, 30-5.

After stirring at room temperature for 1 h, HPLC analysis of the reaction mixture indicated about 80% conversion. The reaction mixture was filtered. Both the solid and the filtrate were collected. The solid was washed with acetonitrile (40 mL×2), followed by DI water and finally with ether to give 3-hydroxy-1,2-dimethyl-5-(2,2,2-trifluoro-1-hydroxyethyl)pyridin-4(1H)-one. Crop 1, 1.14 g, Yield=20%.

The filtrate was combined with the acetonitrile washing solutions and concentrated to dryness to give a solid. This solid was washed with DI water and ether to give a second crop of the desired product (2.46 g, 44%). Total yield (crops 1 and 2)=64%; $^1$H NMR ($CD_3OD$) δ (ppm): 7.79 (s, 1H), 5.43 (q, J=7.2 Hz, 1H), 3.88 (s, 3H), 2.44 (s, 3H).

(b) Thionyl chloride (7.5 mL, 102.7 mmol) was added dropwise to a suspension of 3-hydroxy-1,2-dimethyl-5-(2,2,2-trifluoro-1-hydroxyethyl)pyridin-4(1H)-one (3.00 g, 12.7 mmol) and acetonitrile (110 mL) with external cooling using a tap water bath under a blanket of nitrogen. The progress of the reaction was monitored by TLC (eluant: methanol:dichloromethane, 1:10, v:v). After the addition of $SOCl_2$, a clear solution resulted, and white solid gradually formed upon further stirring. The reaction mixture was concentrated repeatedly in acetonitrile to give a solid, which was then collected and washed with acetonitrile (15 mL×2). Thus, 5-(1-chloro-2,2,2-trifluoroethyl)-3-hydroxy-1,2-dimethylpyridin-4(1H)-one hydrochloride, was obtained as a white solid (2.89 g). Yield=78%; $^1$H NMR (DMSO-$D_5$) δ (ppm): 8.17 (s, 1H), 6.19 (q, J=7.5 Hz, 1H), 3.84 (s, 3H), 2.35 (s, 3H).

(c) A mixture of 5-(1-chloro-2,2,2-trifluoroethyl)-3-hydroxy-1,2-dimethylpyridin-4(1H)-one hydrochloride (395 mg, 1.4 mmol) and acetonitrile (30 mL) was added to a 40 wt % dimethylamine in water (3.5 mL, 27.7 mmol). The resulting yellowish solution was stirred vigorously, and the progress of the reaction was monitored by TLC (eluant: methanol/dichloromethane, 1/10, v/v). The starting material was completely consumed within 5 min. The reaction mixture was concentrated to give a solid. The solid was dissolved in dichloromethane (30 mL), which was then washed with a 10% ammonium chloride solution (15 mL×2). The organic phase was dried over sodium sulfate, filtered, and concentrated to give 5-[1-(dimethylamino)-2,2,2-trifluoroethyl]-3-hydroxy-1,2-dimethylpyridin-4(1H)-one (Apo7053) as a solid product (200 mg). Yield=56%; HPLC Method 1, RT=10.2 min, HPLC purity (AUC): 98.3% at 280 nm); $^1$H NMR (DMSO-$D_6$) δ (ppm): 7.68 (s, 1H), 4.86 (q, J=10.1 Hz, 1H), 3.73 (s, 3H), 2.29 (s, 3H), 2.23 (s, 6H). MS-ESI m/z 265 $[M+1]^+$, 220 (100%), 192.

In a similar manner, the following compounds were prepared:

(i) 3-Hydroxy-1,2-dimethyl-5-[2,2,2-trifluoro-1-(piperidin-1-yl)ethyl]pyridin-4(1H)-one (Apo7054) was prepared from the reaction of 5-(1-chloro-2,2,2-trifluoroethyl)-3-hydroxy-1,2-dimethylpyridin-4(1H)-one hydrochloride (304 mg, 1.0 mmol) and piperidine (2.0 mL, 20.3 mmol). The reaction was completed within 20 min, and Apo7054 was obtained as a solid product (232 mg). Yield=73%; HPLC Method 1, purity (AUC)=99.4% at 280 nm; $^1$H NMR (DMSO-$D_6$) δ (ppm): 7.66 (s, 1H), 4.83-4.94 (m, 1H), 3.71 (s, 3H), 2.56 (m, 2H), 2.41 (m, 2H), 2.27 (s, 3H), 1.46 (br, 4H), 1.28 (br, 2H); MS-ESI m/z 305 $[M+1]^+$ (100%), 220.

(ii) 3-Hydroxy-1,2-dimethyl-5-[2,2,2-trifluoro-1-(1H-imidazol-1-yl)ethyl]pyridin-4(1H)-one (Apo7055) was prepared from 5-(1-chloro-2,2,2-trifluoroethyl)-3-hydroxy-1,2-dimethylpyridin-4(1H)-one hydrochloride (505 mg, 1.7 mmol) and imidazole (3.5 g, 51.4 mmol). The reaction was stopped when analysis of the HPLC chromatogram (Method 1) of the reaction mixture indicated higher than 98% conversion. The reaction mixture was concentrated to give a solid. The solid was dissolved in de-ionized water (4 mL), and the pH of the solution was adjusted to 6.5 with a 6.00 N hydrochloric acid solution. The resulting solution was repeatedly extracted with dichloromethane (15 mL×4, 30 mL×2). The organic fractions were combined, dried over sodium sulfate, filtered, and concentrated. The desired compound Apo7055 was obtained as a solid from dichloromethane (320 mg). Yield=64%; HPLC purity (AUC): 99.7% at 280 nm); $^1$H NMR (DMSO-D$_6$) δ (ppm): 8.15 (s, 1H), 7.98 (s, 1H), 7.52 (s, 1H), 6.96 (s, 1H), 6.66 (q, J=9.1 Hz, 1H), 3.76 (s, 3H), 2.29 (s, 3H). MS-ESI m/z 288 [M+1]$^+$, 220 (100%).

(iii) 3-Hydroxy-1,2-dimethyl-5-[2,2,2-trifluoro-1-(methylamino)ethyl]pyridin-4(1H)-one (Apo7056) was prepared from 5-(1-chloro-2,2,2-trifluoroethyl)-3-hydroxy-1,2-dimethylpyridin-4(1H)-one hydrochloride (400 mg, 1.4 mmol) and methylamine (3.0 mL, 34.4 mmol). The reaction was essentially completed within 15 min. The reaction mixture was concentrated to give a solid. A sample of salt free Apo7056 product was obtained by purification using the Biotage© instrument (C18 reversed phase; eluant: water and acetonitrile; gradient, 100:0 to 100:4). (48 mg). HPLC Method 1, RT=8.52 min, HPLC purity (AUC): 99.3% at 280 nm); $^1$H NMR (CD$_3$OD) δ (ppm): 7.77 (s, 1H), 4.58 (q, J=8.0 Hz, 1H), 3.80 (s, 3H), 2.44 (s, 3H), 2.35 (s, 3H). MS-ESI (m/z) 251.2 [M+1]$^+$, 220.2 (100%).

(iv) 3-Hydroxy-1,2-dimethyl-5-[2,2,2-trifluoro-1-(4-methylpiperazin-1-yl)ethyl]pyridin-4(1H)-one hydrochloride (Apo7063) was prepared from 5-(1-chloro-2,2,2-trifluoroethyl)-3-hydroxy-1,2-dimethylpyridin-4(1H)-one hydrochloride (550 mg, 1.9 mmol) and 1-methylpiperazine (3.0 mL, 27.0 mmol) was added. The reaction was stopped when analysis of the HPLC chromatogram (Method 1) of the reaction mixture complete conversion. The reaction mixture was concentrated to give a solid. To the solid was added methanol (2 mL), the mixture was vortexed and filtered. Thus, Apo7063 was obtained as a solid (280 mg). Yield=41%; HPLC Method 1, purity (AUC)=99.8% at 280 nm; $^1$H NMR (DMSO-D$_6$+a few drops of D$_2$O) δ (ppm): 7.69 (s, 1H), 4.93 (q, J=9.7 Hz, 1H), 3.70 (s, 3H), 2.60-3.40 (b, 8H), 2.69 (s, 3H), 2.29 (s, 3H); MS-ESI m/z 320 [M+1]$^+$ (100%), 220.

Example 23

Preparation of 2-(dimethylamino)-3-hydroxy-1-methyl-6-(2,2,2-trifluoroethyl)pyridin-4(1H)-one (Apo7077)

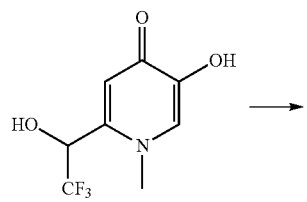

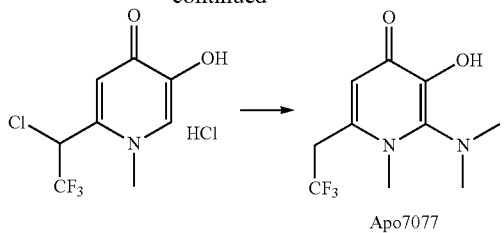

Thionyl chloride (1.6 mL, 21.9 mmol) was added dropwise to a suspension of 5-hydroxy-1-methyl-2-(2,2,2-trifluoro-1-hydroxyethyl)pyridin-4(1H)-one (0.82 g, 3.7 mmol) and acetonitrile (30 mL) under a blanket of nitrogen. The reaction was heated to reflux and a clear solution resulted. The progress of the reaction was monitored by TLC (eluant: methanol:dichloromethane, 1:10, v:v). The reaction mixture was concentrated repeatedly in acetonitrile to give a solid, which was used in the next step without further purification. $^1$H NMR (DMSO-D$_6$) δ (ppm): 8.35 (s, 1H), 7.62 (s, 1H), 6.77 (m, 1H), 4.12 (s, 3H).

A solution of the chloride product from the previous step in acetonitrile was added to a solution of dimethylamine (40 wt % in water, 9.0 mL, 71.1 mmol). The mixture was stirred vigorously. The progress of the reaction was monitored by TLC (eluant: methanol/dichloromethane, 1/10, v/v), and by HPLC (Method 1, RT of Apo7077=13.37 min, conversion was about 78%). The reaction mixture was concentrated to dryness. The residue was taken up in dichloromethane (30 mL), then washed with de-ionized water. The organic phase was dried over sodium sulfate, filtered, and concentrated to give a crude solid. Purification of the crude by column chromatography on silica gel (eluant: methanol/dichloromethane, 5/100, v/v) afforded Apo7077 (280 mg). Yield=30%; HPLC purity (AUC): 99.2% at 280 nm; $^1$H NMR (DMSO-D$_6$) δ (ppm): 6.23 (s, 1H), 3.93 (q, J=10.7 Hz, 2H), 3.63 (s, 3H), 2.74 (s, 6H); $^{19}$F NMR (DMSO-D$_6$) δ (ppm): −63.37 (t, J=50.8 Hz); MS-ESI m/z 251 [M+1]$^+$ (100%), 236, 221, 207, 166.

Example 24

Preparation of 2-((dimethylamino)methyl)-3-hydroxy-1-methyl-6-(2,2,2-trifluoro-1-hydroxyethyl)pyridin-4(1H)-one (Apo7081)

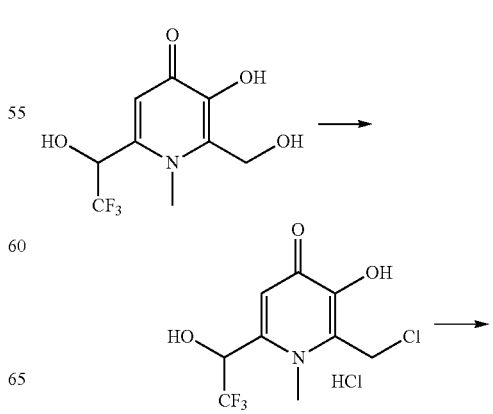

-continued

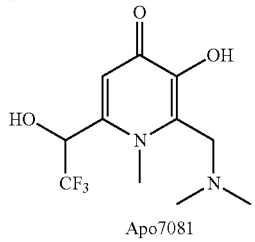

Apo7081

-continued

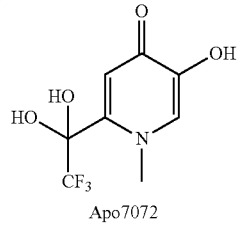

Apo7072

Thionyl chloride (0.48 mL, 6.6 mmol) was added dropwise to a suspension of 3-hydroxy-2-(hydroxymethyl)-1-methyl-6-(2,2,2-trifluoro-1-hydroxyethyl)pyridin-4(1H)-one (1.50 g, 5.9 mmol) in acetonitrile (45 mL). The progress of the reaction was monitored by TLC (eluant:methanol: dichloromethane, 15:100, v:v), and the starting material was consumed within 5 min. The reaction mixture was concentrated repeatedly in acetonitrile to give a solid, which was then washed with acetonitrile (15 mL×1). Thus, 2-(chloromethyl)-3-hydroxy-1-methyl-6-(2,2,2-trifluoro-1-hydroxyethyl)pyridin-4(1H)-one hydrochloride was obtained as a white solid (1.18 g).

The latter compound was dissolved in acetonitrile (20 mL) and added to a solution of dimethylamine (40 wt % in water, 15 mL, 118.5 mmol). The resulting yellowish solution was stirred vigorously, and the progress of the reaction was monitored by HPLC Method: Column: XTerra MS C18, 4.6×250 mm; A=Aqueous phase: 4 mM Tris, 2 mM EDTA, pH 7.4; B=Organic phase: $CH_3CN$; Flow rate=1.0 mL/min; Injection volume=5 μL; Wavelength (λ): 220, 254, 280, 450 nm. Gradient method; min-B % 0-5, 15-55, 25-55, 25.05-5, 30-5. (RT of Apo7081=9.45 min, HPLC purity (AUC): about 60% at λ=280 nm). The reaction mixture was concentrated to give a solid. To the solid was added de-ionized water (15 mL) and methanol (100 mL), the resulting mixture was stirred and filtered. The filtrate was collected and concentrated in vacuo. The residue was purified by column chromatography on silica gel (eluant: methanol/dichloromethane, 5/100, v/v). Thus, Apo7081 was obtained (24 mg). HPLC Method 1, RT=9.59 min, purity (AUC): 98.6% at 280 nm; $^1H$ NMR ($CD_3OD$) δ (ppm): 6.82 (s, 1H), 5.54 (q, J=6.2 Hz, 1H), 3.96 (s, 3H), 3.76 (s, 2H), 2.32 (s, 6H); MS-ESI m/z 281 $[M+1]^+$, 236 (100%), 208.

Example 25

Preparation of 5-hydroxy-1-methyl-2-(2,2,2-trifluoro-1,1-dihydroxyethyl)pyridin-4(1H)-one (Apo7072)

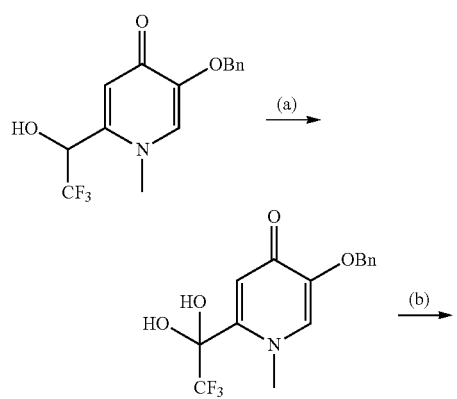

(a) To an ice-salt cooled suspension of 5-(benzyloxy)-1-methyl-2-(2,2,2-trifluoro-1-hydroxyethyl)pyridin-4(1H)-one (1.20 g, 3.8 mmol) and a 10% sodium bicarbonate solution (4 mL) in acetone (36 mL) were placed in a 250-mL 1-N RB equipped with a magnetic stir bar to give a suspension was added a solution of potassium bromate (99 mg, 0.6 mmol) dissolved in de-ionized water (3 mL). A solution of TEMPO (31 mg, 0.2 mmol) in acetone (1 mL) was added to the suspension, followed by a solution of sodium hypochlorite (0.96 M, 6.5 mL, 6.24 mmol). HPLC was used to monitor the progress of the reaction (HPLC Column: XTerra MS C18, 4.6×250 mm; A=Aqueous phase: 4 mM Tris, 2 mM EDTA, pH 7.4; B=Organic phase: $CH_3CN$; Flow rate=1.0 mL/min; Injection volume=5 μL; Wavelength (λ): 220, 254, 280, 450 nm. Isocratic method; aqueous:organic=75:25, RT of the SM=10.30 min, RT of the product=11.37 min, the conversion was >99%). The reaction mixture was filtered. The filtrate was collected and concentrated to give a semisolid. The semi-solid was suspended in dichloromethane (40 mL) and brine (30 mL). The mixture was stirred and the solid was collected by suction filtration. The solid was washed with de-ionized water (15 mL×4) and with ether (15 mL×4). Thus, 5-(benzyloxy)-1-methyl-2-(2,2,2-trifluoro-1,1-dihydroxyethyl)pyridin-4(1H)-one was obtained (0.93 g). Yield=73%; HPLC Method 2, purity (AUC)=99.4% at 280 nm; $^1H$ NMR (DMSO-$D_6$) δ (ppm): 8.45 (s, 2H), 7.67 (s, 1H), 7.4 (m, 5H), 6.66 (s, 1H), 5.04 (s, 2H), 3.85 (s, 3H); MS-ESI m/z 330 $[M+1]^+$, 91 (100%).

(b) Debenzylation of 5-(benzyloxy)-1-methyl-2-(2,2,2-trifluoro-1,1-dihydroxyethyl)pyridin-4(1H)-one (700 mg, 2.1 mmol) was carried out in a hydrochloric acid solution (4M, 22 mL) by heating to reflux. HPLC was used to monitor the progress of the reaction (HPLC Method 2, RT of the SM=11.47 min, RT of the product=3.26 min, conversion >98%). The resulting solution was concentrated to give oil. About half of the oily residue was weighed out, and dissolved in de-ionized water. The pH of the resulting solution was adjusted to 6 with a 6.00 N sodium hydroxide solution (160 μL). Solid appeared upon stirring. The solid was collected by filtration, thoroughly washed with de-ionized water and ether. Thus, a sample of 5-hydroxy-1-methyl-2-(2,2,2-trifluoro-1,1-dihydroxyethyl)pyridin-4 (1H)-one (Apo7072) was obtained (118 mg). Yield=46%; HPLC Method: Column: XTerra MS C18, 4.6×250 mm; A=Aqueous phase: 4 mM Tris, 2 mM EDTA, pH 7.4; B=Organic phase: $CH_3CN$; Flow rate=1.0 mL/min; Injection volume=5 μL; Wavelength (λ): 220, 254, 280, 450 nm. Isocratic method; aqueous:organic=75:25, purity (AUC)= 99.5% at 280 nm; $^1H$ NMR (DMSO-$D_6$+a few drops of $D_2O$) δ (ppm): 7.47 (s, 1H), 6.66 (s, 1H), 3.82 (s, 3H); MS-ESI m/z 240 $[M+1]^+$, 222 (100%), 125.

Example 26

A. pKa Determination by Potentiometric Titration

The pKa values of ligands were determined by potentiometric titration when a ligand concentration $>1×10^{-2}$ M in water could be prepared. In a typical experiment, the sample solution ($1.00 \times 10^{-2}$ M) was prepared by the following method: Apo7041 (125.4 mg) was weighed into a 50 mL volumetric flask, and about 40 mL of 0.1 M NaCl was added. The mixture was sonicated for 10 min to give a clear colorless solution. More of the 0.1 M NaCl was added to volume and the resulting solution was vortexed to mix. 40 mL of the solution was transferred into a T70 titration cell by using a 10 mL digital pipet. A 6.000 N sodium hydroxide solution (127 µL, 1.9 equiv) was added, and the pH (11.82) of the solution was recorded. The solution was allowed to equilibrate at 22° C. for 5 min.

The solution was then titrated against a 6.000 N hydrochloric acid solution at 22° C. by using a Mettler Toledo T70 autotitrator, until the pH reached 1.5. The volume of acid added and the pH reading were recorded. Thus, 501 measurements were taken for this experiment.

The data set of pH vs. acid volume was, analyzed using Hyperquad 2000 software (version 2.1, Peter Gans, University of Leeds). The pKa values were obtained using the model: $L^-+H^+ \leftrightarrows LH$ ($pKa_1$), $LH+H^+ \leftrightarrows LH_2^+$, and $LH_2^+ + H^+ \leftrightarrows LH_3^{2+}$ ($pKa_3$). Thus, Apo7041 has $pKa_1=9.39$, $pKa_2=3.52$, and $pKa_3=1.66$ as determined potentiometrically.

B. pKa Determination by Spectrophotometric Titration

The pKa values of ligands can be determined by spectrophotometric titration when both the conjugated acid and base absorb in the UV-visible region. In a typical experiment, the sample solution was prepared by the following method: Apo7041 stock solution (12.74 mg) was weighed into a 10 mL volumetric flask, and 0.1 M NaCl solution was added to volume. The mixture, was sonicated and voltexed to give a clear colorless solution. The concentration of Apo7041 of this stock solution is $5.1 \times 10^{-3}$ M.

Apo7041 sample solution: 727 µL of the above stock solution was transferred into a 50 mL volumetric flask by using a 1000 µL digital pipet, and 0.1 M NaCl was added to volume. The resulting solution was vortexed to mix to give a sample solution. The concentration of Apo7041 of this sample solution is $7.4 \times 10^{-5}$ M. 20 mL of the sample solution was transferred into a 35 mL beaker by using a 10 mL digital pipet. The sample solution was circulated between the beaker and the flow cell using a sipper system.

The sample solution was titrated against standard hydrochloric acid solutions at 22° C. to reach pH 1.11. After each addition of acid the solution was allowed to equilibrate until a constant pH reading was reached. The pH and the UV-Vis spectrum were recorded for each measurement. The solution was titrated until there was no obvious change in the spectra after several subsequent additions of acid. Thus, 30 measurements were recorded.

The resulting data set was then analyzed using pHAB (Peter Gans, University of Leeds). The pKa values were obtained using the model: $LH+H^+ \leftrightarrows LH_2^+$, and $LH_2^+ + H^+ \leftrightarrows LH_3^{2+}$ ($pKa_3$). Thus, Apo7041 has $pKa_2=3.51$, and $pKa_3=1.23$ as determined spectrophotometrically.

Example 27

Stoichiometry of Fe-Complexes by Job's Method

In a typical experiment Fe-Apo7053 complex solutions were prepared by mixing a stock solution of $Fe^{2+}$ (atomic absorption standard, 989 µg/mL in 1 wt HCl, Aldrich) and a stock solution of Apo7053 ($7.88 \times 10^{-3}$ M in 0.1 M MOPS, pH 7.4). Twelve sample solutions were prepared. While the sum of the total iron concentration ($[iron]_{total}$) and the total ligand concentration ($[L]_{total}$) in each of the 12 sample solutions were kept constant ($8.00 \times 10^{-4}$ M), the molar fraction of the ligand, $\alpha$ ($\alpha=[L]_{total}/([L]_{total}+[iron]_{total})$), for the 12 sample solutions were different, and were prepared as 0.0, 0.1, 0.2, 0.3, 0.4, 0.5, 0.6, 0.7, 0.75, 0.8, 0.9 and 1.0, respectively. The total volume for each of the 12 sample solutions was 5 mL, using MOPS (0.1 M, pH 7.4) as the solvent. The pH of the 12 solutions were adjusted to pH 7.4 with NaOH. The sample solutions were vortexed at rt for 2.5 h, and then stayed at rt overnight. The sample solutions were centrifuged at 4000 rpm for 15 min. The UV-Vis spectrum was recorded at 22° C. for each of the 12 solutions.

Figure 3A:
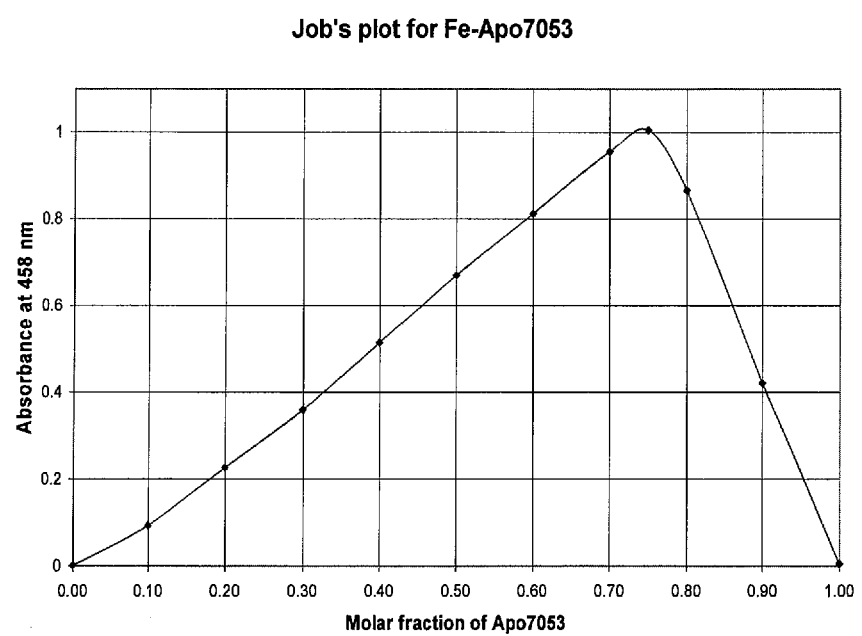
FIG. 3A is a diagrammatic representation of a Job's Plot of Apo 7053 5-[1-(dimethylamino)-2,2,2-trifluoroethyl]-3-hydroxy-1,2-dimethylpyridin-4(1H)-one, a compound of Formula I.

A Job's plot was created with the absorbance at 458 nm as the y-axis and $\alpha$ as the x-axis. A maximum absorbance was found at $\alpha=0.75$, which corresponds to an iron: ligand ratio of 1:3 in the complexes. The Job's plot result is shown in FIG. 3A.

Figure 3B:
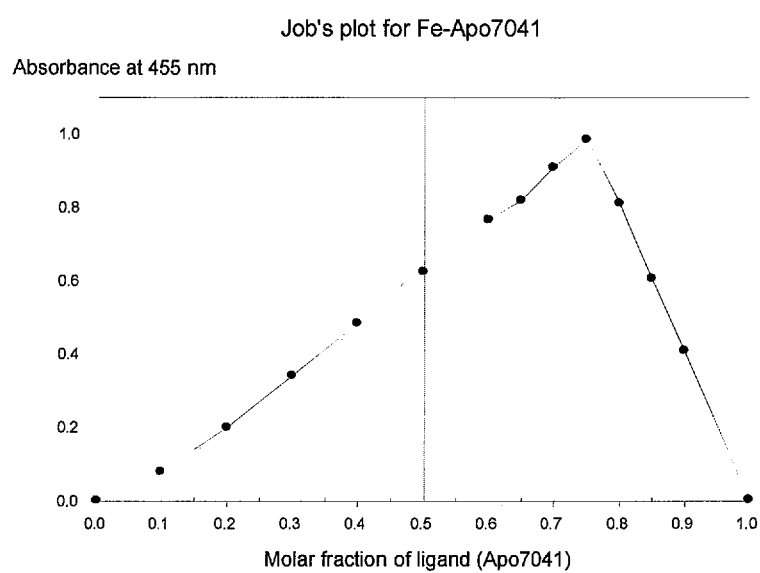
FIG. 3B is a diagrammatic representation of a Job's plot for Fe-Apo7041 system with [Fe]$_{total}$ [Apo7041]$_{total}$=8× 10$^{-4}$ M in 0.1 M MOPS at pH 7.4.

Proceeding in a similar manner, the Job's plot for Fe-Apo7041 was created, and is shown in FIG. 3B.

Example 28

Distribution Coefficient Determination, $D_{7.4}$ $K_2HPO_4$ buffer (50 mM, pH=7.4) and 1-octanol were used as the aqueous phase and the organic phase, respectively. The $K_2HPO_4$ buffer and 1-octanol were mixed, and pre-saturated with each other before use.

In a typical experiment, an aqueous solution of Apo6995 (3-hydroxy-2-methyl-1-(2,2,2-trifluoroethyl)pyridin-4(1H)-one) was prepared by weighing out 3 mg of the compound into a 10-mL test-tube. It was then mixed with $K_2HPO_4$ buffer (2 mL) and sonicated for 30 minutes with frequent vortexing. The solution was then filtered through HPLC syringe filter (4 mm PVDF syringe filter 0.45 µM) to obtain the aqueous solution. It was analyzed by HPLC (Column: Waters Symmetry $C_{18}$, 5 µM, 3.9×50 mm; Mobile phase: 0.035% $HClO_4$/ACN; Gradient method: time in minutes—ACN in %: 0-10, 10-90, 12-90, 14-10, 16-10; Flow rate: 1 mL/min; Injection volume=2 µL; detector wavelength: 270 nm) to obtain the peak height ($H_I$).

One mL of this aqueous solution was pipetted out into another 10-mL test-tube and mixed with 1 mL of 1-octanol. The mixture was then vortexed for 1 hour. The solution was centrifuged at 2000 rpm for 10 minutes. A small amount of the lower aqueous layer was carefully pipetted out and analyzed by HPLC to obtain the peak height ($H_F$). The distribution coefficient, $D_{7.4}$, was calculated using the following equation: $D_{7.4}=(H_I-H_F)/H_F$.

In a similar fashion, $D_{7.4}$ was determined for the following compounds:

| Apo# | $D_{7.4}$ | Log $D_{7.4}$ |
| --- | --- | --- |
| Deferiprone | 0.17 | −0.77 |
| 6995 | 2.51 | 0.40 |
| 7030 | 5.93 | 0.77 |
| 7040 | 8.76 | 0.94 |
| 7060 | 4.93 | 0.69 |
| 7065 | 4.93 | 0.69 |
| 7066 | 4.69 | 0.67 |
| 7067 | 2.82 | 0.45 |
| 7069 | 0.66 | −0.18 |
| 7070 | 1.72 | 0.23 |
| 7083 | 1.70 | 0.23 |

Example 29

Determination of Metal Complexation Constants

A. Instrumental and Chemicals:

For spectrophotometric titration, a pH meter (Accumet Research AR15, 13-636-AR15, Fisher) and a combination electrode (Accumet Standard-size Glass Combination Electrode, 13-620-285, Fisher) were used for pH measurements. Before using, the electrode was calibrated with three standard buffer solutions (pH 4.00, pH 7.00, and pH 10.00, Fisher). The titrant was added manually by using digital pipettes (Eppendorf). An UV-visible spectrophotometer (Agilent 8453) was used for UV-Vis absorbance measurements.

A sipper system (89068D Agilent) was used whenever pH-dependent absorbencies were measured. A vortexer (VX-2500 Multi-tube Vortexer, VWR Scientific Products) was used for the preparation of sample solutions in both distribution coefficient and Job's plot experiments.

For potentiometric titration, an autotitrator (Mettler Toledo T70) and a combination electrode (Mettler Toledo DG 115-SC) were used. Before using, the electrode was calibrated with three standard buffer solutions (pH 4.00, pH 7.00, and pH 10.00, Fisher). The titrant was added automatically by using T70. The data set of pH vs. titrant volume was recorded.

The metal stock solutions were purchased from Aldrich: Iron atomic absorption standard solution (1000 μg/ml of Fe in 1 wt. % HCl); Aluminum atomic absorption standard solution (1000 μg/ml of Al in 1 wt % HCl); Calcium atomic absorption standard solution (1000 μg/ml of Ca in 1 wt. % $HNO_3$); Copper atomic absorption standard solution (1000 μg/ml of Cu in 1 wt. % $HNO_3$); Magnesium atomic absorption standard solution (1000 μg/ml of Mg in 1 wt. % $HNO_3$); Manganese atomic absorption standard solution (1000 μg/ml of Mn in 1 wt. % $HNO_3$); Zinc atomic absorption standard solution (1000 μg/ml of Zn in 1 wt. % HCl). The standard Sodium Hydroxide and Hydrochloric acid solutions were purchased from VWR Scientific Products. MOPS (3-[N-Morpholino]propanesulfonic acid) was purchased from Sigma-Aldrich.

B. Determination of Stepwise Formation Constants for Fe-Apo7041 System by Spectrophotometric Titration in 0.1M NaCl Solution Stepwise formation constants for $M^{n+}$-ligand systems were determined by spectrophotometric titration when metal complexes have a strong absorbance in the visible region due to ligand to metal charge transfer.

In a typical experiment, the sample solution was prepared according to the following procedure: compound Apo7041 (12.96 mg) was weighed into a 50 mL volumetric flask, and about 40 mL of 0.1 M NaCl was added. The mixture was sonicated for 10 min to give a clear colorless solution. The iron stock solution (atomic absorption standard, Aldrich, 565 μL, 10.00 μmol) was pipetted into the solution, followed by the addition of 1.000 N NaOH (170 μL). More of the 0.1 M NaCl was added to volume and the resulting solution was vortexed to mix. The molar ratio between the total iron and the total Apo7041 was 1/5.1. The mixture was vortexed at rt for 1 h. 20 mL of the sample solution was transferred into a 35 mL beaker by using a 10 mL digital pipet. The sample solution was circulated between the beaker and the flow cell using a sipper system. The sample solution was titrated against hydrochloric acid solutions at 22° C. until the pH reached 0.021. After each addition of acid, the solution was allowed to equilibrate until a constant pH reading was reached. The pH and the UV-Vis spectrum were recorded for each measurement. For each measurement enough acid was added so that there was a slight decrease in the absorbance of the spectrum. Altogether, 68 measurements were taken to finish the experiment.

The resulting data set was then analyzed using pHAB. The formation constants for Fe-Apo7041 system were optimized using the model shown in the first column of the table. The results are shown in the Table 29B below.

TABLE 29B

| The model | symbol | value |
|---|---|---|
| $Fe^{3+} + LH \leftrightarrows (FeLH)^{3+}$ | Log $\beta_{111}$ | 18.1 |
| $(FeLH)^{3+} + LH \leftrightarrows (FeL_2H_2)^{3+}$ | Log $\beta_{122}$ | 35.0 |
| $(FeL_2H_2)^{2+} + H^+ \leftrightarrows (FeL_3H_3)^{3+}$ | Log $\beta_{133}$ | 50.5 |
| $(FeL_3H)^+ + H^+ \leftrightarrows (FeL_3H_2)^{2+}$ | Log $\beta_{132}$ | 48.3 |
| $(FeL_3)^0 + H^+ \leftrightarrows (FeL_3H)^+$ | Log $\beta_{131}$ | 44.5 |
| $Fe^{3+} + 3L^- \leftrightarrows (FeL_3)^0$ | Log $\beta_{130}$ | 38.8 |
| $L^- + H^+ \leftrightarrows LH$ | $pKa_1$ | 9.39 |
| $LH + H^+ \leftrightarrows LH_2^+$ | $pKa_1 + pKa_2$ | 12.91 |
| $LH_2^+ + H^+ \leftrightarrows LH_3^{2+}$ | $pKa_1 + pKa_2 + pKa_3$ | 14.57 |

C. Determination of Stepwise Formation Constants for Cu-Apo7041 System by Potentiometric Titration in 0.1M Aqueous NaCl/MeOH, 1/1, v/v Mixture Stepwise formation constants for $Cu^{2+}$-ligand system were determined by potentiometric titration when metal complexes (≥0.002 M) do not precipitate during titration. In a typical experiment, the sample solution was prepared by the following method: Apo7041 (126.1 mg, 0.50 mmol) was weighed into a 50 mL volumetric flask, and about 35 mL of a mixed solvent (0.1 M NaCl aqueous: MeOH, 1:1, v:v) was added. The mixture was sonicated for 10 min to give a clear colorless solution. The copper stock solution (atomic absorption standard, Aldrich, 6.33 mL, 0.10 mmol) was pipetted into the solution. More of the mixed solvent was added to volume and the resulting solution was vortexed to mix. The molar ratio between the total copper and the total Apo7041 was 1/5. 40 mL of the solution was transferred into a T70 titration cell by using a 10 mL digital pipet. A 6.000 N sodium hydroxide solution (300 μL) was added, and the pH (12.17) of the solution was recorded. The solution was allowed to equilibrate at 22° C. for 5 min.

The solution was then titrated against a 6.000 N hydrochloric acid solution at 22° C. by using a Mettler Toledo T70 autotitrator, until the pH reached 1.5. The volume of acid added and the pH reading were recorded. Thus, 533 measurements were taken for this experiment.

The pKa values of Apo7041 in the same mixed solvent were also determined by potentiometric titration using the procedure described in Example 1.

The data set of pH vs. acid volume for Cu-Apo7041 system was analyzed using Hyperquad 2000 software (version 2.1, Peter Gans, University of Leeds). The formation constants for Cu-Apo7041 system were optimized using the model shown in the first column of Table 29C. The results are shown in the second and third column.

TABLE 29C

| The model | symbol | value |
|---|---|---|
| $(CuL_2H)^+ + H^+ \leftrightarrows (CuL_2H_2)^{2+}$ | Log $\beta_{122}$ | 27.9 |
| $(CuL_2)^0 + H^+ \leftrightarrows (CuL_2H)^+$ | Log $\beta_{121}$ | 23.0 |
| $Cu^{2+} + 2L^- \leftrightarrows (CuL_2)^0$ | Log $\beta_{120}$ | 17.3 |
| $L^- + H^+ \leftrightarrows LH$ | $pKa_1$ | 10.1 |
| $LH + H^+ \leftrightarrows LH_2^+$ | $pKa_1 + pKa_2$ | 13.3 |
| $LH_2^+ + H^+ \leftrightarrows LH_3^{2+}$ | $pKa_1 + pKa_2 + pKa_3$ | 15.3 |

D. Determination of Stepwise Formation Constants for Zn-Apo7041 System by Potentiometric Titration in 0.1M Aqueous NaCl/MeOH, 1/1, v/v Mixture Stepwise formation constants for $Zn^{2+}$-ligand system were determined by potentiometric titration when metal complexes (≥0.002 M) do not precipitate during titration. In a typical experiment, the sample solution was prepared by the following method: Apo7041 (126.3 mg, 0.50 mmol) was weighed into a 50 mL volumetric flask, and about 35 mL of a mixed solvent (0.1 M NaCl aqueous: MeOH, 1:1, v:v) was added. The mixture was sonicated for 10 min to give a clear colorless solution. The zinc stock solution (atomic absorption standard, Aldrich, 6.64 mL, 0.10 mmol) was pipetted into the solution followed by addition of sodium hydroxide solution (6.000 N, 300 μL). More of the mixed solvent was added to volume and the resulting solution was vortexed to mix. The molar ratio between the total zinc and the total Apo7041 was 1/5. 40 mL of the solution was transferred into a T70 titration cell by using a 10 mL digital pipet. A 6.000 N sodium hydroxide solution (160 μL) was added, and the pH (11.95) of the solution was recorded. The solution was allowed to equilibrate at 22° C. for 5 min.

The solution was then titrated against a 6.000 N hydrochloric acid solution at 22° C. by using a Mettler Toledo T70 autotitrator, until the pH reached 1.5. The volume of acid added and the pH reading were recorded. Thus, 523 measurements were taken for this experiment.

The data set of pH vs. acid volume for Zn-Apo7041 system was analyzed using Hyperquad 2000 software (version 2.1, Peter Gans, University of Leeds). The formation constants for Zn-Apo7041 system were optimized using the model shown in the first column of the table 29D. The results are shown in the second and third column.

TABLE 29D

| The model | symbol | value |
| --- | --- | --- |
| $Zn^{2+} + LH \leftrightarrows (ZnLH)^{2+}$ | Log $\beta_{111}$ | 13.1 |
| $(ZnL_2)^0 + H^+ \leftrightarrows (ZnL_2H)^+$ | Log $\beta_{121}$ | 19.6 |
| $Zn^{2+} + 2L^- \leftrightarrows (ZnL_2)^0$ | Log $\beta_{120}$ | 13.2 |
| $L^- + H^+ \leftrightarrows LH$ | $pKa_1$ | 10.1 |
| $LH + H^+ \leftrightarrows LH_2^+$ | $pKa_1 + pKa_2$ | 13.3 |
| $LH_2^+ + H^+ \leftrightarrows LH_3^{2+}$ | $pKa_1 + pKa_2 + pKa_3$ | 15.3 |

Calculation of $pM^{n+}$ $pM^{n+}$ is defined as $-\log [M(H_2O)_m]^{n+}$ at physiological conditions, i.e.: pH 7.4, a ligand concentration of 10 μM, and a metal concentration of 1 μM. To calculate $pM^{n+}$ for a $ML_n$ system, $\beta_n$ and pKa values are needed ($\beta_n$ are the formation constants for $M^{n+} + nL^- \leftrightarrows ML_n$; pKa are the equilibrium constants for $L^- + n H^+ \leftrightarrows LH_n^{(n-1)+}$). The $pM^{n+}$ is calculated using the Hyss software (HYSS© 2000 Protonic Software).

The data obtained from the above determinations for Apo7041, a compound of formula I, can be found in Table 1.

Example 30

Cyclic Voltammetry

A criterion in the design of compounds of formula I concerns controlling the redox potential of the Fe-chelate system at pH 7.4 to a negative value below −320 my (vs NHE) to prevent any reactions with oxygen species. Iron exists in multiple states including $Fe^{2+}$ and $Fe^{3+}$. The iron (II)/iron (III) pair can act as a pair of one electron reducing agent and oxidizing agent. According to Crumbliss (http://www.medicine.uiowa.edu/FRRBNirtualSchool/Crumbliss-Fe.pdf) and Pierre (BioMetals, 12, 195-199, 1999), selective chelation of iron with redox potential control is a means to prevent iron from participating in a catalytic cycle to produce toxic hydroxyl radicals and/or reactive oxygen species (ROS) (e.g. via the Fenton reaction or Haber Weiss cycle). The Fe (III)-tris-chelate system with redox potential below −320 my (vs NHE or −540 my vs Ag/AgCl) at pH 7.4 will not be reduced by any biological reducing agents such as NADPH/NADH, therefore it will not participate in the Haber Weiss cycle to generate ROS (reactive oxygen species). Within the mammalian body, iron is bound to different proteins such as transferrin in human blood to ensure it remains in a form that cannot react with any oxygen molecules. The $E_{1/2}$ value of Fe-transferrin is −500 my (vs. NHE or −720 my vs. Ag/AgCl).

The redox potential of iron complexes can be measured by cyclic voltammetry (CV). The use of CV to measure the redox potentials of iron chelates deferiprone, desferrioxamine and Apo7041 (a representative compound of this invention) as chelators respectively, is illustrated in FIG. 1. Iron chelates such as Fe-desferrioxamine (DFO) and Fe-(deferiprone)$_3$ have redox potential $E_{1/2}$ values at −480 my (vs. NHE) and −628 my (vs. NHE), respectively, at pH 7.4. Compounds of formula I such Fe(Apo7041)$_3$ has a $E_{1/2}$ value of −530 my (vs. NHE) slightly more negative when compared to that of desferrioxamine. The cyclic voltammogram of Fe-DFO, Fe(deferiprone)$_3$ and Fe(Apo7041)$_3$ can be found in FIG. 1. One advantage of the chelators of this invention is that the redox potentials of their iron chelates lie in the extreme negative range at physiological pH 7.4, therefore their iron chelates will not participate in the redox cycle to generate reactive oxygen species at physiological pH. When combined with other novel properties as described in this invention, the compounds of formula I are effective agents in the removal of iron via a chelation mechanism.

Determination of $E_{1/2}$ of Fe(Apo7041)$_3$

A. Materials and Instruments

Potassium ferricyanide (III) was purchased from Aldrich. Deferoxamine mesylate (DFO) was purchased from Sigma. Iron atomic absorption standard solution (contains 1000 μg/mL of Fe in 1 wt. % HCl) was purchased from Aldrich. Electrochemical measurements were performed with a cyclic voltammetric analyzer (BAS, CV-50W Potentiostat). Software BAS CV-50W Version 2.31 was used. The following electrodes were used for determining redox potentials of the iron complexes: Ag/AgCl reference electrode (BAS, MF-2052); platinum auxiliary electrode (BAS, MW-1032); and glassy carbon working electrode (BAS, MF-2012). A pH meter (Accumet Research AR15, 13-636-AR15, Fisher Scientific) and pH electrode (AccupHast combination electrode, 13-620-297, Fisher Scientific) were used for pH adjustment of the sample solutions.

B. Preparation of Sample Solutions 2.0 mM solution of Fe(DFO) in 0.1 M NaCl (pH 7.4) 148.1 mg of deferoxamine mesylate (purity=95%) was accurately weighed out into a 100-mL volumetric flask. The solid was dissolved in about 30 mL of 0.1 M NaCl to give a clear colorless solution. To the solution was added 11.114 mL of the standard iron solution. The solution was diluted with 0.1 M NaCl to the 100 ml mark in the volumetric flask. The resulting solution was vortexed to ensure complete mixing. The solution was transferred to a 200-mL beaker. The pH of the solution was then adjusted to about 7.1 by adding standard solutions of sodium hydroxide. The beaker was then covered with parafilm and the solution was left stirring for overnight. The pH of the solution was adjusted to 7.40 in the following test day. The calculated molar ratio between iron$_{total}$ and DFO$_{total}$ was 1:1.07.

1.0 mM solution of Fe(Apo7041)$_3$ in 0.1 M NaCl (pH 7.4) Apo7041 (19.8 mg, 0.079 mmol) was accurately weighed out into a 25-mL round bottom flask. The solid was dissolved in about 14 mL of 0.1 M NaCl to give a clear colorless solution. To the solution was added a standard iron solution (847 µL, 0.015 mmol) followed by addition of sodium hydroxide solution (6.000 N, 44 µL). The resulting solution was vortexed to ensure complete mixing. The pH of the solution was recorded (7.5). The calculated molar ratio between iron$_{total}$ and Apo7041$_{total}$ was 1/5.3. In a similar manner, a solution of 2.0 mM of Fe(deferiprone)$_3$ in 0.1 M NaCl (pH 7.4) was prepared.

C. Determination of Redox Potentials of Iron Complexes

All potentials in the text are given versus the Ag/AgCl reference electrode. The redox potentials of 2.0 mM of K$_3$Fe(CN)$_6$ in 1.0 M potassium nitrate were measured at the beginning of each working day to verify the proper functioning of the cyclic voltammeter. The redox peak potentials of solutions of iron complexes at pH 7.4, that is, Fe(DFO), Fe(deferiprone)$_3$, and Fe(Apo7041)$_3$, were determined. For example, the Fe(Apo7041)$_3$ sample solution was purged with argon for approximately 15 min. A solvent trap containing 0.1 M NaCl was used to reduce evaporation. Cyclic voltammograms of the sample solution were recorded using glassy carbon electrode (working electrode), Ag/AgCl electrode (reference electrode), and platinum electrode (auxiliary electrode). The following instrument parameters were used: Init E (mV)=0; High E (mV)=0; Low E (mV)=−1200; Init P/N=N; V (mV/s)=200; No. of Sweep Segments=3; Sensitivity (PAN)=100; Stir Speed=50 rpm.

FIG. 1 shows the cyclic voltammograms of iron(III)L$_n$ complexes at pH 7.4: a) Fe(Apo7053)$_3$; b) Fe(Apo7041)$_3$; c) Fe(Apo7069)$_3$. The reduction peak potential ($E_p^{red}$), the oxidation peak potential ($E_p^{ox}$), the absolute difference ($\Delta E_p$) between $E_p^{red}$ and $E_p^{ox}$, and redox potential ($E_{1/2}$) of the four iron complexes were measured. $E_{1/2}$ value is calculated as ($E_p^{red}+E_p^{ox}$)/2.

The cyclic voltammograms of a) Fe(Apo7053)$_3$; b) Fe(Apo7041)$_3$; c) Fe(Apo7069)$_3$ represent a reversible single electron transfer process for each complex: Fe(III)L$_n$/Fe(II)L$_n$. The $E_{1/2}$ value of the reference Fe(DFO) determined in this lab is −698 mV versus the Ag/AgCl reference electrode, which is in excellent agreement to literature value (−688 mV) (A. L. Crumbliss et al., Inorganic Chemistry, 2003, 42, 42-50). The $E_{1/2}$ value of Fe(Apo7041)$_3$ is −731 mV, which is slightly more electronegative than that of Fe(DFO).

The Electrochemical properties of iron(III)L$_n$ complexes in 0.1M aqueous NaCl at pH 7.4 are listed below. Fe(DFO), {DFO=deferioxamine B}; Fe(L1)$_3$, {L1=deferiprone}; K$_3$Fe(CN)$_6$ are used as controls for the validation of the study.

| complex | $E_{red}$ (mV) | $E_{ox}$ (mV) | $\Delta E$ (mV) | $E_{1/2}$ (mV) vs. Ag/AgCl | $E_{1/2}$ (mV) vs. NHE |
|---|---|---|---|---|---|
| K$_3$Fe(CN)$_6$ | 197 | 282 | 85 | +20 | +240 |
| FeDFO | −754 | −642 | 112 | −698 | −478 |
| Fe(L1)$_3$ | −841 | −752 | 89 | −797 | −577 |
| Fe(7041)$_3$ | −789 | −672 | 117 | −731 | −511 |
| Fe(7053)$_3$ | −856 | −761 | 95 | −809 | −589 |
| Fe(7069)$_3$ | −793 | −706 | 87 | −750 | −530 |

Example 31

Benzoic Acid Hydroxylation Assay

Benzoic acid is a hydroxyl radical scavenger and reacts with hydroxyl radical to give 2-hydroxy, 3-hydroxy and 4-hydroxybenzoic acids. The benzoic acid hydroxylation assay is a chemical assay designed to detect damage caused by hydroxyl radical (Dean and Nicholson, Free Radical Research 1994, vol 20, 83-101). For example, deferiprone suppresses the formation of hydroxybenzoic acids in the presence of iron salts and hydrogen peroxide, while EDTA and iron salts allow such hydroxylation reactions to take place.

This screening assay involves the use of iron salt, benzoic acid, hydrogen peroxide and the chelator and measures the ability of the chelator to inhibit the formation of hydroxybenzoate as an indicator to prevent hydroxyl radical formation in living system.

Figure 9:
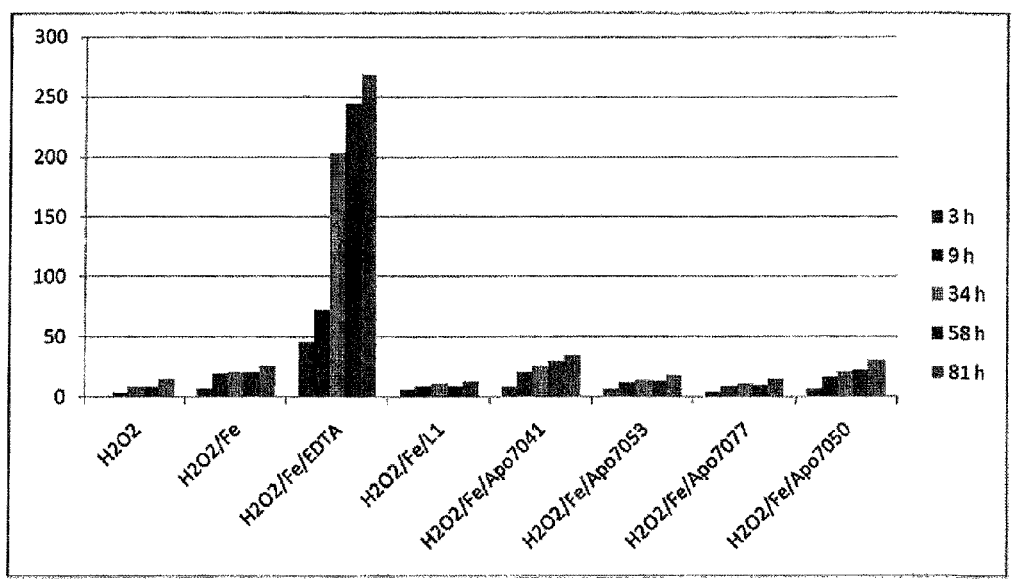
FIG. 9. A diagrammatic representation showing that a compound of formula I and deferiprone suppresses the formation of the hydroxybenzoic acid when benzoic acid is treated with hydrogen peroxide and iron salts. The y axis refers to the total concentration of 2-hydroxybenzoic acid, 3-hydroxybenzoic acid, and 4-hydroxybenzoic acid formed (unit: μM).
Figure 10:
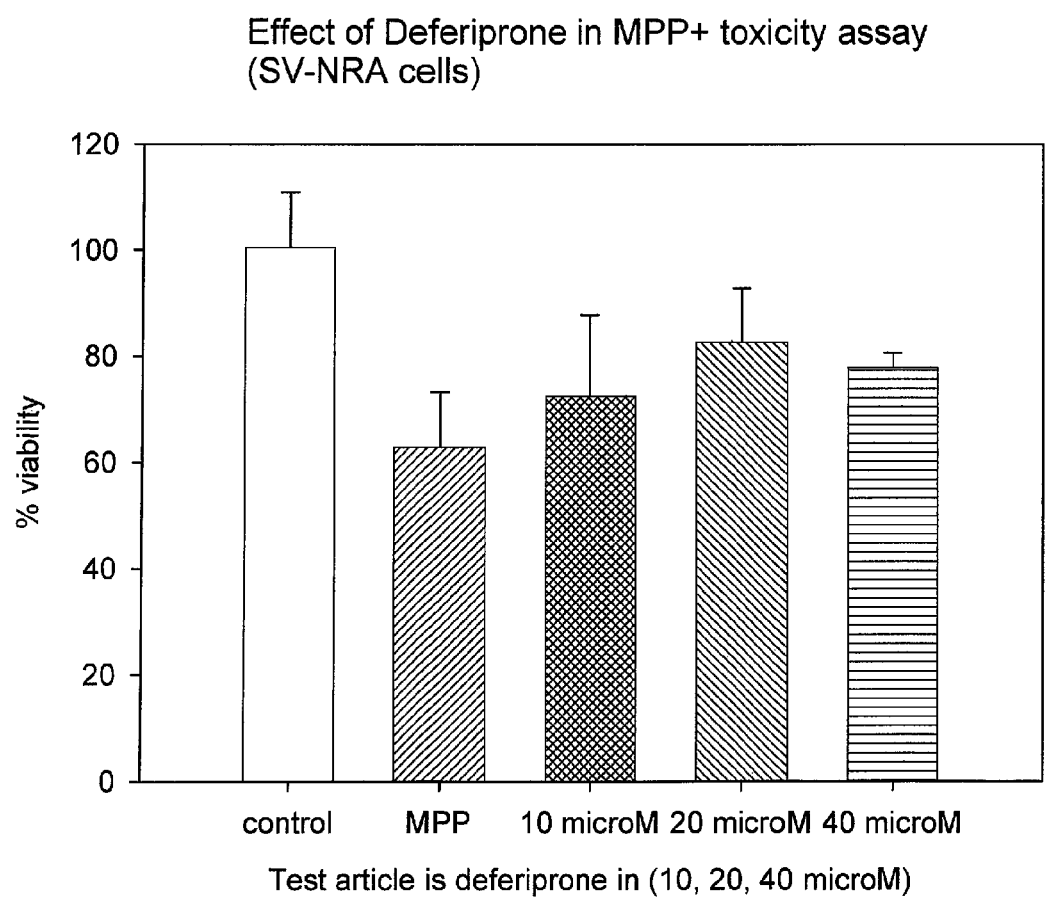
FIG. 10 is a diagrammatic representation of the neuroprotective action of deferiprone on MPP+ treated SV-NRA cells. MPP$^+$ treatment decreased cell viability when compared to untreated vehicle control. Treatment with deferiprone, an iron chelator drug resulted in about 20% increase in cell viability (p<0.05).
Figure 11:
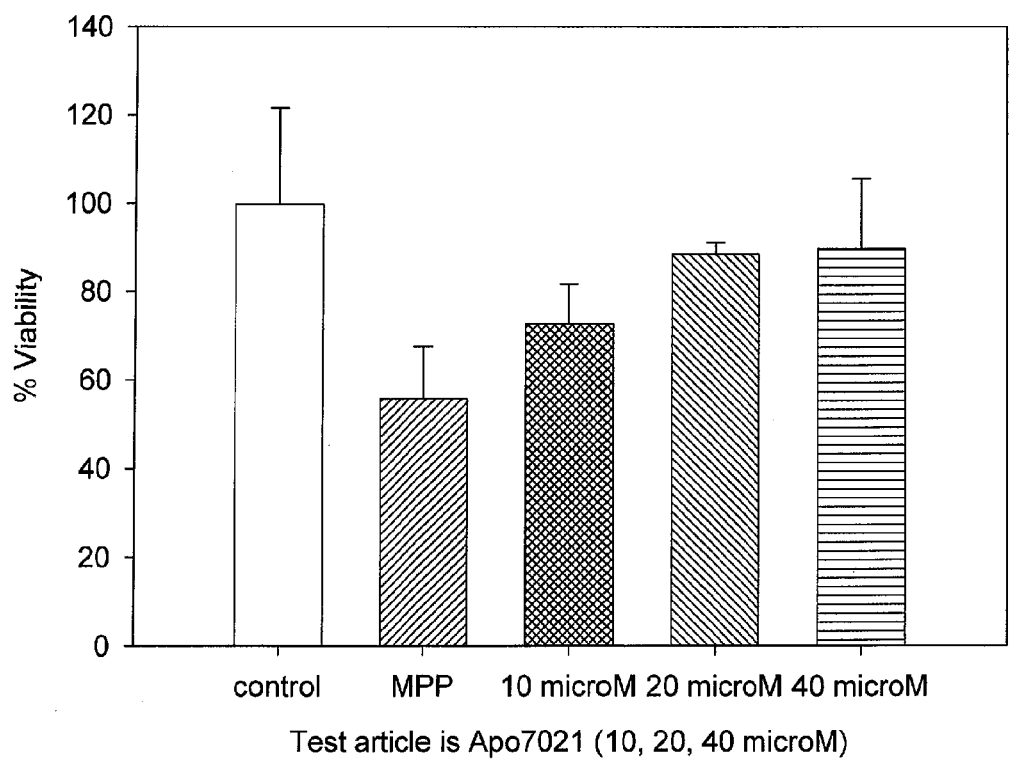
FIG. 11 is a diagrammatic representation showing the neuroprotective action of Apo7021, a compound of formula I, on MPP+ treated SV-NRA cells.
Figure 12:
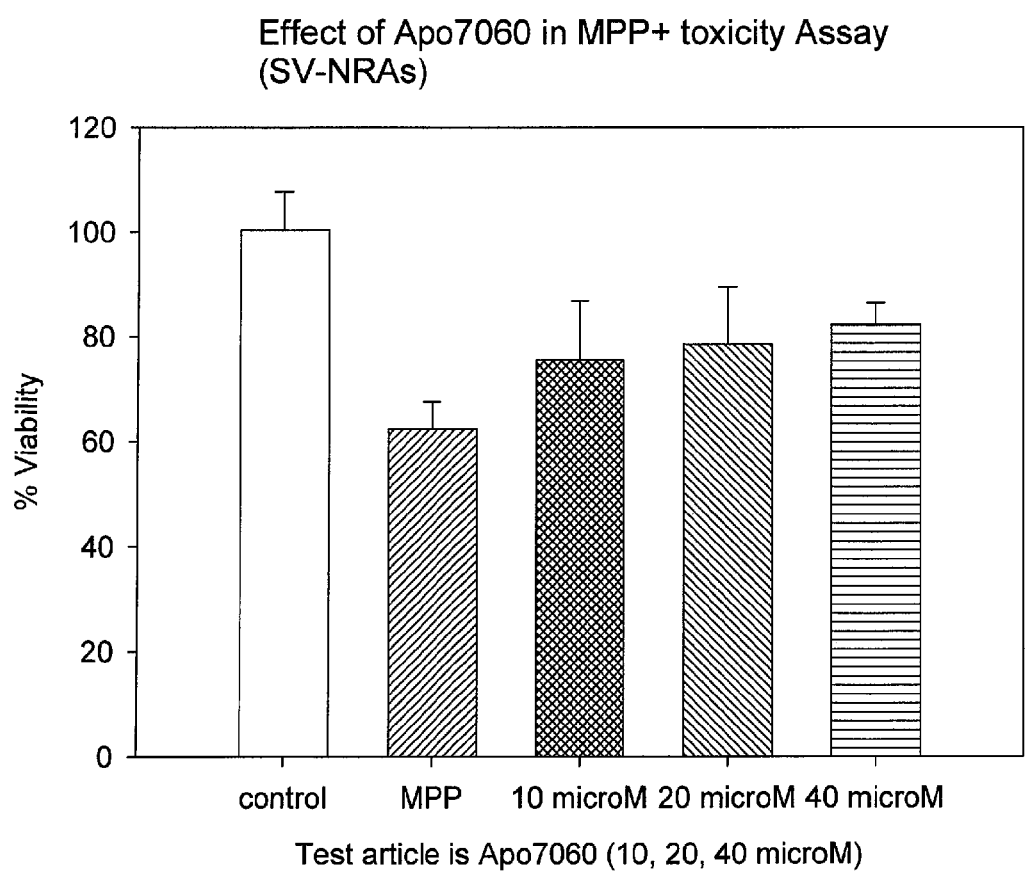
FIG. 12 is a diagrammatic representation showing the neuroprotective action of Apo7060, a compound of formula I, on MPP+ treated SV-NRA cells.
Figure 13:
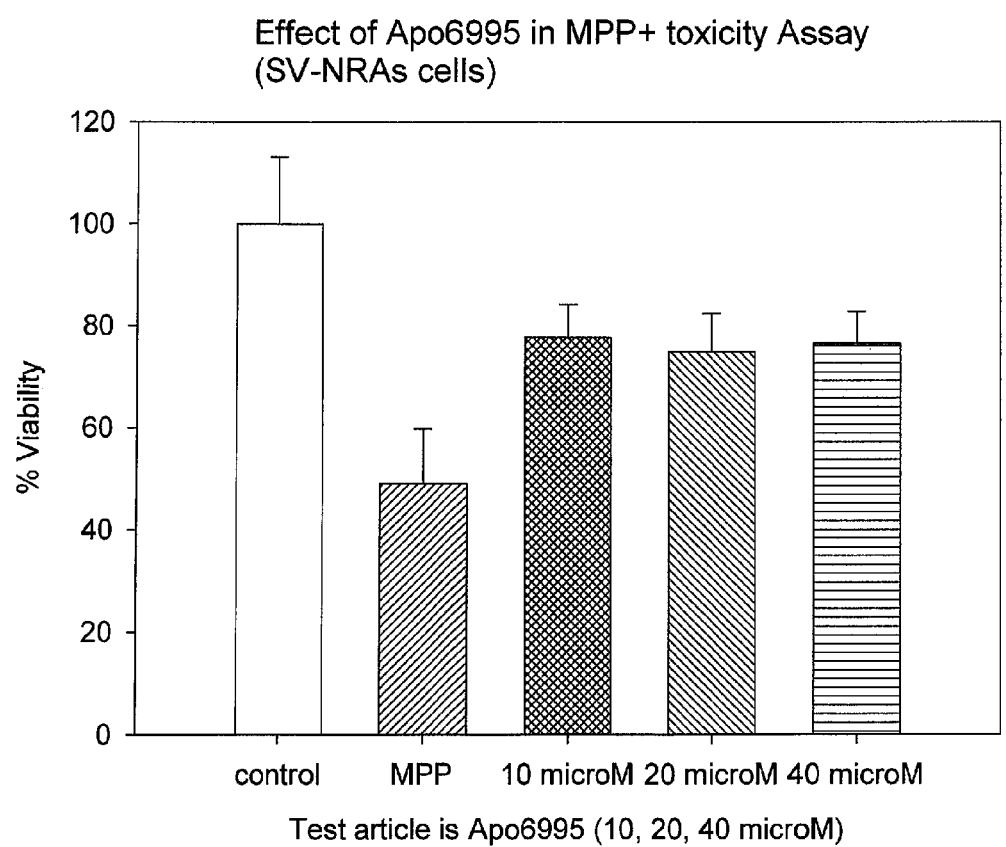
FIG. 13 is a diagrammatic representation showing the neuroprotective action of Apo6995, a compound of formula I, on MPP+ treated SV-NRA cells.

Compound of formula I has similar properties to deferiprone and suppresses the formation of the hydroxybenzoic acid when benzoic acid is treated with hydrogen peroxide and iron salts. The results are shown in FIG. 9. Compounds of formula I show inhibitory effect to the hydroxyl radical transformation of benzoic acid. Thus, these compounds are protective towards hydroxyl radical oxidation in biological systems.

Briefly, this procedure is based on the ability of hydroxyl radicals to hydroxylate benzoate to give 2-, 3- and 4-hydroxylated benzoic acid products. Benzoic acid (1 mM) is incubated over time up to 81 h at room temperature in the dark in 10 mM phosphate buffer (pH 7.4) with 6 mM hydrogen peroxide, ferric chloride (30 µM) and the Fe chelator (30 µM). HPLC is the method of choice used to monitor and quantify the amount of 2-, 3- and 4-hydroxylated products formed over time in the reaction mixture, and can be verified against authentic benzoic acid and its hydroxylated products via their respective retention times and areas under curve. In addition, several controls are used: (i) a control without added Fe stock solution and Fe chelator; (ii) a control without added Fe chelator; (iii) EDTA as positive control; and (iv) deferiprone as negative control. The Fe-EDTA system is a hydroxyl radical generator and is known to promote hydroxylation of benzoic acid. Under the experimental conditions, the Fe chelate from the compounds of formula I (Apo7041, Apo7050, Apo7053 and Apo7077) do not promote the hydroxylation of benzoic acid.

Example 32

A. Neuroprotective Effect of Compounds of Formula I on Hydrogen Peroxide Induced Apoptosis in SH-SY5Y Neuroblastoma Cells Hydrogen peroxide ($H_2O_2$) is a major ROS (reactive oxidative stress) and can induce apoptosis in many different cell types. One of the CNS drug design strategies is to use compounds with antioxidant properties as a possible treatment of both acute and chronic neurodegenerative diseases (Kang et al. Bioorganic & Medicinal Chemistry Letters, 2004, 14, 2261-2264). This involves testing the compounds of this invention for its protective effect against oxidative stress-induced cell death in SH-SY5Y human neuroblastoma cells. SH-SY5Y human neuroblastoma cells were cultured in DMEM (ATCC)/F12 (Cellgro) with 10% FBS. The cells were plated at 30,000 cells/cm$^2$ and grown for 1 day in the regular culture media prior to compound addition. Cells were routinely treated with the test compound, at a predetermined range, of concentrations, in the presence or absence of 50 μM hydrogen peroxide in a basal medium containing no FBS for 16-22 h. Cell viability was then measured using the routine MTT method (Mosmann, T., Rapid Colorimetric Assay for Cellular Growth and Survival: Application to Proliferation and Cytotoxicity Assays". J. Immunol. Meth. 1983, 65, 55-63).

For data analysis, cell viability relative to control not treated with either $H_2O_2$ or the test compound, was plotted against the compound concentration. The threshold protective concentration (TH) was defined as the highest concentration at which the compound did not display a significant protective effect (i.e. next higher concentration had a statistically significant protective effect) against hydrogen peroxide insult. Maximum effective concentration ($EC_{100}$) was a concentration at which the compound exhibited maximum protective effect. Cytotoxicity of the test compound was assessed in the absence of hydrogen peroxide. Cytotoxic concentration (CC1) was defined as the lowest compound concentration resulting in viability significantly below 80%. Cytotoxic concentration (CC2) was the lowest compound concentration resulting in viability significantly below 80% in $H_2O_2$-treated cells.

B. Evaluation of the Compounds in the Protection Against Endogenously Produced Aβ Toxicity Amyloid plaques, are formed by the aggregation of small peptides, called amyloid β peptide (Aβ), that are produced when amyloid precursor protein (APP) is cleaved by the action of two enzymes, β-APP cleaving enzyme and γ-secretase. One approach to the treatment of Alzheimer is, therefore, limiting the production of Aβ from its precursor by inhibiting one or both of these enzymes, while another approach is to inhibit the aggregation of Aβ via the use of metal chelators.

In this assay, human neuroblastoma cells (MC-65 cells) are genetically engineered to conditionally express amyloid β peptide (Aβ). The Aβ production is suppressed by tetracycline (TET+) presence in culture medium, and its production is activated when TET is withdrawn (TET-). The activation of Aβ production results in cell death "MC-65 suicide".

Protective effect of compounds against endogenously produced amyloid beta (Aβ) was assessed in human neuroblastoma MC-65 cells. MC-65 cells have been stably transformed to conditionally express high levels of a partial amyloid precursor (AP) fusion protein (Bryce Sopher et al., Brain Res Mol Brain Res. 1994, 207-17.). This protein is further proteolytically processed in the cells to form a set of AP-derived Aβ peptides. AP conditional expression in these cells is under control of tetracycline-responsive promoter system and results in pronounced cytotoxicity. Activity of the promoter is tightly regulated by the presence of the antibiotic tetracycline (TET) in the culture medium. In the presence of TET, the promoter is in the basal state and no amyloid beta peptide is synthesized. In the absence of TET the promoter is in induced state, resulting in the accumulation of Aβ peptides in the cells, degenerative changes in cell morphology and decreased survival.

Transfected human neuroblastoma cells (MC-65) were cultured in DMEM (ATCC) supplemented with non-essential amino acids and 10% FBS (VWR) in the presence of TET (1 μg/mL). For the experiment, the cells were plated at 35,000 cells/cm$^2$ and grown for 1 day in the regular culture media prior to compound addition. On the day of assay, culture supernatant was removed from the wells and cells were thoroughly washed once with the compound incubation matrix containing no FBS and no TET. MC-65 cells were treated with a test compound at pre-determined range of concentrations in a basal medium containing no FBS and in the absence or presence of 1 μg/mL TET for approximately 48 h. Cell viability was then measured using the MTT method.

For data analysis, cell viabilities relative to the control not treated with a test compound and maintained in the presence of TET were plotted against the compound concentration. The threshold protective concentration (TH) was defined as the highest concentration at which the tested compound did not display a significant protective effect (i.e. next higher concentration had a statistically significant protective effect) in the group maintained in the absence of TET. Maximum effective concentration ($EC_{100}$) was a concentration at which the compound exhibited maximum protective effect. Cytotoxicity of the test compound was assessed in the cells maintained in the presence of TET. Cytotoxic concentration (CC1) was defined as the lowest compound concentration resulting in viability significantly below 80%. CC2 is the lowest compound concentration resulting in viability significantly below 80% in cells expressing AP (i.e. cultured without tetracycline).

Chemical Structures of Compounds

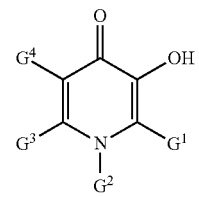

| Apo# | $G^1$ | $G^2$ | $G^3$ | $G^4$ |
|---|---|---|---|---|
| 6994 | H | $CH_2CF_3$ | Me | H |
| 6995 | Me | $CH_2CF_3$ | H | H |
| 6998 | $CH(CF_3)$-D-ala-NHMe | Me | H | H |
| 7021 | $CH_2CF_3$ | Me | $CH_2NMe_2$ | H |
| 7022 | $CH(OH)CF_3$ | Me | $CH_2NMe_2$ | H |
| 7030 | Et | $CH_2CF_3$ | H | H |
| 7032 | $CH(OH)CF_3$ | Me | $CH_2$-L-ala-OH | H |
| 7033 | $CH(OH)CF_3$ | Me | $CH_2$-L-ala-NHMe | H |
| 7035 | $CH(OH)CF_3$ | H | $CH_2NMe_2$ | H |
| 7038 | $CH(OH)CF_3$ | Me | Me | Cl |
| 7040 | $CH_2CF_3$ | Me | Me | Cl |
| 7041 | $CH(NMe_2)CF_3$ | Me | H | H |

-continued

| Apo# | $G^1$ | $G^2$ | $G^3$ | $G^4$ |
|---|---|---|---|---|
| 7053 | Me | Me | H | CH(NMe$_2$)CF$_3$ |
| 7054 | Me | Me | H | CH(piperidinyl)CF$_3$ |
| 7055 | Me | Me | H | CH(imidazolyl)CF$_3$ |
| 7056 | Me | Me | H | CH(NHMe)CF$_3$ |
| 7057 | CH(propargylamino)CF$_3$ | Me | H | H |
| 7058 | CH(piperidinyl)CF$_3$ | Me | H | H |
| 7059 | CH(NMe$_2$)CF$_3$ | Me | Me | Cl |
| 7060 | CH(NMe$_2$)CF$_3$ | Me | H | Cl |
| 7061 | CH(piperidinyl)CF$_3$ | Me | H | Cl |
| 7063 | Me | Me | H | CH(N-methylpiperazinyl)CF$_3$ |
| 7065 | CH$_2$NMe$_2$ | CH$_2$CF$_3$ | Me | H |
| 7066 | CH$_2$CF$_3$ | Me | H | Cl |
| 7067 | CH$_2$NMe$_2$ | Me | H | H |
| 7069 | Me | CH$_2$CHF$_2$ | H | H |
| 7071 | CH$_2$(piperidinyl) | CH$_2$CF$_3$ | Me | H |
| 7073 | CH(N-methylpiperazinyl)CF$_3$ | Me | H | H |
| 7074 | CH (cyclopropylamino)CF$_3$ | Me | H | H |
| 7075 | CH (allylamino)CF$_3$ | Me | H | H |
| 7077 | NMe$_2$ | Me | CH$_2$CF$_3$ | H |
| 7080 | CH$_2$CHF$_2$ | Me | H | H |
| 7083 | CH2NMe$_2$ | CH$_2$CHF$_2$ | Me | H |

Test Results of Neuroprotective Effect of Compounds of Formula I on Hydrogen Peroxide Induced Apoptosis in SH-SY5Y Neuroblastoma Cells.

| Apo# | TH ($\mu$M) | EC$_{100}$ ($\mu$M) | CC1 ($\mu$M) | CC2 ($\mu$M) |
|---|---|---|---|---|
| 6994 | 40 | 160 | 160 | 640 |
| 6995 | 20 | 160 | 320 | 320 |
| 6998 | 10 | 80 | 20 | 100 |
| 7021 | 2.5 | 640 | 80 | >640 |
| 7022 | 5 | 160 | 40 | 320 |
| 7030 | 10 | 320 | 640 | >640 |
| 7032 | 160 | 640 | 10 | >640 |
| 7035 | 20 | 640 | 40 | >640 |
| 7038 | 20 | 320 | 40 | >640 |
| 7040 | 10 | 640 | 160 | >640 |
| 7041 | 10 | 80 | 160 | 320 |
| 7053 | 10 | 40 | 2.2 | >640 |
| 7054 | 2.5 | 640 | 5 | >640 |
| 7055 | 2.5 | 40 | 10 | >640 |
| 7057 | 3 | 20 | 5 | 80 |
| 7058 | 5 | 640 | 20 | >640 |
| 7059 | 10 | 320 | 40 | 640 |
| 7060 | 20 | 320 | 80 | >640 |
| 7061 | 10 | 640 | 10 | 10 |
| 7066 | 10 | 40 | 160 | 160 |
| 7067 | 10 | 40 | 160 | >640 |
| 7069 | 40 | 160 | 80 | >640 |
| 7071 | 3 | 20 | 20 | 80 |
| 7073 | 5 | 640 | 40 | >640 |
| 7074 | 3 | 640 | 20 | >640 |
| 7075 | 3 | 640 | 20 | >640 |
| 7080 | 10 | 320 | 40 | >640 |
| 7033 | 160 | 640 | 40 | >640 |
| 7063 | 5 | 640 | 320 | >640 |
| 7065 | 5 | 40 | 40 | >640 |

MC65 Assay Testing Results in the Protection Against Endogenously Produced A$\beta$ Toxicity

| Apo# | TH ($\mu$M) | EC$_{100}$ ($\mu$M) | CC1 ($\mu$M) | CC2 ($\mu$M) |
|---|---|---|---|---|
| 6994 | 1 | 10 | >80 | >80 |
| 6995 | 0.1 | 20 | 80 | 80 |
| 7021 | 0.1 | 10 | 10 | 20 |
| 7022 | 0.1 | 20 | 10 | 40 |
| 7030 | 1 | 20 | 40 | 40 |
| 7032 | 0.1 | 10 | 80 | 40 |
| 7035 | 0.1 | 10 | 40 | 20 |
| 7040 | 1 | 40 | 40 | 80 |
| 7041 | 0.1 | 10 | 10 | 80 |
| 7053 | 0.1 | 10 | 40 | 20 |
| 7054 | 0.1 | 1 | 20 | 20 |
| 7055 | 1 | 20 | 40 | 40 |
| 7056 | 0.1 | 10 | 80 | 80 |
| 7057 | 1 | 10 | 20 | 20 |
| 7058 | 1 | 10 | 10 | 80 |
| 7059 | 1 | 10 | 10 | 40 |
| 7060 | 1 | 10 | 40 | 20 |
| 7061 | 1 | 10 | 40 | 20 |
| 7066 | 0.1 | 10 | 80 | 80 |
| 7067 | 0.1 | 10 | 80 | 80 |
| 7069 | 0.1 | 40 | 80 | 80 |
| 7071 | 1 | 10 | 40 | 20 |
| 7073 | 0.1 | 10 | 40 | 20 |
| 7074 | 0.1 | 10 | 10 | 20 |
| 7075 | 0.1 | 10 | 10 | 20 |
| 7077 | 1 | 10 | 80 | 80 |
| 7080 | 0.1 | 10 | 40 | 40 |
| 7083 | 0.1 | 10 | 40 | 40 |

Example 33

Influence of MPP$^+$ (5 mM) on SV-NRA Cell Viability and the Neuroprotective Actions of Compounds of Formula I (Apo6995, Apo7060, 7021) on MPP$^+$ Treated SV-NRA Cells SV-NRAs cells were plated in a 96-well plate at a density of 10,000 cells/well in 100 $\mu$L of DME (dimethoxyethane), High glucose 1× liquid (Sigma) supplemented with 10% heat-inactivated FBS and 1× antibiotic/antimycotic solution (Sigma). On the next day, the cells were washed with EMEM media (Eagle's minimal essential media; phenol red, serum and glutamine free) and treated for 24 h with 5 mM MPP$^+$ (1-methyl-4-phenylpyridinium) in EMEM media in the presence or absence of a tested iron chelating compound. All compounds were tested at the following concentrations: 10 $\mu$M, 20 $\mu$M, and 40 $\mu$M. After 24 h of incubation, cell viability was determined with MTT ((3-(4,5-Dimethylthiazol-2-yl)-2,5-diphenyltetrazolium bromide, a yellow tetrazole) assay which measures mitochondrial activity (Carmichael et al. Cancer Research 1987, 47, 936-942). MTT solution (10 μL, 5 mg/mL) was added to the wells and incubated for 2 h. Formazan product was solubilized with 100 μL of 10% SDS (sodium dodecyl sulphate) in 0.01 M HCl. Optical density was determined at 570 nm using Multiscan Ascent plate reader (Labsystems) and data collected were corrected for background signal measured at 650 nm. All data are expressed as % of control.

MPP+ treatment resulted in about 40%-50% decrease in cell viability comparing to vehicle-treated control. Co-treatment with iron chelators protected the cells from MPP+ toxicity. Treatment with 20 μM deferiprone, an iron chelator drug resulted in about 20% increase in cell viability (p<0.05). Treatment with iron chelators Apo7060, Apo6995 and Apo7021 at concentrations of 10, 20, and 40 μM also increased cell viability by 20-30% (p<0.05) compared to MPP+ only treated cells. Representative results are shown in FIGS. 10, 11, 12, and 13.

What is claimed is:

1. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

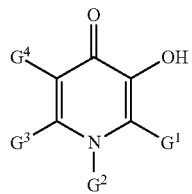

or a salt thereof,
wherein:
$G^1$ is the amine-containing substituent —$CH_2NR^1R^2$;
$G^2$ is $CH_2CF_2R^3$;
$G^3$ is H or $C_1$-$C_4$ alkyl;
$G^4$ is H or $C_1$-$C_4$ alkyl
$R^1$ and $R^2$ are either (a) two independent groups or (b) together form a single ring group including the N to which they are bonded, where
$R^1$ and $R^2$, when independent groups, are independently selected from the group consisting of: H, $C_1$-$C_4$ alkyl, $C_3$-$C_6$ cycloalkyl, allyl, and propargyl; or
$R^1$ and $R^2$, when together form a single ring group including the N to which they are bonded, are selected from the group consisting of: piperazinyl, N—($C_1$-$C_4$ alkyl)-substituted piperazinyl, and piperidinyl;
$R^3$ is H, or F.

2. The method of claim 1, wherein the medical condition is Friedreich's ataxia.

3. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

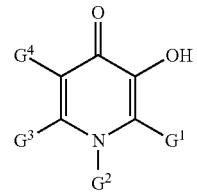

or a salt thereof,
wherein:
$G^1$ is the amine-containing substituent $CH(R^4)CF_3$ wherein $R^4$ is $NR^1R^2$ or A-NH—$R^{10}$;
$G^2$ is H, $C_1$-$C_4$ alkyl or cyclopropyl;
$G^3$ is H or $C_1$-$C_4$ alkyl;
$G^4$ is H or $C_1$-$C_4$ alkyl;
$R^1$ and $R^2$ are either (a) two independent groups or (b) together form a single ring group including the N to which they are bonded, where
$R^1$ and $R^2$, when independent groups, are independently selected from the group consisting of: H, $C_1$-$C_4$ alkyl, $C_3$-$C_6$ cycloalkyl, allyl, and propargyl; or
$R^1$ and $R^2$, when together form a single ring group including the N to which they are bonded, are selected from the group consisting of: piperazinyl, N—($C_1$-$C_4$ alkyl)-substituted piperazinyl, and piperidinyl;
$R^{10}$ is H or $C_1$-$C_4$ alkyl;
A is —NH—$(CH_2)_m$—CO— or an alpha amino acid residue; and
m is 1, 2 or 3.

4. The method of claim 3, wherein the medical condition is Friedreich's ataxia.

5. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

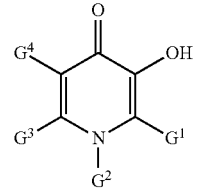

or a salt thereof,
wherein:
$G^1$ is —$CH(R^4)CF_3$ wherein $R^4$ is H or OH;
$G^2$ is H, $C_1$-$C_4$ alkyl or cyclopropyl;
$G^3$ is the amine-containing substituent $CH_2$-A-OH, $CH_2$-A-$NHR^9$, or $CH_2NR^1R^2$;
$G^4$ is H or $C_1$-$C_4$ alkyl;
$R^1$ and $R^2$ are either (a) two independent groups or (b) together form a single ring group including the N to which they are bonded, where $R^1$ and $R^2$, when independent groups, are independently selected from the group consisting of: H, $C_1$-$C_4$ alkyl, $C_3$-$C_6$ cycloalkyl, allyl, and propargyl; or $R^1$ and $R^2$, when together form a single ring group including the N to which they are bonded, are selected from the group consisting of: piperazinyl, N—($C_1$-$C_4$ alkyl)-substituted piperazinyl, and piperidinyl;

$R^9$ is H or $C_1$-$C_4$ alkyl;

A is —NH—$(CH_2)_m$—CO— or an alpha amino acid residue; and m is 1, 2 or 3.

6. The method of claim 5, wherein the medical condition is Friedreich's ataxia.

7. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

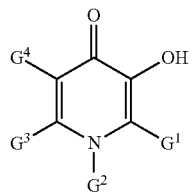

I or a salt thereof,
wherein:
$G^1$ is the amine-containing substituent —CH($R^4$)$CF_3$, wherein $R^4$ is $NR^1R^2$ or A-NH—$R^{10}$;

$G^2$ is H, $C_1$-$C_4$ alkyl or cyclopropyl;

$G^3$ is H or $C_1$-$C_4$ alkyl;

$G^4$ is halo;

$R^1$ and $R^2$ are either (a) two independent groups or (b) together form a single ring group including the N to which they are bonded, where $R^1$ and $R^2$, when independent groups, are independently selected from the group consisting of: H, $C_1$-$C_4$ alkyl, $C_3$-$C_6$ cycloalkyl, allyl, and propargyl; or $R^1$ and $R^2$, when together form a single ring group including the N to which they are bonded, are selected from the group consisting of: piperazinyl, N—($C_1$-$C_4$ alkyl)-substituted piperazinyl, and piperidinyl;

$R^{10}$ is H or $C_1$-$C_4$ alkyl;

A is —NH—$(CH_2)_m$—CO— or an alpha amino acid residue; and m is 1, 2 or 3.

8. The method of claim 7, wherein the medical condition is Friedreich's ataxia.

9. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

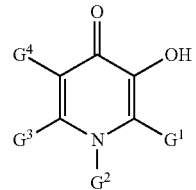

I or a salt thereof,
wherein:
$G^1$ is H, or $C_1$-$C_4$ alkyl;
$G^2$ is H, $C_1$-$C_4$ alkyl, or cyclopropyl;
$G^3$ is H, or $C_1$-$C_4$ alkyl;
$G^4$ is the amine-containing substituent —CH($CF_3$)($R^8$);
$R^8$ is $NR^1R^2$, imidazolyl or -A-NH—$R^{10}$;
$R^1$ and $R^2$ are either (a) two independent groups or (b) together form a single ring group including the N to which they are bonded, where $R^1$ and $R^2$, when independent groups, are independently selected from the group consisting of: H, $C_1$-$C_4$ alkyl, $C_3$-$C_6$ cycloalkyl, allyl, and propargyl; or $R^1$ and $R^2$, when together form a single ring group including the N to which they are bonded, are selected from the group consisting of: piperazinyl, N—($C_1$-$C_4$ alkyl)-substituted piperazinyl, and piperidinyl;

$R^{10}$ is H or $C_1$-$C_4$ alkyl;

A is —NH—$(CH_2)_m$—CO— or an alpha amino acid residue; and m is 1, 2 or 3.

10. The method of claim 9, wherein the medical condition is Friedreich's ataxia.

11. A method of treating a medical condition related to a toxic concentration of iron selected from the group consisting of progressive kidney disease in which the presence of iron is detected in the urine and Friedreich's ataxia, wherein the method comprises administering to a patient an effective amount of an amine-containing fluorinated 3-hydroxypyridin-4-(1H)-one compound of Formula I:

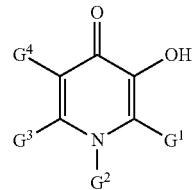

I or a salt thereof
wherein
$G^1$ is the amine-containing substituent $CH_2NR^1R^2$ or $NR^1R^2$;
$G^2$ is $C_1$-$C_4$ alkyl, or cyclopropyl;
$G^3$ is —CH($R^6$)($CF_3$);
$G^4$ is H, or $C_1$-$C_4$ alkyl;
$R^1$ and $R^2$ are either (a) two independent groups or (b) together form a single ring group including the N to which they are bonded, where $R^1$ and $R^2$, when independent groups, are independently selected from the group consisting of: H, $C_1$-$C_4$ alkyl, $C_3$-$C_6$ cycloalkyl, allyl, and propargyl; or $R^1$ and $R^2$, when together form a single ring group including the N to which they are bonded, are selected from the group consisting of: piperazinyl, N—($C_1$-$C_4$ alkyl)-substituted piperazinyl, and piperidinyl; and $R^6$ is H or OH.

12. The method of claim 11, wherein the medical condition is Friedreich's ataxia.

* * * * *